(12) United States Patent
Hecht et al.

(10) Patent No.: US 10,472,340 B2
(45) Date of Patent: Nov. 12, 2019

(54) SUBSTITUTED PHENOTHIAZINES AS MITOCHONDRIAL AGENTS

(71) Applicant: ARIZONA BOARD OF REGENTS ON BEHALF OF ARIZONA STATE UNIVERSITY, Scottsdale, AZ (US)

(72) Inventors: Sidney Hecht, Phoenix, AZ (US); Omar Khdour, Phoenix, AZ (US); Sandipan Roy Chowdhury, Tempe, AZ (US); Indrajit Bandyopadhyay, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1 day.

(21) Appl. No.: 15/550,282

(22) PCT Filed: Feb. 17, 2016

(86) PCT No.: PCT/US2016/018233
§ 371 (c)(1),
(2) Date: Sep. 8, 2018

(87) PCT Pub. No.: WO2016/133995
PCT Pub. Date: Aug. 25, 2016

(65) Prior Publication Data
US 2018/0065941 A1 Mar. 8, 2018

Related U.S. Application Data

(60) Provisional application No. 62/117,205, filed on Feb. 17, 2015.

(51) Int. Cl.
*A61K 31/5415* (2006.01)
*C07D 279/18* (2006.01)
*C07D 279/20* (2006.01)
*C07D 417/04* (2006.01)
*C07D 417/14* (2006.01)

(52) U.S. Cl.
CPC ......... *C07D 279/20* (2013.01); *C07D 279/18* (2013.01); *C07D 417/04* (2013.01); *C07D 417/14* (2013.01)

(58) Field of Classification Search
CPC .................... A61K 31/5415; C07D 279/18
USPC .......................................... 514/224.8; 544/37
See application file for complete search history.

(56) References Cited

U.S. PATENT DOCUMENTS

| | | | |
|---|---|---|---|
| 3,476,722 A | 11/1969 | Schlatzer | |
| 4,054,580 A | 10/1977 | Ohi | |
| 4,338,180 A | 7/1982 | Nakamura | |
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,220,042 A | 6/1993 | Iwaki et al. | |
| 5,356,898 A | 10/1994 | Belliotti et al. | |
| 8,268,849 B2 | 9/2012 | Kador et al. | |
| 8,759,336 B2 | 6/2014 | Hurt et al. | |
| 8,952,025 B2 | 2/2015 | Hecht et al. | |
| 9,102,626 B2 | 8/2015 | Hecht et al. | |
| 9,334,250 B2 | 5/2016 | Chowdhury et al. | |
| 9,388,163 B2 | 7/2016 | Hecht et al. | |
| 9,440,967 B2 | 9/2016 | Hecht et al. | |
| 9,957,214 B2 | 5/2018 | Madathil et al. | |
| 2001/0027196 A1 | 10/2001 | Borroni et al. | |
| 2004/0166553 A1 | 8/2004 | Nguyen et al. | |
| 2008/0062838 A1 | 3/2008 | Selinfreund et al. | |
| 2010/0016783 A1 | 1/2010 | Bourke, Jr. et al. | |
| 2011/0319380 A1 | 12/2011 | Hardy et al. | |
| 2013/0224634 A1 | 8/2013 | Berneth et al. | |
| 2013/0267546 A1 | 10/2013 | Hecht et al. | |
| 2013/0267548 A1 | 10/2013 | Follmann et al. | |
| 2013/0317012 A1 | 11/2013 | Wischik et al. | |
| 2014/0127737 A1 | 5/2014 | Kim | |
| 2014/0275045 A1 | 9/2014 | Hinman et al. | |
| 2018/0319751 A1 | 11/2018 | Hecht et al. | |

FOREIGN PATENT DOCUMENTS

| | | | |
|---|---|---|---|
| DE | 2315349 A1 | 10/1974 | |
| JP | 2001209176 A | 8/2001 | |
| WO | 1996031217 A1 | 10/1996 | |
| WO | 2002000683 A2 | 1/2002 | |
| WO | 2003007950 A1 | 1/2003 | |
| WO | 2006089301 A2 | 8/2006 | |
| WO | 2006100212 A1 | 9/2006 | |
| WO | 2009142760 A1 | 11/2009 | |
| WO | 2011103536 A1 | 8/2011 | |

(Continued)

OTHER PUBLICATIONS

Turrens, "Mitochondrial formation of reactive oxygen species", J Physiol 552, 335-344 (2003).
USPTO, Final Office Action for U.S. Appl. No. 13/855,133, dated Jun. 17, 2014, 9 pages.
USPTO, Final Office Action for U.S. Appl. No. 14/009,437, dated Mar. 18, 2015, 8 pages.
USPTO, Final Office Action for U.S. Appl. No. 14/371,579, dated Sep. 2, 2015, 11 pages.
USPTO, Final Office Action for U.S. Appl. No. 14/434,725, notification date Febraury 28, 2017, 10 pages.

(Continued)

*Primary Examiner* — Douglas M Willis
(74) *Attorney, Agent, or Firm* — Viksnins Harris Padys Malen LLP

(57) ABSTRACT

The present disclosure provides phenothiazine derivative compounds and salts thereof, compositions comprising these compounds, and methods of using these compounds in a variety of applications, such as treatment or suppression of diseases associated with decreased mitochondrial function resulting in diminished ATP production and/or oxidative stress and/or lipid peroxidation.

8 Claims, 8 Drawing Sheets

(56) References Cited

FOREIGN PATENT DOCUMENTS

| WO | 2012022467 A2 | 2/2012 |
| WO | 2012138713 A2 | 10/2012 |
| WO | 2013120040 A1 | 8/2013 |
| WO | 2013120081 A1 | 8/2013 |
| WO | 2014055629 A1 | 4/2014 |
| WO | 2014059158 A1 | 4/2014 |
| WO | 2014145119 A1 | 9/2014 |
| WO | 2016133959 A1 | 8/2016 |
| WO | 2016133995 A1 | 8/2016 |
| WO | 2017218537 A1 | 12/2017 |
| WO | 2016133959 A9 | 2/2018 |
| WO | 2018039077 A1 | 3/2018 |
| WO | 2018039487 A1 | 3/2018 |
| WO | 2018039077 A8 | 9/2018 |

OTHER PUBLICATIONS

USPTO, Non-Final Office Action for U.S. Appl. No. 13/855,133, dated Dec. 3, 2013, 10 pages.
USPTO, Non-Final Office Action for U.S. Appl. No. 14/009,437, dated Dec. 9, 2014, 8 pages.
USPTO, Non-Final Office Action for U.S. Appl. No. 14/371,579, dated Mar. 18, 2015, 17 pages.
USPTO, Non-Final Office Action for U.S. Appl. No. 14/432,885, dated Nov. 12, 2015, 6 pages.
USPTO, Non-Final Office Action for U.S. Appl. No. 14/434,725, notification date Aug. 23, 2017, 12 pages.
USPTO, Non-Final Office Action for U.S. Appl. No. 14/434,725, notification date Aug. 29, 2016, 17 pages.
USPTO, Non-Final Office Action for U.S. Appl. No. 14/731,950, dated Nov. 6, 2015, 7 pages.
Van Haaften, et al., "No reduction of alpha-tocopherol quinone by glutathione in rat liver microsomes", Biochem Pharmacol 61(6), 715-719 (2001).
Viehe, et al., "The captodative effect", Acc Chem Res 18(5), 148-154 (1985).
Vinod, et al., "Os(VIII) as an Efficient Homogeneous Catalyst for the Oxidative Decolorization of Methylene Blue Dye with Alkaline Chloramine-T: Kinetic, Mechanistic, and Platinum Metal Ions Reactivity Studies", Ind Eng Chem Res 49(7), 3137-3145 (2010).
Wallace, "Mouse models for mitochondrial disease", Am J Med Genet 106(1), 71-93 (2001).
Wijtmans, et al., "6-Amino-3-Pyridinols: Towards Diffusion-Controlled Chain-Breaking Antioxidants", Angew Chem Int Ed 42(36), 4370-4373 (2003).
Wijtmans, et al., "Synthesis and Reactivity of Some 6-Substituted-2,4-dimethyl-3-pyridinols, a Novel Class of Chain-Breaking Antioxidants", J. Org. Chem.69(26), 9215-9223 (2004).
Wilson, "Frataxin and frataxin deficiency in Friedreich's ataxia", J. Neurol. Sci. 207(1-2), 103-105 (2003).
Wilson, et al., "Respiratory deficiency due to loss of mitochondrial DNA in yeast lacking the frataxin homologue", Nature Genetics 16(4), 352-357 (1997).
Wright, et al., "Lifespan and mitochondrial control of neurodegeneration", Nat Genet 36(11), 1153-1158 (2004).
Wu, et al., "Autoxidation of phosphatidylcholine liposomes", Lipids 17(6), 403-413 (1982).
Yamada, et al., "Immunochemical detection of a lipofuscin-like fluorophore derived from malondialdehyde and lysine", J. Lipid Res. 42(8), 1187-1196 (2001).
Yin, et al., "Biochemical basis of lipofuscin, ceroid, and age pigment-like fluorophores", Free Rad. Biol. Med. 21(6), 871-888 (1996).
Ying, et al., "Inhibition of mitochondrial calcium ion transport by an oxo-bridged dinuclear ruthenium ammine complex", Biochemistry 30(20), 4949-4952 (1991).
Yoon, et al., "Frataxin-mediated Iron Delivery to Ferrochelatase in the Final Step of Heme Biosynthesis", J. Biol. Chem. 279(25), 25943-25946 (2004).
Yoon, et al., "Iron-sulfur cluster biosynthesis. Characterization of frataxin as an iron donor for assembly of [2Fe-2S] clusters in ISU-type proteins", J. Am. Chem. Soc. 125(20), 6078-6084 (2003).
Yoshihara, et al., "Hydroxybenzoquinones from Myrsinaceae Plants. IV. Further Confirmation of the Structures of Ardisiaquinones and Some Observations on Alkylaminobenzoquinone Derivatives", Chem Pharm Bull 16(12), 2383-2389 (1968).
Zhang, et al., "Bax and the mitochondrial permeability transition cooperate in the release of cytochrome c during endoplasmic reticulum-stress-induced apoptosis", Cell Death Differ 14(4), 703-715 (2007, available online 2006).
Zhang, et al., "The mitochondrial permeability transition regulates cytochrome c release for apoptosis during endoplasmic reticulum stress by remodeling the cristae junction", J Biol Chem 283(6), 3476-3486 (2008, available online 2007).
Zierz, et al., "Exogenous coenzyme Q (coq) fails to increase coq in skeletal muscle of two patients with mitochondrial myopathies", J Neurol Sci 95(3), 283-290 (1990).
Zimmerman, et al., "Mitochondrial Dysfunction and Mitochondrial-Produced Reactive Oxygen Species: New Targets for Neurogenic Hypertension?", Hypertension 53(2), 112-114 (2008).
Leonard, et al., "Mitochondrial respiratory chain disorders I: mitochondrial DNA defects", Lancet 355(9200), 299-304 (2000).
Lerman-Sagie, et al., "Dramatic improvement in mitochondrial cardiomyopathy following treatment with idebenone", J Inherit Metab Dis 24(1), 28-34 (2001).
Ley, et al., "Tetrapropylammonium Perruthenate, Pr4N+RuO4−, TPAP: A Catalytic Oxidant for Organic Synthesis", Synthesis 1994(7), 639-666 (1994).
Lin, et al., "A nitrogen-containing 3-alkyl-1,4-benzoquinone and a gomphilactone derivative from Embelia ribes", J. Nat. Prod. 69(11), 1629-1632 (2006).
Lin, et al., "Mitochondrial dysfunction and oxidative stress in neurodegenerative diseases", Nature 443(7113), 787-795 (2006).
Lowes, et al., "The mitochondria-targeted antioxidant MitoQ protects against organ damage in a lipopolysaccharide-peptidoglycan model of sepsis", Free Radic Biol Med 45(11), 1559-1565 (2008).
Lu, et al., "Concise Synthesis of Bicyclic Pyridinol Antioxidants", Org Lett 12(22), 5189-5191 (2010).
Lu, et al., "Design, synthesis, and evaluation of an α-tocopherol analogue as a mitochondrial antioxidant", Bioorg Med Chem 18(21), 7628-7638 (2010).
Lu, et al., "Role of calcium and cyclophilin D in the regulation of mitochondrial permeabilization induced by glutathione depletion", Biochem Biophys Res Commum 363(3), 572-577 (2007).
Luly, et al., "Routes to Mitomycins, New Syntheses of the 2,3,5,8-Tetrahydro-5,8-dioxo-1H-pyrrolo[1,2a] indole Ring System. An Efficient Synthesis of 7-Methoxymitosene", J. Am. Chem. Soc. vol. 105, 2859-2866, (1983).
Maccoubrey, et al., "Quantitative fluorescence measurements of cell viability (cytotoxicity) with a multi-well plate scanner", J Cell Biol 111(5), 58a, (1990).
Mackenzie, et al., "The Biological Activity of Alpha-Tocopherylhydroquinone and Alpha-Tocopherylquinone", J Biol Chem 183(2), 655-662 (1950).
Manfredini, et al., "Novel antioxidant agents deriving from molecular combinations of vitamins C and E analogues: 3,4-dihydroxy-5(R)-[2(R,S)-(6-hydroxy-2,5,7,8-tetramethyl-chroman-2(R,S)-yl-methyl)-[1,3]dioxolan-4(S)-yl]-5H-furan-2-one and 3-O-octadecyl derivatives", Bioorg Med Chem 8(12), 2791-2801 (2000).
Manton, et al., "ROS effects on neurodegeneration in Alzheimer's disease and related disorders: on environmental stresses of ionizing radiation", Curr Alzheimer Res 1(4), 277-293 (2004).
Markesbery, et al., "Oxidative alterations in Alzheimer's disease", Brain Pathology 9(1), 133-146 (1999).
Markovits, et al., "Ethidium dimer: a new reagent for the fluorimetric determination of nucleic acids", Anal Biochem 94(2), 259-264 (1979).
Mates, et al., "Antioxidant enzymes and human diseases", Clin Biochem 32, 595-603 (1999).

(56) References Cited

OTHER PUBLICATIONS

Matlib, et al., "Oxygen-bridged dinuclear ruthenium amine complex specifically inhibits Ca2+ uptake into mitochondria in vitro and in situ in single cardiac myocytes", J Biol Chem 273(17), 10223-10231 (1998).
Matsuno-Yagi, et al., "Studies on the mechanism of oxidative phosphorylation: Catalytic site cooperativity in ATP synthesis", J. Biol. Chem. 260(27), 14424-14427 (1985).
Matthews, et al., "Coenzyme Q10 with multiple vitamins is generally ineffective in treatment of mitochondrial disease", Neurology 43(5), 884-890 (1993).
McBride, et al., "Mitochondria: more than just a powerhouse", Curr Biol 16, R551-R560 (2006).
McBride, et al., "Nucleotide chemistry. 16. Amidine protecting groups for oligonucleotide synthesis", J Am Chem Soc 108(8), 2040-2048 (1986).
McErlean, et al., "First Synthesis of N-(3-Carboxylpropyl)-5-amino-2-hydroxy-3- tridecyl-1,4-benzoquinone, an Unusual Quinone Isolated from Embelia ribes", Journal of Organic Chemistry, 72(26),10298-10301 (2007).
Minta, et al., "Fluorescent indicators for cytosolic calcium based on rhodamine and fluorescein chromophores", J Biol Chem 264(14), 8171-8178 (1989).
Moore, et al., "A rapid pH insensitive, two color fluorescence viability (cytotoxicity) assay", J Cell Bio 111(5), 58a (1990).
Moore, et al., "Alpha-Tocopheryl Quinone is Converted into Vitamin E in Man", Free Radic Biol Med 22(5), 931-934 (1997).
Mossa, et al., "Alkylated benzoquinone derivatives from Maesa lanceolata", Phytochemistry 50(6), 1063-1068 (1999).
Moubarak, et al., "Hepatic metabolism of ergot alkaloids in beef cattle by cytochrome P450", Biochem Biophys Res Commun 274, 746-749 (2000).
Murphy, "Development of lipophilic cations as therapies for disorders due to mitochondrial dysfunction", Expert Opin Biol Ther 1(5), 753-764 (2001).
Murphy, et al., "Drug delivery to mitochondria: the key to mitochondrial medicine", Adv. Drug Delivery Rev. 41(2), 235-250 (2000).
Murphy, "How mitochondria produce reactive oxygen species", Biochem J 417(1), 1-13 (2009).
Nam, et al., "New synthetic route to N-tocopherol derivatives: synthesis of pyrrolopyridinol analogue of α-tocopherol from pyridoxine", Org Biomol Chem 9(6), 1749-1755 (2011).
Nam, et al., "Pyridoxine-derived bicyclic aminopyridinol antioxidants: synthesis and their antioxidant activities", Org Biomol Chem 9(24), 8475-8482 (2011).
Nam, et al., "Tetrahydro-1,8-naphthyridinol analogues of alpha-tocopherol as antioxidants in lipid membranes and low-density lipoproteins", J Am Chem Soc 129(33), 10211-10219 (2007).
Newmeyer, et al., "Erratum for Mitochondria: releasing power for life and unleashing the machineries of death", Cell 112(6), 873 (2003).
Newmeyer, et al., "Mitochondria: releasing power for life and unleashing the machineries of death", Cell 112(4), 481-490 (2003).
Niki, et al., "Dynamics of antioxidant action of vitamin E", Acc Chem Res 37(1), 45-51 (2004, available online 2003).
Ogasahara, et al., "Improvement of abnormal pyruvate metabolism and cardiac conduction defect with coenzyme Q10 in Kearns-Sayre syndrome", Neurology 35(3), 372-377 (1985).
Ogawa, "Hydroxybenzoquinones from myrsinaceae plants-II.: Distribution among myrsinaceae plants in Japan., Phytochemistry", Phytochemistry 7(5), 773-782 (1968).
Omura, et al., "Oxidation of alcohols by "activated" dimethyl sulfoxide. a preparative, steric and mechanistic study", Tetrahedron 34(11), 1651-1660 (1978).
Osakada, et al., "Alpha-tocotrienol provides the most potent neuroprotection among vitamin E analogs on cultured striatal neurons", Neuropharmacology 47(6), 904-915 (2004).
Osakada, et al., "Neuroprotective effects of alpha-tocopherol on oxidative stress in rat striatal cultures", Eur J Pharmacol 465(1-2), 15-22 (2003).
Ouahchi, et al., "Ataxia with isolated vitamin E deficiency is caused by mutations in the alpha-tocopherol transfer protein", Nat Genet 9(2), 141-145 (1995).
Palozza, et al., "Retracted: Design, synthesis, and antioxidant potency of novel α-tocopherol analogues in isolated membranes and intact cells", Free Redic Biol Med 44(7), 1452-1464 (2008).
Palozza, et al., "Retraction notice to: "Design, synthesis, and antioxidant potency of novel α-tocopherol analogues in isolated membranes and intact cells", [Free Radical Biology & Medicine 44 (2008) 1452-1464]", Free Redic Biol Med 75, 252 (2014).
Pap, et al., "Ratio-£uorescence microscopy of lipid oxidation in living cells usingC11-BODIPY581=591", FEBS Lett 453, 278-282 (1999).
Park, et al., "Yeast frataxin sequentially chaperones and stores iron by coupling protein assembly with iron oxidation", J. Biol. Chem. 278(33), 31340-31351 (2003).
Patent Cooperation Treaty, International Searching Authority, International Preliminary Report on Patentability and Written Opinion for PCT/US2011/025613, 8 pages, report dated Aug. 21, 2012.
Patent Cooperation Treaty, International Searching Authority, International Preliminary Report on Patentability and Written Opinion for PCT/US2012/032108, 9 pages, report dated Oct. 8, 2013.
Patent Cooperation Treaty, International Searching Authority, International Preliminary Report on Patentability and Written Opinion for PCT/US2013/025590, 8 pages, report dated Aug. 12, 2014.
Patent Cooperation Treaty, International Searching Authority, International Preliminary Report on Patentability and Written Opinion for PCT/US2013/063034, 5 pages, report dated Apr. 7, 2015.
Patent Cooperation Treaty, International Searching Authority, International Preliminary Report on Patentability and Written Opinion for PCT/US2013/064359, 6 pages, report dated Apr. 14, 2015, dated Feb. 10, 2014.
Patent Cooperation Treaty, International Searching Authority, International Preliminary Report on Patentability and Written Opinion for PCT/US2016/018233, 12 pages, report dated Aug. 22, 2017, dated Apr. 29, 2016.
Patent Cooperation Treaty, International Searching Authority, International Search Report for PCT/US2011/025613, 5 pages, dated Jul. 25, 2011.
Patent Cooperation Treaty, International Searching Authority, International Search Report for PCT/US2012/032108, 6 pages, dated Jan. 23, 2013.
Patent Cooperation Treaty, International Searching Authority, International Search Report for PCT/US2013/025590, 5 pages, dated May 6, 2013.
Patent Cooperation Treaty, International Searching Authority, International Search Report for PCT/US2013/063034, 3 pages, dated Nov. 15, 2013.
Patent Cooperation Treaty, International Searching Authority, International Search Report for PCT/US2013/064359, 3 pages, dated Feb. 10, 2014.
Patent Cooperation Treaty, International Searching Authority, International Search Report for PCT/US2016/018233, 4 pages, dated Apr. 29, 2016.
Patent Cooperation Treaty, International Searching Authority, International Search Report for PCT/US2017/037253, 2 pages, dated Aug. 16, 2017.
Patent Cooperation Treaty, International Searching Authority, International Search Report for PCT/US2017/047640, 3 pages, dated Oct. 30, 2017.
Patent Cooperation Treaty, International Searching Authority, International Search Report for PCT/US2017/048482, 4 pages, dated Dec. 7, 2017.
Patent Cooperation Treaty, International Searching Authority, Search Report and Written Opinion for PCT/US2016/18233, 16 pages, dated Apr. 29, 2016.
Patent Cooperation Treaty, International Searching Authority, Written Opinion for PCT/US2017/037253, 5 pages, dated Aug. 16, 2017.
Patent Cooperation Treaty, International Searching Authority, Written Opinion for PCT/US2017/047640, 4 pages, dated Oct. 30, 2017.
Patent Cooperation Treaty, International Searching Authority, Written Opinion for PCT/US2017/048482, 5 pages, dated Dec. 7, 2017.

(56) References Cited

OTHER PUBLICATIONS

Piancatelli, et al., "Pyridinium Chlorochromate: A Versatile Oxidant in Organic Synthesis", Synthesis 1982(4), 245-258 (1982).
Pisano, et al., "Plasma concentrations and pharmacokinetics of idebenone and its metabolites following single and repeated doses in young patients with mitochondrial encephalomyopathy", Eur J Clin 51(2), 167-169 (1996).
Pratt, et al., "5-Pyrimidinols: novel chain-breaking antioxidants more effective than phenols", J Am Chem Soc 123 (19), 4625-4626 (2001).
Pubchem, "3H-Phenothiazin-3-one", CID 68485, 17 pages (Create Date Mar. 26, 2005).
Pubchem, "7-((4-nitrobenzyl)oxy)-2H-chromen-2-one", SID 164870287, create date Nov. 14, 2013, Version 1 (modified Nov. 14, 2013), retrieved Dec. 4, 2018, <https://pubchem.ncbi.nlm.nih.gov/substance/164870287/version/1>.
Pubchem, "7-((4-nitrobenzyl)oxy)-2H-chromen-2-one", SID 164870287, create date Nov. 14, 2013, Version 6 (modified Nov. 28, 2015), retrieved Dec. 4, 2018, <https://pubchem.ncbi.nlm.nih.gov/substance/164870287/version/6>.
Pubchem, "7-(dimethylamino)-3H-phenothiazin-3-one", SID 224730291, create date Feb. 2, 2015, Version 1 (modified Feb. 2, 2015), retrieved Dec. 4, 2018, <https://pubchem.ncbi.nlm.nih.gov/substance/224730291/version/1>.
Pubchem, "7-(dimethylamino)-3H-phenothiazin-3-one", SID 224730291, create date Feb. 2, 2015, Version 2 (modified Nov. 15, 2017), retrieved Dec. 4, 2018, <https://pubchem.ncbi.nlm.nih.gov/substance/224730291/version/2>.
Pubchem, "MLS002699551", SID 92763509, create date May 10, 2010, Version 1 (modified May 10, 2010), retrieved Dec. 4, 2018, <https://pubchem.ncbi.nlm.nih.gov/substance/92763509/version/1>.
Pubchem, "MLS002699551", SID 92763509, create date May 10, 2010, Version 3 (modified Mar. 1, 2012), retrieved Dec. 4, 2018, <https://pubchem.ncbi.nlm.nih.gov/substance/92763509/version/3>.
Quinzii, et al., "Respiratory chain dysfunction and oxidative stress correlate with severity of primary CoQ10 deficiency", FASEB J. 22(6), 1874-1885 (2008).
Ramasarma, et al., "Studies on the Electron Transport System", J Biol Chem 235(11), 3309-3314 (1960).
Reddy, "Amyloid precursor protein-mediated free radicals and oxidative damage: implications for the development and progression of Alzheimer's disease", J Neurochem 96(1), 1-13 (2006, available online 2005).
Reddy, et al., "Are mitochondria critical in the pathogenesis of Alzheimer's disease", Brain Res Brain Res Rev 49(3), 618-632 (2005).
Robuschi, et al., "The Action of Light and of Photodynamic Substances on Carbohydrate Metabolism", Sperimentale 94, 99-124 (1940).
Rotig, et al., "Molecular insights into Friedreich's ataxia and antioxidant-based therapies", Trends Mol Med 8(5), 221-224 (2002).
Rustin, et al., "Idebenone treatment in Friedreich patients: one-year-long randomized placebo-controlled trial", Neurology 62(3), 524-525 (2004).
Saraste, "Oxidative phosphorylation at the fin de siècle", Science 283, 1488-1493 (1999).
Scavo, et al., "Preparation of alpha,beta-dehydro-beta-amino acid derivatives by tin-promoted addition of malonates to simple nitriles", Tetrahedron Lett 26(22), 2603-2606 (1985).
Shue, et al., "Targeting antioxidants to mitochondria: a new therapeutic direction", Biochim Biophys Acta 1762(2), 256-265 (2006, available online 2005).
Smith, "[13] Preparation, properties, and conditions for assay of mitochondria: Slaughterhouse material, small-scale", Methods Enzymol 10, 81-86 (1967).
Smith, et al., "Delivery of Bioactive Molecules to Mitochondria in vivo", PNAS, vol. 100, No. 9, 5407-5412 (2003).
Smith, et al., "Measurement of protein using bicinchoninic acid", Anal Biochem 150(1), 76-85 (1985).
Smith, et al., "Using mitochondria-targeted molecules to study mitochondrial radical production and its consequences", Biochem Soc Trans 31(6), 1295-1299 (2003).
Syper, "The Baeyer-Villiger Oxidation of Aromatic Aldehydes and Ketones with Hydrogen Peroxide Catalyzed by Selenium Compounds. A Convenient Method for the Preparation of Phenols", Synthesis 1989(3), 167-172 (1989).
Takano, et al., "An Efficient Stereoselective Preparation of Vitamin E (α-Tocopherol) from Phytol", Synlett 1990(8), 451-452 (1990).
Takano, et al., "Asymmetric construction of optically active 3-hydroxyalkyne functionalities", J Chem Soc Chem Commun (18), 1344-1345 (1989).
Takenaka, et al., "The effect of alpha-tocopherol as an antioxidant on the oxidation of membrane protein thiols induced by free radicals generated in different sites", Arch Biochem Biophys 285(2), 344-350 (1991).
Tallman, et al., "Kinetic Products of Linoleate Peroxidation: Rapid β-Fragmentation of Nonconjugated Peroxyls", J Am Chem Soc 123(47), 11827-11828 (2001).
Tirmenstein, et al., "Glutathione depletion and the production of reactive oxygen species in isolated hepatocyte suspensions", Chem Biol Interact 127(3), 201-217 (2000).
Traber, et al., "Human plasma vitamin E kinetics demonstrate rapid recycling of plasma RRR-alpha-tocopherol", Proc Natl Acad Sci USA 91(21), 10005-10008 (1994).
Traber, et al., "Preferential incorporation of alpha-tocopherol vs gamma-tocopherol in human lipoproteins", Am J Clin Nutr 49(3), 517-526 (1989).
Trnka, et al., "Antioxidant properties of MitoTEMPOL and its hydroxylamine", Free Radic Res 43(1), 4-12 (2009).
Trounce, et al., "Assessment of mitochondrial oxidative phosphorylation in patient muscle biopsies, lymphoblasts, and transmitochondrial cell lines", Methods Enzymol. 264, 484-509 (1996).
U.S. Appl. No. 15/550,273, 2018-0319751.
Abe, et al., "Marked Reduction in CSF Lactate and Pyruvate Levels After CoQ Therapy in a Patient with Mitochondrial Myopathy, Encephalopathy, Lactic Acidosis and Stroke-like Episodes (MELAS)", Acta Neural Scand 83(6), 356-359 (1991).
Aguer, et al., "Galactose enhances oxidative metabolism and reveals mitochondrial dysfunction in human primary muscle cells", PLoS One 6(12), e28536 (2011).
Alam, et al., "Cytoprotective Pyridinol Antioxidants as Potential Therapeutic Agents for Neurodegenerative and Mitochondrial Diseases", Bioorganic & Medicinal Chemistry 22, 4935-4947 (2014).
Arce, et al., "A Strategy for Suppressing Redox Stress within Mitochondria", ACS Med Chem Lett 2(8), 608-613 (2011).
Arce, et al., "Analysis of the structural and mechanistic factors in antioxidants that preserve mitochondrial function and confer cytoprotection", Bioorganic & Medicinal Chemistry 20(17), 5188-5201 (2012).
Armstrong, et al., "Cysteine starvation activates the redox-dependent mitochondrial permeability transition in retinal pigment epithelial cells", Invest Ophthalmol Vis Sci 45(11), 4183-4189 (2004).
Armstrong, et al., "Does Oxidative Stress Contribute to the Pathology of Friedreich's Ataxia? A Radical Question", FASEB J 24(7), 2152-2163 (2010).
Armstrong, et al., "Glutathione depletion enforces the mitochondrial permeability transition and causes cell death in Bcl-2 overexpressing HL60 cells", FASEB J 16(10), 1263-1265 (2002).
Armstrong, et al., "The coenzyme Q10 analog decylubiquinone inhibits the redox-activated mitochondrial permeability transition: role of mitochondrial respiratory chain complex III", J Biol Chem 278(49), 49079-49084 (2003).
Asin-Cayuela, et al., "Fine-tuning the hydrophobicity of a mitochondria-targeted antioxidant", FEBS Lett 571(1-3), 9-16 (2004).
Atamna, et al., "Methylene blue delays cellular senescence and enhances key mitochondrial biochemical pathways", FASEB J 22(3), 703-712 (2008, available online 2007).
Barbiroli, et al., "Coenzyme Q10 improves mitochondrial respiration in patients with mitochondrial cytopathies. An in vivo study on

(56) References Cited

OTHER PUBLICATIONS brain and skeletal muscle by phosphorous magnetic resonance spectroscopy", Cell Mol Biol 43(5), 741-749 (1997).
Barnham, et al., "Neurodegenerative diseases and oxidative stress", Nat Rev Drug Discov 3(3), 205-214 (2004).
Benard, et al., "Ultrastructure of the mitochondrion and its bearing on function and bioenergetics", Antioxid Redox Signal 10(8), 1313-1342 (2008).
Bencze, et al., "Human frataxin: iron and ferrochelatase binding surface", J.C.S. Chem. Commun. 14(18), 1798-1800 (2007).
Bendahan, et al., "31P NMR spectroscopy and ergometer exercise test as evidence for muscle oxidative performance improvement with coenzyme Q in mitochondrial myopathies", Neurology 42(6), 1203-1208 (1992).
Boduszek, et al., "A New Method for the Preparation of Pyridine-4-phosphonic Acids", Synthesis 1979(6), 452-453 (1979).
Bradley, et al., "Clinical, biochemical and molecular genetic correlations in Friedreich's ataxia", Hum. Mol. Genet. 9 (2), 275-282 (2000).
Bras, et al., "Programmed cell death via mitochondria: different modes of dying", Biochemistry (Mosc) 70(2), 231-239 (2005).
Bresolin, et al., "Clinical and biochemical correlations in mitochondrial myopathies treated with coenzyme Q10", Neurology 38(6), 892-898 (1988).
Bresolin, et al., "Ubidecarenone in the treatment of mitochondrial myopathies: a multi-center double-blind trial", J Neuro Sci 100(1-2), 70-78 (1990).
Brigelius-Flohe, et al., "Vitamin E: function and metabolism", FASEB J 13(10), 1145-1155 (1999).
Brown, et al., "Potential Antimalarials in the 4-Dialkylaminomethyl-2-Methyl-3-Pyridol Series", J Org Chem 11(4), 388-389 (1946).
Bulteau, et al., "Frataxin Acts as an Iron Chaperone Protein to Modulate Mitochondrial Aconitase Activity", Science 305(5681), 242-245 (2004).
Burton, et al., "Vitamin E: application of the principles of physical organic chemistry to the exploration of its structure and function", Acc Chem Res 19(7), 194-201 (1986).
Cadenas, et al., "Mitochondrial free radical generation, oxidative stress, and aging", Free Radic Biol Med 29(3-4), 222-230 (2000).
Cadenas, et al., "Mitochondrial free radical production and cell signaling", Mol Aspects Med 25(1-2), 17-26 (2004).
Cai, et al., "Simplified bicyclic pyridinol analogues protect mitochondrial function", Bioorganic Med Chem 20(11), 3584-3595 (2012).
Calabrese, et al., "Oxidative stress, mitochondrial dysfunction and cellular stress response in Friedreich's ataxia", J Neuro Sci 233(1-2), 145-162 (2005).
Calza, et al., "Light-induced transformations of fungicides on titanium dioxide: pathways and by-products evaluation using the LC-MS technique", Int J Environ Anal Chem 86(3-4), 265-275 (2006).
Campuzano, et al., "Frataxin is Reduced in Friedreich Ataxia Patients and is Associated with Mitochondrial Membranes", Hum. Mol. Genet. 6(11), 1771-1780 (1997).
Campuzano, et al., "Friedreich's ataxia: autosomal recessive disease caused by an intronic GAA triplet repeat expansion", Science 271(5254), 1423-1427 (1996).
Castilho, et al., "Oxidative Damage of Mitochondria Induced by Fe(II)Citrate Is Potentiated by Ca2+ and Includes Lipid Peroxidation and Alterations in Membrane Proteins", Arch Biochem Biophys 308(1), 158-163 (1994).
Chevalier, et al., "Optimization of pyrimidinol antioxidants as mitochondrial protective agents: ATP production and metabolic stability", Bioorganic & Medicinal Chemistry 24,5206-5220 (2016).
Chua, et al., "Oltipraz-induced phase 2 enzyme response conserved in cells lacking mitochondrial DNA", Biochem Biophys Res Commun 337(1), 375-381 (2005).
Chung, et al., "New 4-hydroxypyridine and 4-hydroxyquinoline derivatives as inhibitors of NADH-ubiquinone reductase in the respiratory chain", Z Naturforsch C 44(7-8), 609-616 (1989).
Corey, et al., "New and highly effective method for the oxidation of primary and secondary alcohols to carbonyl compounds", J Am Chem Soc 94(21), 7586-7587 (1972).
Corey, et al., "Pyridinium chlorochromate. An efficient reagent for oxidation of primary and secondary alcohols to carbonyl compounds", Tetrahedron Leff 16(31), 2647-2650 (1975).
Crompton, "The mitochondrial permeability transition pore and its role in cell death", Biochem J 341(2), 233-249 (1999).
D'Alessio, et al., "Apoptotic GSH extrusion is associated with free radical generation", Ann N Y Acad Sci 1010(1), 449-452 (2003).
De Hingh, et al., "Direct measurement of lipid peroxidation in submitochondrial particles", Biochemistry 34(39), 12755-12760 (1995).
Dimauro, et al., "Mitochondrial disorders in the nervous system", Annu Rev Neurosci 31, 91-123 (2008).
Dimauro, et al., "Mitochondrial DNA mutations in human disease", Am. J. Med Genet. 106(1), 18-26 (2001).
Droge, "Free Radicals in the Physiological Control of Cell Function", Physiol Rev 82(1), 47-95 (2002).
Drummen, et al., "C11-BODIPY(581/591), an oxidation-sensitive fluorescent lipid peroxidation probe: (micro) spectroscopic characterization and validation of methodology", Free Radic. Biol. Med 33(4), 473-490 (2002).
Durr, et al., "Clinical and genetic abnormalities in patients with Friedreich's ataxia", N Engl J Med 335(16), 1169-1175 (1996).
Ehrenberg, et al., "Membrane potential can be determined in individual cells from the nernstian distribution of cationic dyes", Biophy J 53, 785-794 (1988).
Fash, "Effects of alkyl side chain modification of coenzyme Q10 on mitochondrial respiratory chain function and cytoprotection", Bioorg Med Chem 21(8), 2346-2354 (2013).
Finkel, "Oxidant signals and oxidative stress", Cliff Opin Cell Biol 15(2), 247-254 (2003).
Fiore, et al., "The mitochondrial ADP/ATP carrier: Structural, physiological and pathological aspects", Biochimie 80 (2), 137-150 (1998).
Fisher, et al., "The Structure of Isomaltol", J Org Chem 29(4), 776-781 (1964).
Fridovich, "Fundamental aspects of reactive oxygen species, or what's the matter with oxygen?", Ann N Y Acad Sci 893(1), 13-18 (1999).
Frigerio, et al., "A User-Friendly Entry to 2-Iodoxybenzoic Acid (IBX)", J Org Chem 64(12), 4537-4538 (1999).
Gaetani, "Catalase and glutathione peroxidase are equally active in detoxification of hydrogen peroxide in human erythrocytes", Blood 73, 334-339 (1989).
Garcia-Rivas, "Ru360, a specific mitochondrial calcium uptake inhibitor, improves cardiac post-ischaemic functional recovery in rats in vivo", Br J Pharmacol 149(7), 829-837 (2006).
Genova, et al., "Mitochondrial production of oxygen radical species and the role of Coenzyme Q as an antioxidant", Exp Biol Med 228(5), 506-513 (2003).
Gille, et al., "Redox-interaction of alpha-tocopheryl quinone with isolated mitochondrial cytochrome bc1 complex", Biochem Pharmacol 68(2), 373-381 (2004).
Gillis, et al., "Idebenone. A review of its pharmacodynamic and pharmacokinetic properties, and therapeutic use in age-related cognitive disorders", Drugs Aging 5(2), 133-152 (1994).
Goda, et al., "Clinical improvement after administration of coenzyme Q10 in a patient with mitochondrial encephalomyopathy", J Neurol 234(2), 62-63 (1987).
Gold, et al., "Phosphorus magnetic resonance spectroscopy in the evaluation of mitochondrial myopathies: results of a 6-month therapy study with coenzyme Q", Eur Neurol 36(4), 191-196 (1996).
Goldschmidt, et al., "Effects of cytoprotective antioxidants on lymphocytes from representative mitochondrial neurodegenerative diseases", Bioorg. Med. Chem. 21, 969-978 (2013).
Gonzalez-Cabo, et al., "Frataxin interacts functionally with mitochondrial electron transport chain proteins", Hum. Mol. Genet. 14(15), 2091-2098 (2005).
Graier, et al., "Mitochondria and Ca(2+) signaling: old guests, new functions", Eur J Physiol 455, 375-396 (2007).

(56) References Cited

OTHER PUBLICATIONS

Green, et al., "Mitochondria and Apoptosis", Science 281(5381), 1309-1312 (1998).
Gregor, et al., "Distribution of tocopheryl quinone in mitochondrial membranes and interference with ubiquinone-mediated electron transfer", Biochem Pharmacol 71(11), 1589-1601 (2006).
Griffith, et al., "Potent and specific inhibition of glutathione synthesis by buthionine sulfoximine (S-n-butyl homocysteine sulfoximine)", J. Biol. Chem. 254(16), 7558-7560 (1979).
Harris, et al., "Structure of Vitamin B6. II", J Am Chem Soc 61(5), 1242-1244 (1939).
Hart, et al., "Antioxidant treatment of patients with Friedreich ataxia: four-year follow-up", Arch Neurol 62(4), 621-626 (2005).
Henze, et al., "Evolutionary biology: essence of mitochondria", Nature 426, 127-128 (2003).
Ihara, et al., "Mitochondrial encephalomyopathy (MELAS): pathological study and successful therapy with coenzyme Q10 and idebenone", J Neurol Sci 90(3), 263-271 (1989).
Ikejiri, et al., "Idebenone improves cerebral mitochondrial oxidative metabolism in a patient with MELAS", Neurology 47(2), 583-585 (1996).
Infante, et al., "A function for the vitamin E metabolite alpha-tocopherol quinone as an essential enzyme cofactor for the mitochondrial fatty acid desaturases", FEBS Lett 446(1), 1-4 (1999).
Ingold, et al., "A new vitamin E analogue more active than alpha-tocopherol in the rat curative myopathy bioassay", FEBS Lett 205(1), 117-120 (1986).
Inoue, et al., "Improved general method of ortho alkylation of phenols using alkyl isopropyl sulfide, sulfuryl chloride, and triethylamine. An expedient synthesis of representative oxygen heterocycles and (2R,4'R,8'R)-.alpha.-tocopherol", J Org Chem 52(24), 5495-5497 (1987).
Itoh, et al., "The substitution of 5-halo-1,2,3-triazines with electrolytically generated superoxide", Tetrahedron 47(25), 4317-4324 (1991).
Iuliano, et al., "Protection of low density lipoprotein oxidation by the antioxidant agent IRFI005, a new synthetic hydrophilic vitamin E analogue", Free Radic Biol Med 26(7-8), 858-868 (1999).
James, et al., "Interactions of Mitochondria-targeted and Untargeted Ubiquinones with the Mitochondrial Respiratory Chain and Reactive Oxygen Species: Implications for the use of exogenous ubiquinones as therapies and experimental tools", J. Biol. Chem. 280(22), 21295-21312 (2005).
Jauslin, et al., "A cellular model for Friedreich Ataxia reveals small-molecule glutathione peroxidase mimetics as novel treatment strategy", Hum. Mol. Genet. 11(24), 3055-3063 (2002).
Jefferson, et al., "Biaryl guanidine inhibitors of in vitro HCV-IRES activity", Bioorganic Med Chem Lett 14(20), 5139-5143 (2004).
Jenner, et al., "Oxidative stress in Parkinson's disease", Ann Neurol 53(Suppl. 3), S26-S38 (2003).
Joshi, et al., "Benzoquinoa Derivatives. Part I. Reactions of Primary Aliphatic Amines with Embelin (2,5-Dihydroxy-3-undecyl-1,4-benzoquinone) and Di-O-methylembelin", Journal of the Chemical Society, Perkins Transactions 1: Organic and Bio-Organic Chemistry, vol. 4, pp. 327-332 (1975).
Jurma, et al., "Decreased glutathione results in calcium-mediated cell death in PC12", Free Radic Biol Med 23(7), 1055-1066 (1997).
Kamal-Eldin, et al., "The chemistry and antioxidant properties of tocopherols and tocotrienols", Lipids 31(7), 671-710 (1996).
Kao, et al., "Chapter 5—Practical Aspects of Measuring Intracellular Calcium Signals with Fluorescent Indicators", Methods Cell Biol 40, 155-181 (1994).
Katafias, et al., "Oxidation of phenothiazine dyes by manganese(III) in sulfuric acid solution", Transition Met Chem 36(8), 801-809 (2011).
Katsuki, et al., "The first practical method for asymmetric epoxidation", J Am Chem Soc 102(18), 5974-5976 (1980).
Kelso, et al., "Selective targeting of a redox-active ubiquinone to mitochondria within cells: antioxidant and antiapoptotic properties", J Biol Chem 276(7), 4588-4596 (2001, available online 2000).
Khdour, et al., "An acetate prodrug of a pyridinol-based vitamin E analogue", Pharm. Res 28(11), 2896-2909 (2011).
Khdour, et al., "An Optimized Pyrimidinol Multifunctional Radical Quencher", ACS Med Chem Lett 4(8), 724-729 (2013).
Kim, et al., "Efficient Synthesis of 4,5,6-Trisubstituted-2-aminopyrimidines", Bull Korean Chem Soc 30(9), 2107-2110 (2009).
Kim, et al., "Lipid-Soluble 3-Pyridinol Antioxidants Spare α-Tocopherol and Do Not Efficiently Mediate Peroxidation of Cholesterol Esters in Human Low-Density Lipoprotein", J Med Chem 48(22), 6787-6789 (2005).
Kohar, et al., "Is α-tocopherol a reservoir for α-tocopheryl hydroquinone?", Free Radic Biol Med 19(2), 197-207 (1995).
Korytnyk, et al., "On the Inhibitory Activity of 4-Vinyl Analogues of Pyridoxal: Enzyme and Cell Culture Studies", Biochemistry 15(25), 5458-5466 (1976).
Kowaltowski, et al., "Mitochondrial damage induced by conditions of oxidative stress", Free Radic Biol Med 26(3-4), 463-471 (1999).
Kowaltowski, et al., "Mitochondrial permeability transition and oxidative stress", FEBS Lett 495(1-2), 12-15 (2001).
Kowaltowski, et al., "The Thiol-specific Antioxidant Enzyme Prevents Mitochondrial Permeability Transition", J Biol Chem 273(21), 12766-12769 (1998).
Kuypers, et al., "Parinaric acid as a sensitive fluorescent probe for the determination of lipid peroxidation", Biochim Biophys Acta 921(2), 266-274 (1987).
L'Vova, et al., "Heterodiene condensation of 4-methyl-5-propoxyoxazole with vinylethynyldimethylcarbinol", Zhurnal Organicheskoi Khimii 11(7), 1537-1540 (1975).
La Marche, et al., "The Cardiomyopathy of Friedreich's Ataxia Morphological Observations in 3 Cases", Can J Neurosci 7, 389-396 (1980).
Lebel, et al., "Evaluation of the probe 2',7'-dichlorofluorescin as an indicator of reactive oxygen species formation and oxidative stress", Chem Res Toxicol 5(2), 227-231 (1992).

SUBSTITUTED PHENOTHIAZINES AS MITOCHONDRIAL AGENTS

CROSS-REFERENCE TO RELATED APPLICATIONS

This application claims the benefit of the filing dates of U.S. Provisional Patent Application Ser. No. 62/117,205, filed Feb. 17, 2015, which is hereby incorporated by reference in its entirety.

BACKGROUND OF THE INVENTION

Field of the Invention

The present disclosure provides phenothiazine derivative compounds and salts thereof, compositions comprising these compounds, and methods of using these compounds in a variety of applications, such as treatment or suppression of diseases associated with decreased mitochondrial function resulting in diminished ATP production and/or oxidative stress and/or lipid peroxidation.

Description of Related Art

Mitochondria are intracellular organelles responsible for a number of metabolic transformations and regulatory functions. They produce much of the ATP employed by eukaryotic cells. They are also the major source of free radicals and reactive oxygen species that cause oxidative stress. Consequently, mitochondrial defects are damaging, particularly to neural and muscle tissues which have high energy level demands. Thus, energetic defects have been implicated in forms of movement disorders, cardiomyopathy, myopathy, blindness, and deafness (DiMauro et al. (2001) *Am. J. Med. Genet.* 106, 18-26; Leonard et al. (2000) *Lancet.* 355, 299-304). There are a number of mitochondrial diseases resulting from both nuclear and mitochondrial genetic defects, and the underlying biochemistries of these diseases tend to be rather similar. They include increased lactate production, diminished respiration and ATP production, and reflect the consequences of oxidative stress. Mitochondrial dysfunction is linked to numerous neurodegenerative diseases including Alzheimer's disease, Parkinson's disease, Huntington's disease, and Friedreich's ataxia.

SUMMARY OF THE INVENTION

We recognized a need for therapies that target diseases associated with decreased mitochondrial function resulting in diminished ATP production and/or oxidative stress and/or lipid peroxidation. Thus, this disclosure is generally directed describes novel compounds for the treatment or suppression of such diseases. The inventors have found that the compounds of the disclosure confer cytoprotection and quenched ROS and lipid peroxidation in a dose-dependent manner in Friedreich's ataxia (FRDA) lymphocytes at low micromolar concentrations. The compounds of the disclosure also prevent ROS-induced damage of cellular lipid membranes and maintain the mitochondrial membrane potential of FRDA lymphocytes. In addition, the compounds of the disclosure significantly increased frataxin levels. The disclosure also describes use of these compounds for the treatment of mitochondrial disorders, including but not limited to Friedreich's ataxia, Leber's Hereditary Optic Neuropathy, Kearns-Sayre Syndrome, Mitochondrial Encephalomyopathy with Lactic Acidosis and Stroke-Like Episodes and more generally, any disease associated with impairment of energy production and mitochondrial function. Aging may also involve decreased mitochondrial function and diminished ATP production, and the therapeutic agents described here may also find utility in mitigating the effects of aging.

Thus, in one aspect, the disclosure provides a compound of formula (I):

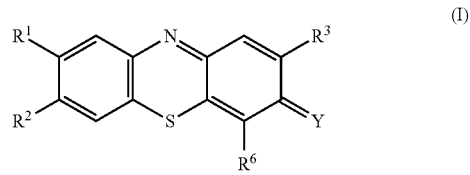

wherein
Y is =O or =N⁺R⁴R⁵X⁻, where X⁻ is a counterion;
$R^1$ is hydrogen, $C_1$-$C_{20}$ alkyl, $C_2$-$C_{20}$ alkenyl, $C_2$-$C_{20}$ alkynyl, —$OR^7$, —$SR^7$, or —$N(R^7)_2$, each optionally substituted with one to four substituents selected from halogen, —CN, —$NO_2$, $C_1$-$C_6$ alkyl, halo($C_1$-$C_6$ alkyl), —$OR^8$, —$NR^8_2$, —$CO_2R^8$, —$CONR^8_2$, $C_3$-$C_8$ cycloalkyl, $C_3$-$C_8$cycloalkenyl, aryl, heteroaryl, and heterocycle, wherein each cycloalkyl, cycloalkenyl, aryl, heteroaryl, and heterocycle are optionally substituted with one or more $R^9$;
  where each $R^7$ independently is hydrogen, $C_1$-$C_6$ alkyl, or halo($C_1$-$C_6$ alkyl);
  where each $R^8$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with one or more $R^9$;
  where each $R^9$ independently is halogen, —CN, —$NO_2$, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$ alkylamino;
$R^2$ is —$N(R^{12})_2$, where $R^{12}$ groups together with the nitrogen to which they are attached form a heterocycle optionally substituted with one or more $R^9$;
$R^3$ is hydrogen, $C_1$-$C_{20}$ alkyl, $C_2$-$C_{20}$ alkenyl, $C_2$-$C_{20}$ alkynyl, or —$OR^7$, each optionally substituted with one to four substituents selected from halogen, —CN, —$NO_2$, $C_1$-$C_6$ alkyl, halo($C_1$-$C_6$ alkyl), —$OR^8$, —$NR^8_2$, —$CO_2R^8$, —$CONR^8_2$, $C_3$-$C_8$ cycloalkyl, $C_3$-$C_8$cycloalkenyl, aryl, heteroaryl, and heterocycle, wherein each cycloalkyl, cycloalkenyl, aryl, heteroaryl, and heterocycle are optionally substituted with $R^9$;
$R^4$ and $R^5$ together with nitrogen to which they are attached form a heterocycle optionally substituted with one or more $R^9$;
each $R^6$ is hydrogen, $C_1$-$C_{20}$ alkyl, $C_2$-$C_{20}$ alkenyl, $C_2$-$C_{20}$ alkynyl, $C_3$-$C_8$ cycloalkyl, $C_3$-$C_8$cycloalkenyl, aryl, heteroaryl, heterocycle, —$OR^{10}$, or —$N(R^{11})_2$, wherein each alkyl, alkenyl, and alkynyl are optionally substituted with one to four substituents selected from halogen, —CN, —$NO_2$, $C_1$-$C_6$ alkyl, halo($C_1$-$C_6$ alkyl), —$OR^8$, —$NR^8_2$, —$CO_2R^8$, —$CONR^8_2$, $C_3$-$C_8$ cycloalkyl optionally substituted with $R^9$, $C_3$-$C_8$ cycloalkenyl optionally substituted with $R^9$, aryl optionally substituted with $R^9$, heteroaryl optionally substituted with $R^9$, and heterocycle optionally substituted with $R^9$;
  where $R^{10}$ is $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^9$; and where each $R^{11}$ independently is hydrogen, $C_1$-$C_{20}$ alkyl, $C_2$-$C_{20}$ alkenyl, or $C_2$-$C_{20}$ alkynyl.

Another aspect of the disclosure provides a compound of formula (II):

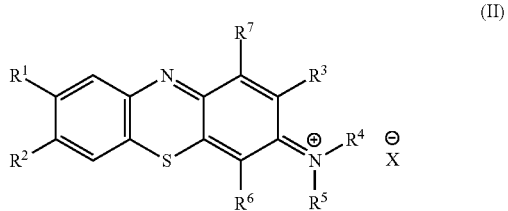

wherein $X^-$ is a counterion;

$R^1$ is hydrogen, $C_1$-$C_{20}$ alkyl, $C_2$-$C_{20}$ alkenyl, $C_2$-$C_{20}$ alkynyl, —$OR^7$, —$SR^7$, —$NHR^7$, or —$N(R^7)_2$, each optionally substituted with one to four substituents selected from halogen, —CN, —$NO_2$, $C_1$-$C_6$ alkyl, halo($C_1$-$C_6$ alkyl), —$OR^8$, —$NR^8{}_2$, —$CO_2R^8$, —$CONR^8{}_2$, $C_3$-$C_8$ cycloalkyl, $C_3$-$C_8$cycloalkenyl, aryl, heteroaryl, and heterocycle, wherein each cycloalkyl, cycloalkenyl, aryl, heteroaryl, and heterocycle are optionally substituted with one or more $R^9$;

where each $R^7$ independently is hydrogen, $C_1$-$C_6$ alkyl, or halo($C_1$-$C_6$ alkyl);

where each $R^8$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with one or more $R^9$;

where each $R^9$ independently is halogen, —CN, —$NO_2$, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;

$R^2$ and $R^6$ are independently —$N(R^{11})_2$;

where each $R^{11}$ independently is hydrogen, $C_1$-$C_{20}$ alkyl, $C_2$-$C_{20}$ alkenyl, or $C_2$-$C_{20}$ alkynyl;

$R^3$ is hydrogen, $C_1$-$C_{20}$ alkyl, $C_2$-$C_{20}$ alkenyl, $C_2$-$C_{20}$ alkynyl, or —$OR^7$, each optionally substituted with one to four substituents selected from halogen, —CN, —$NO_2$, $C_1$-$C_6$ alkyl, halo($C_1$-$C_6$ alkyl), —$OR^8$, —$NR^8{}_2$, —$CO_2R^8$, —$CONR^8{}_2$, $C_3$-$C_8$ cycloalkyl, $C_3$-$C_8$cycloalkenyl, aryl, heteroaryl, and heterocycle, wherein each cycloalkyl, cycloalkenyl, aryl, heteroaryl, and heterocycle are optionally substituted with $R^9$;

$R^4$ and $R^5$ are independently $C_1$-$C_{20}$ alkyl, $C_2$-$C_{20}$ alkenyl, or $C_2$-$C_{20}$ alkynyl, each optionally substituted with one to four substituents selected from halogen, —CN, —$NO_2$, $C_1$-$C_6$ alkyl, halo($C_1$-$C_6$ alkyl), —$OR^8$, —$NR^8{}_2$, —$CO_2R^8$, —$CONR^8{}_2$, $C_3$-$C_8$ cycloalkyl, $C_3$-$C_8$cycloalkenyl, aryl, heteroaryl, and heterocycle, wherein each cycloalkyl, cycloalkenyl, aryl, heteroaryl, and heterocycle are optionally substituted with $R^9$;

where $R^{10}$ is $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^9$; and $R^7$ is hydrogen or —$N(R^{11})_2$.

Another aspect of the disclosure provides pharmaceutical compositions comprising the compounds and salts of the disclosure and an appropriate carrier, excipient or diluent. The exact nature of the carrier, excipient or diluent will depend upon the desired use for the composition, and may range from being suitable for veterinary uses to being suitable for human use. The compositions may optionally include one or more additional compounds suitable for a use.

Another aspect of the disclosure provides methods of treating or suppressing diseases associated with decreased mitochondrial function resulting in diminished ATP production and/or oxidative stress and/or lipid peroxidation, comprising administering an effective amount of the compound and salts of the disclosure.

Another aspect of the disclosure provides a method of treating or suppressing one or more of Friedreich's ataxia, Leber's Hereditary Optic Neuropathy, Kearns-Sayre Syndrome, Mitochondrial Encephalomyopathy with Lactic Acidosis and Stroke-Like Episodes, or Leigh syndrome, comprising administering an effective amount of the compound and salts of the disclosure.

Another aspect of the disclosure provides a method of treating or suppressing one or more of obesity, atherosclerosis, amyotrophic lateral sclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, and Leigh syndrome, comprising administering an effective amount of the compound and salts of the disclosure.

DESCRIPTION OF DRAWINGS

The results set forth herein, and the properties and characteristics of the compounds provided by the disclosure, can be advantageously understood with regard to the drawings.

DETAILED DESCRIPTION OF THE INVENTION

Figure 1:
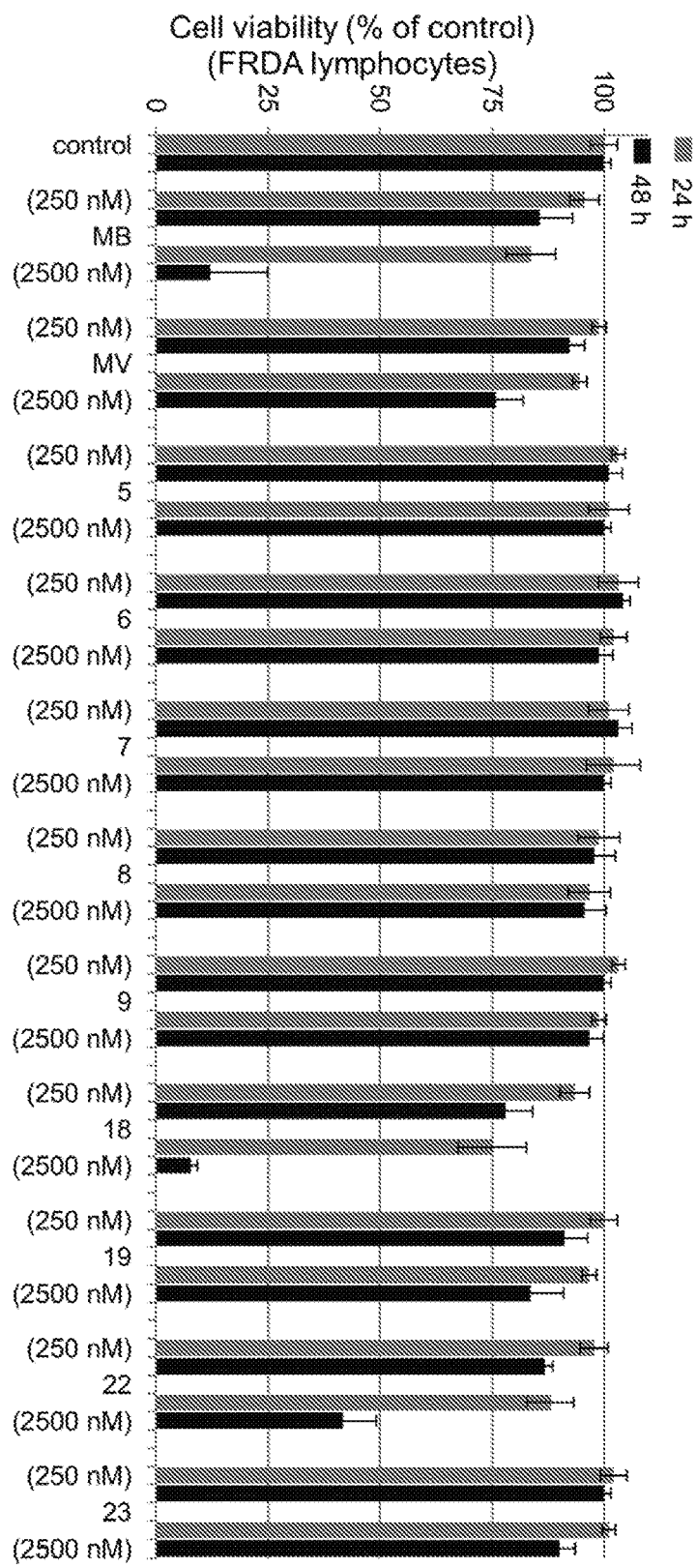
FIG. 1 shows the results of effect of the compounds of the disclosure on cytotoxicity. Cultured FRDA lymphocytes were incubated for 24 h or 48 h in glucose free media (galactose) to force cells to rely on mitochondria to produce their ATP. Flow cytometric determination of cell viability by fluorescence labeling was used employing calcein acetoxymethyl-ester and ethidium homodimer-1 as live and dead cell stains. MB is methylene blue (3,7-bis(dimethylamino) phenazathionium chloride); MV is methylene violet (7-(dimethylamino)-3H-phenothiazin-3-one).
Figure 2:
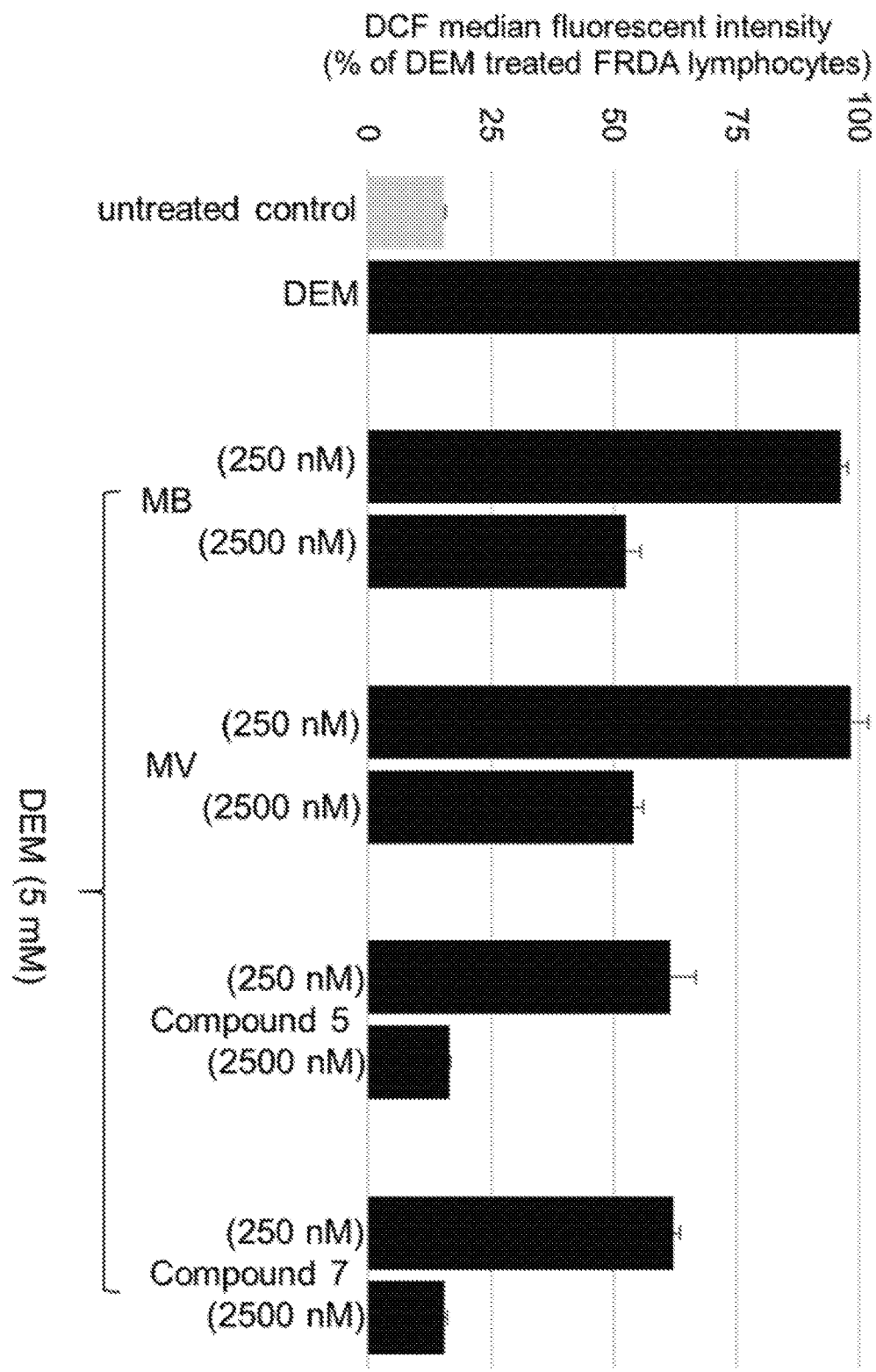
FIG. 2 shows flow cytometric analysis of FRDA lymphocyte cells stained with dichlorodihydrofluorescein diacetate (DCFH-DA) for 20 min, following pretreatment with the test compounds for 16 h, and subsequent treatment with diethyl maleate (DEM) for 80 min to induce the production of reactive oxygen species (ROS) by depleting glutathione level.
Figure 3:
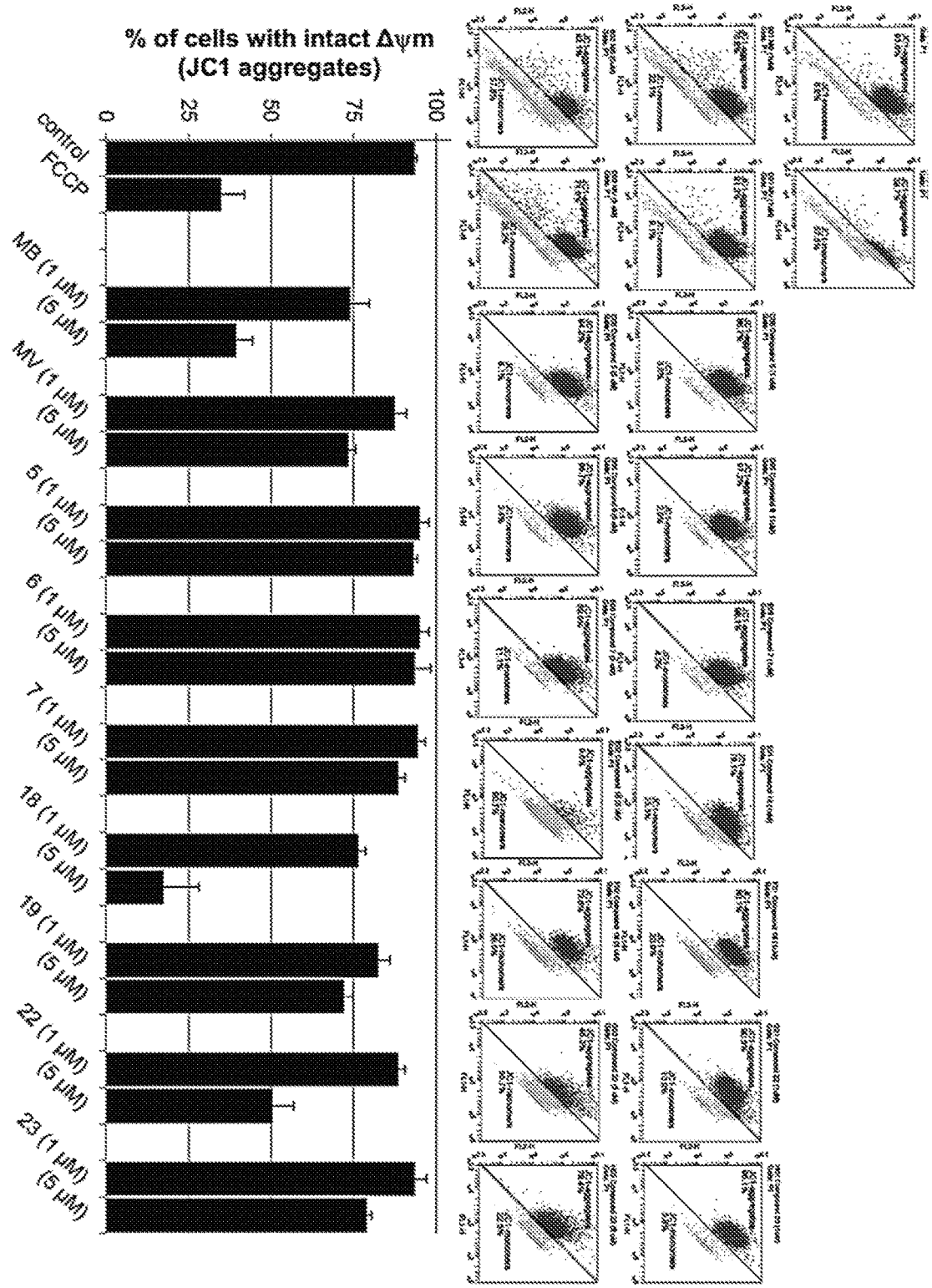
FIG. 3 shows flow cytometric analysis shows the effect of test compounds on $\Delta\psi_m$ in FRDA lymphocyte cells using the ratiometric fluorescent probe JC-1. This probe is a cell penetrating dye that accumulates within mitochondria maintaining high $\Delta\psi_m$. Dark gray regions represent intact mitochondrial membranes with JC-1 aggregates (red fluorescence), whereas the gated region in light gray depicts cells with loss of $\Delta\psi_m$. The bar graph shows the percentage of cells with intact $\Delta\psi_m$ calculated using Accuri™ C6 software. In each analysis, 10000 events were recorded. Depolarization with carbonyl cyanide p-(trifluoromethoxy)phenylhydrazone (FCCP), was used to serve as a positive control.
Figure 4:
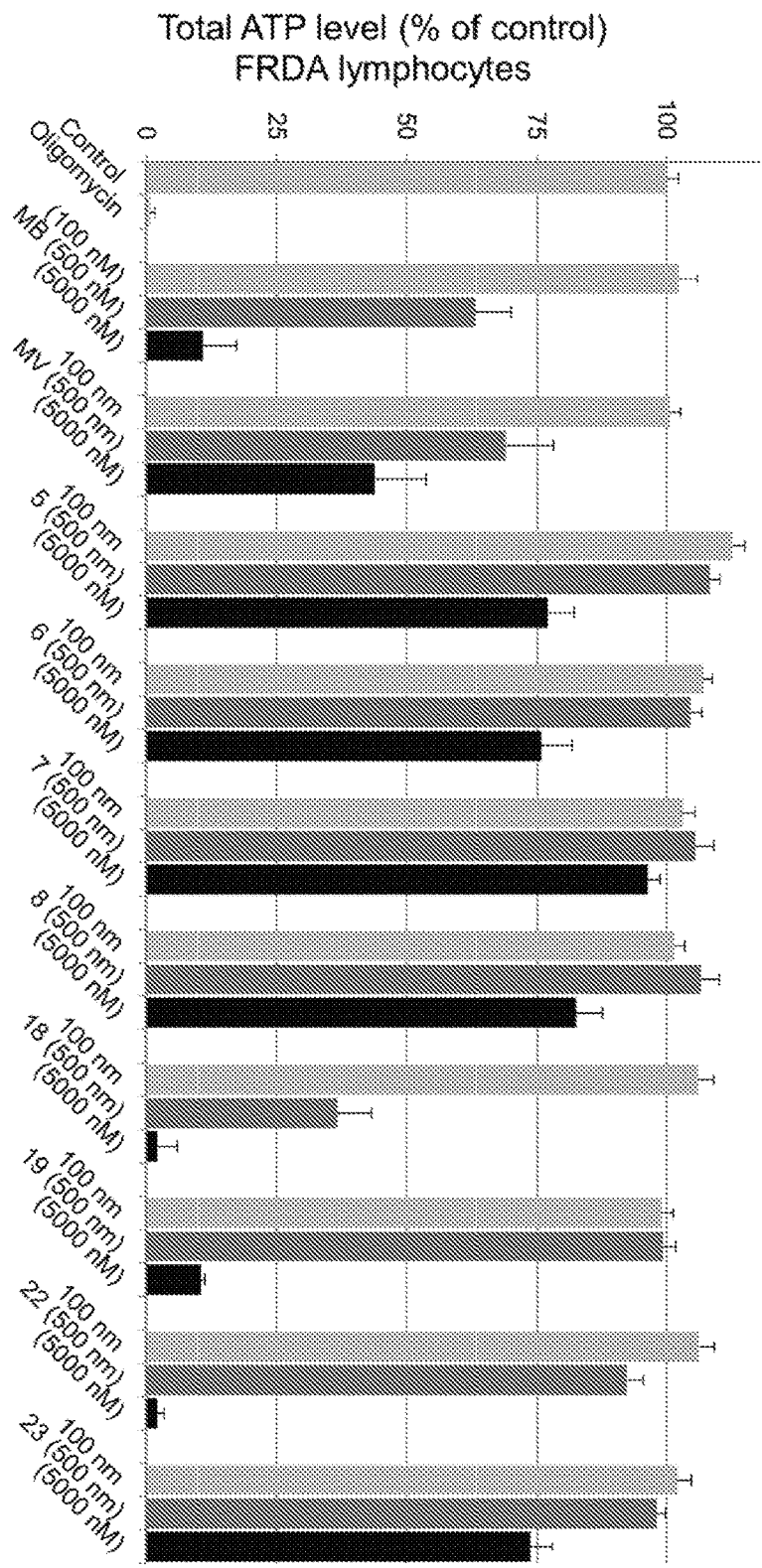
FIG. 4 shows total ATP level in FRDA lymphocytes following incubation with test compounds for 24 h in glucose free media (25 mM galactose). Results are expressed as percentage of total ATP relative to untreated control.
Figure 5:
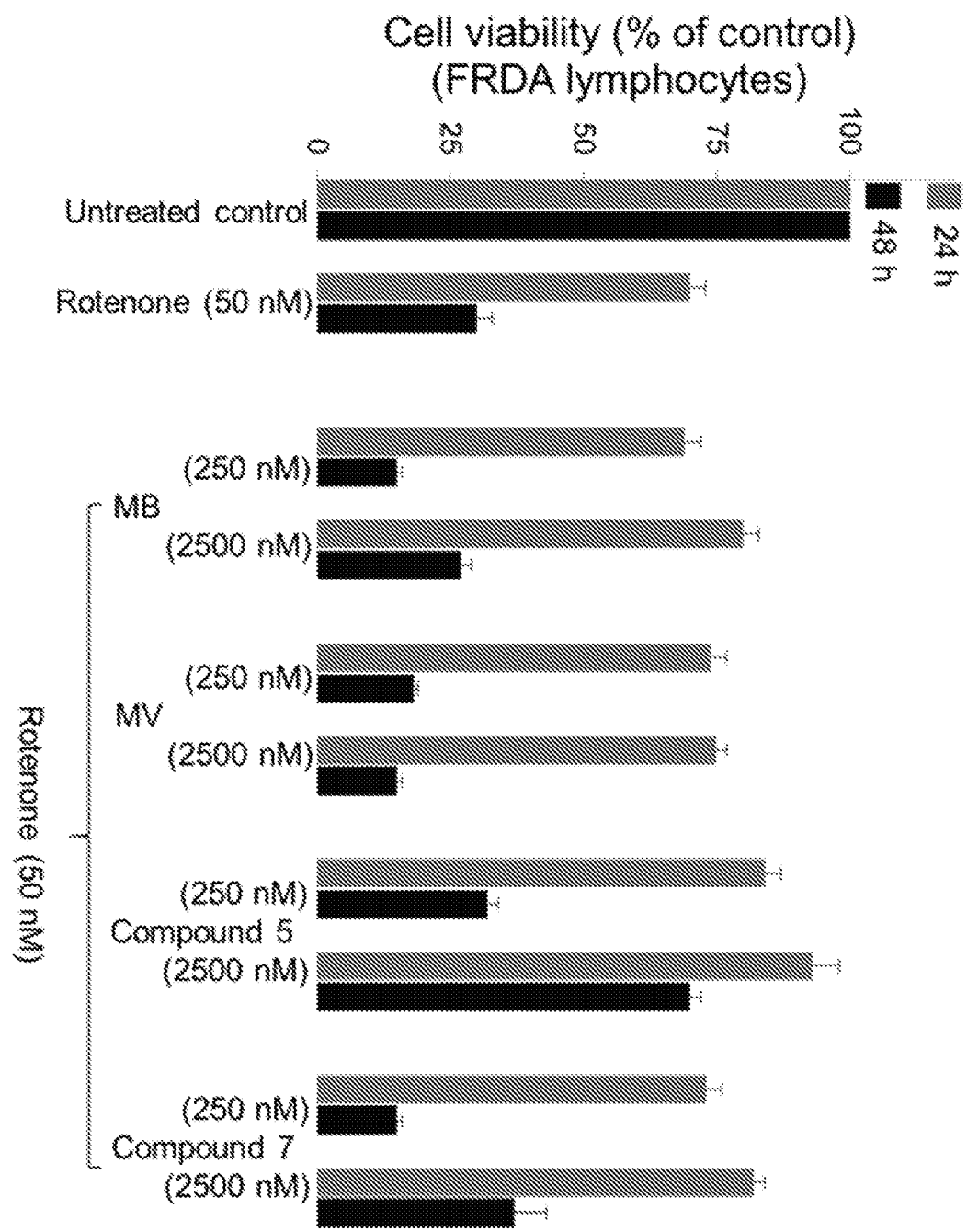
FIG. 5 illustrates cytoprotective effect of the test compounds in FRDA lymphocytes following preincubation with test compounds for 4 h in glucose free media and subsequent treatment with rotenone (50 nM) for 24 h or 48 h to inhibit complex I. Cell viability was measured by flow cytometry using fluorescence labeling with calcein acetoxy-methylester and ethidium homodimer-1 as live and dead cell stains, respectively. Results are expressed as percentage live cells relative to untreated control.
Figure 6:
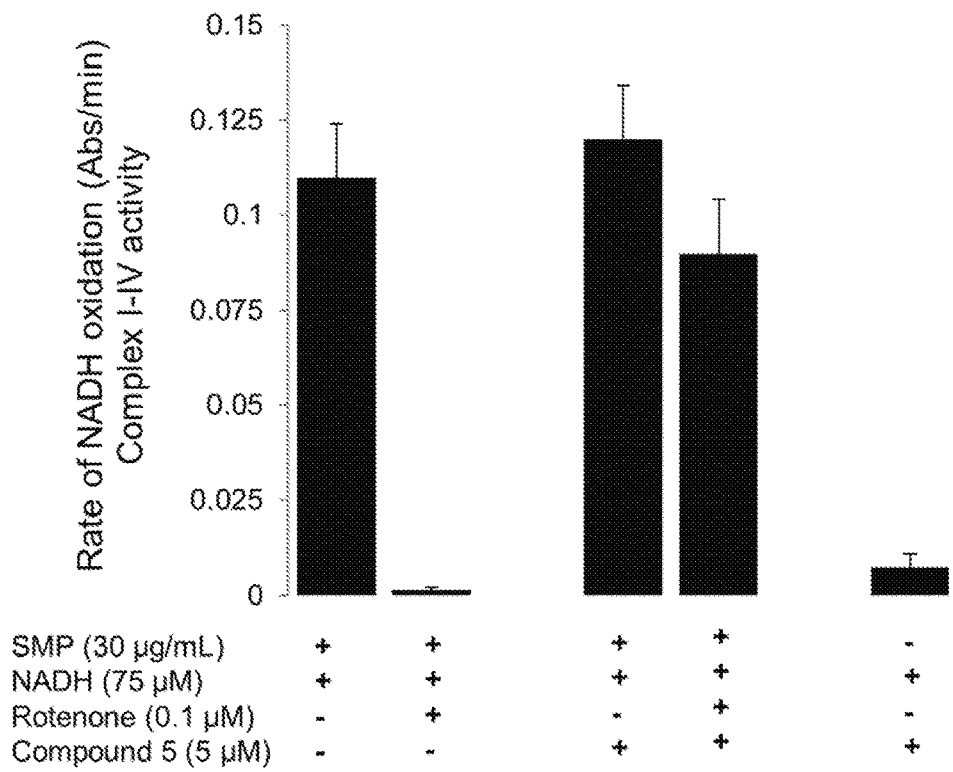
FIG. 6 shows the effect of compound 5 on bovine heart mitochondrial NADH oxidase activity (complexes I, III and IV) (NADH oxidase). Compound 5 was able redirect electron flow in the respiratory chain as a result of NADH oxidation even in complex I completely blocked by rotenone.
Figure 7:
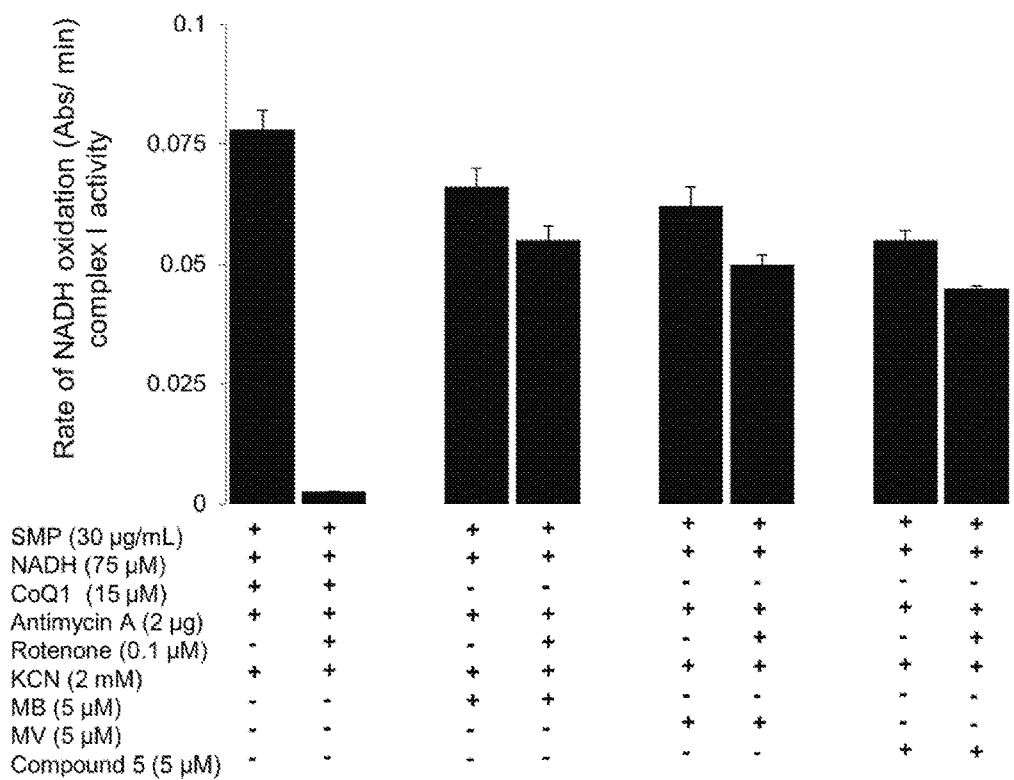
FIG. 7 shows bovine heart mitochondrial complex I (SMP) activity in presence of a number of the test compounds.
Figure 8:
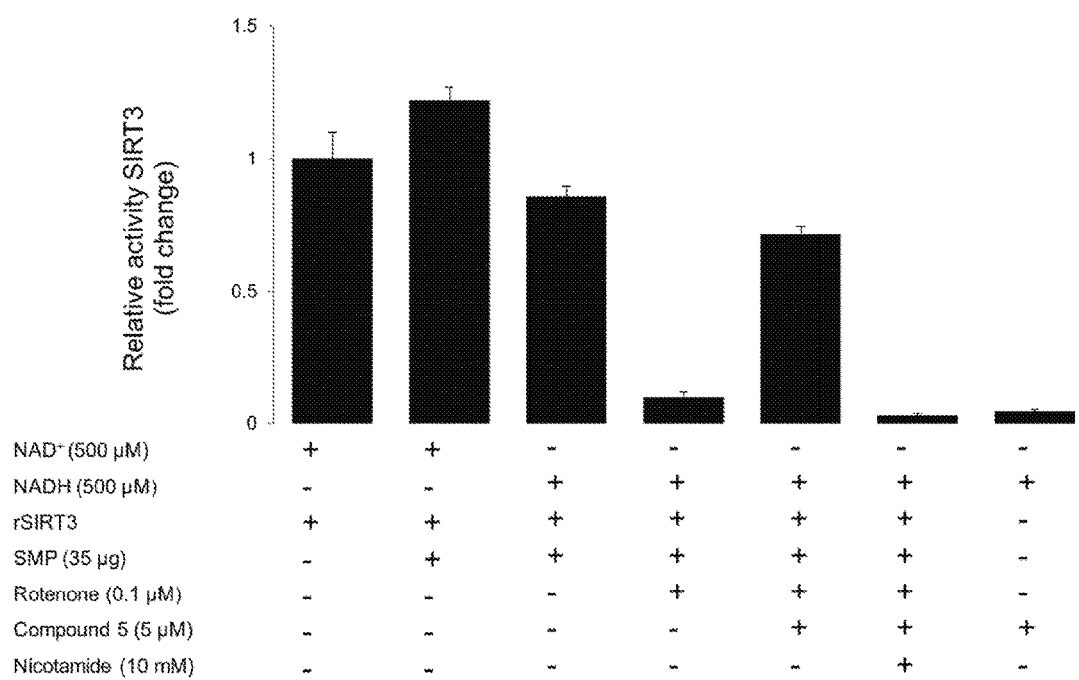
FIG. 8 illustrates in vitro SIRT3 deacetylation activity, complex I activity in bovine heart submitochondrial particles (SMP) was coupled with recombinant SIRT3 (rSIRT3) activity using a luminogenic acetylated SIRT3 peptide substrate. The co-substrate $NAD^+$ was generated from oxidation of NADH by complex I in presence and absence of rotenone.
Figure 9:
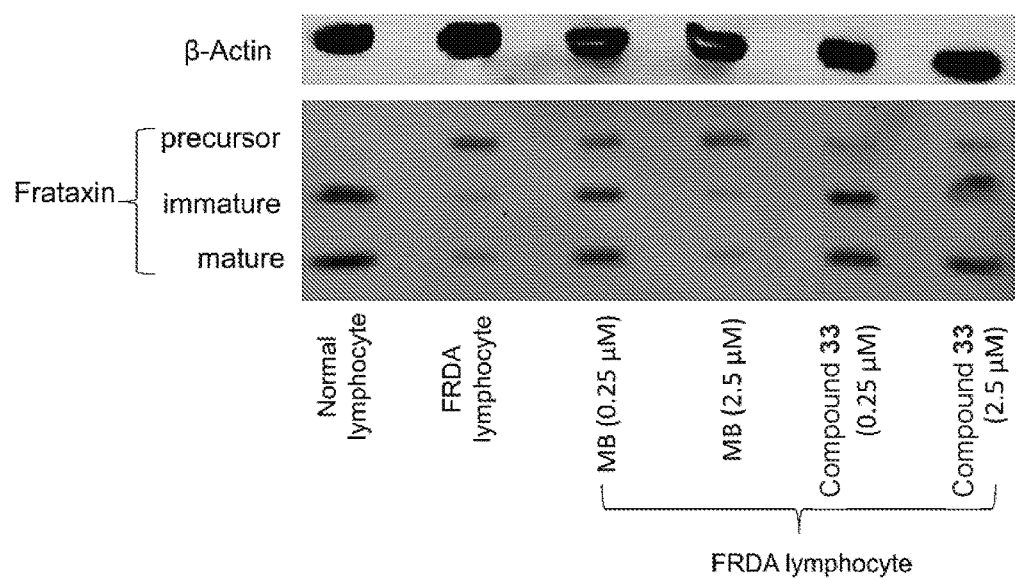
FIG. 9 illustrates western blot showing the effect of MB and its analogue compound 33 on the level of frataxin in FRDA lymphocytes. Methylene blue slightly increased frataxin at lower concentration but did not at higher concentration. The modified analogue compound 33 significantly increased frataxin levels at both concentrations.

Before the disclosed methods are described, it is to be understood that the aspects described herein are not limited to specific embodiments, or compositions, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

In view of the present disclosure, the compositions and methods described herein can be configured by the person of ordinary skill in the art to meet the desired need. In general, the disclosed compounds and methods provide improvements in the treatment of diseases associated with decreased mitochondrial function resulting in diminished ATP production and/or oxidative stress and/or lipid peroxidation. For example, in particular embodiments, the compounds of the disclosure confer cytoprotection and quenched ROS and lipid peroxidation in a dose-dependent manner in Friedreich's ataxia (FRDA) lymphocytes at low micromolar concentrations. The compounds of the disclosure also prevent ROS-induced damage of cellular lipid membranes and maintain the mitochondrial membrane potential of FRDA lymphocytes. The compounds of the disclosure (for example, compound 33) also significantly increased frataxin levels.

In one aspect, the disclosure provides a compound of formula (I):

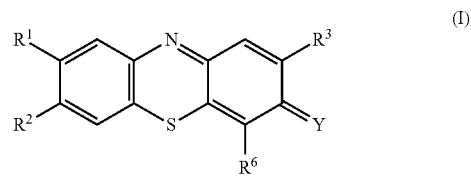

wherein
Y is =O or $=N^+R^4R^5X^-$, where $X^-$ is a counterion;
$R^1$ is hydrogen, $C_1$-$C_{20}$ alkyl, $C_2$-$C_{20}$ alkenyl, $C_2$-$C_{20}$ alkynyl, $-OR^7$, $-SR^7$, or $-N(R^7)_2$, each optionally substituted with one to four substituents selected from halogen, $-CN$, $-NO_2$, $C_1$-$C_6$ alkyl, halo($C_1$-$C_6$ alkyl), $-OR^8$, $-NR^8_2$, $-CO_2R^8$, $-CONR^8_2$, $C_3$-$C_8$ cycloalkyl, $C_3$-$C_8$cycloalkenyl, aryl, heteroaryl, and heterocycle, wherein each cycloalkyl, cycloalkenyl, aryl, heteroaryl, and heterocycle are optionally substituted with one or more $R^9$;
where each $R^7$ independently is hydrogen, $C_1$-$C_6$ alkyl, or halo($C_1$-$C_6$ alkyl);
where each $R^8$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with one or more $R^9$;
where each $R^9$ independently is halogen, $-CN$, $-NO_2$, $-N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;
$R^2$ is $-N(R^{12})_2$, where $R^{12}$ groups together with the nitrogen to which they are attached form a heterocycle optionally substituted with one or more $R^9$;
$R^3$ is hydrogen, $C_1$-$C_{20}$ alkyl, $C_2$-$C_{20}$ alkenyl, $C_2$-$C_{20}$ alkynyl, or $-OR^7$, each optionally substituted with one to four substituents selected from halogen, $-CN$, $-NO_2$, $C_1$-$C_6$ alkyl, halo($C_1$-$C_6$ alkyl), $-OR^8$, $-NR^8_2$, $-CO_2R^8$, $-CONR^8_2$, $C_3$-$C_8$ cycloalkyl, $C_3$-$C_8$cycloalkenyl, aryl, heteroaryl, and heterocycle, wherein each cycloalkyl, cycloalkenyl, aryl, heteroaryl, and heterocycle are optionally substituted with $R^9$;
$R^4$ and $R^5$ together with nitrogen to which they are attached form a heterocycle optionally substituted with one or more $R^9$;
each $R^6$ is hydrogen, $C_1$-$C_{20}$ alkyl, $C_2$-$C_{20}$ alkenyl, $C_2$-$C_{20}$ alkynyl, $C_3$-$C_8$ cycloalkyl, $C_3$-$C_8$cycloalkenyl, aryl, heteroaryl, heterocycle, $-OR^{10}$, or $-N(R^{11})_2$, wherein each alkyl, alkenyl, and alkynyl are optionally substituted with one to four substituents selected from halogen, $-CN$, $-NO_2$, $C_1$-$C_6$ alkyl, halo($C_1$-$C_6$ alkyl), $-OR^8$, $-NR^8_2$, $-CO_2R^8$, $-CONR^8_2$, $C_3$-$C_8$ cycloalkyl optionally substituted with $R^9$, $C_3$-$C_8$ cycloalkenyl optionally substituted with $R^9$, aryl optionally substituted with $R^9$, heteroaryl optionally substituted with $R^9$, and heterocycle optionally substituted with $R^9$;
where $R^{10}$ is $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^9$; and where each $R^{11}$ independently is hydrogen, $C_1$-$C_{20}$ alkyl, $C_2$-$C_{20}$ alkenyl, or $C_2$-$C_{20}$ alkynyl.

In one embodiment, the disclosure provides compounds of formula (I), wherein $R^1$ is hydrogen, optionally substituted $C_1$-$C_{20}$ alkyl, optionally substituted $C_2$-$C_{20}$ alkenyl, optionally substituted $C_2$-$C_{20}$ alkynyl, or —$OR^7$. In some embodiments, $R^1$ is hydrogen. In some other embodiments, $R^1$ is optionally substituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In some embodiments, $R^1$ is $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl), wherein the alkyl is optionally substituted with —$OR^8$, $C_3$-$C_8$ cycloalkyl, $C_3$-$C_8$cycloalkenyl, or aryl, wherein each cycloalkyl, cycloalkenyl, and aryl are optionally substituted with $R^9$. In one embodiment, $R^1$ is $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl), wherein the alkyl is optionally substituted with $C_3$-$C_8$ cycloalkyl, $C_3$-$C_8$cycloalkenyl, or aryl, wherein each cycloalkyl, cycloalkenyl, and aryl are optionally substituted with $R^9$. In another embodiment, $R^1$ is —$OR^7$ and $R^7$ is $C_1$-$C_6$ alkyl.

In another embodiment, the disclosure provides compounds of formula (I), wherein $R^2$ is piperazinyl, piperidinyl, morpholinyl, pyrrolidinyl, azepanyl, or diazepanyl, each optionally substituted with one or more $R^9$. In one embodiment, $R^2$ is piperidinyl optionally substituted with one or more $R^9$. In another embodiment, $R^2$ is unsubstituted piperidinyl. In one embodiment, $R^2$ is morpholinyl optionally substituted with one or more $R^9$. In another embodiment, $R^2$ is unsubstituted morpholinyl.

In one embodiment, the disclosure provides compounds as described above with any reference to formula (I), wherein $R^3$ is hydrogen, optionally substituted $C_1$-$C_{20}$ alkyl, or —$OR^7$. In another embodiment, $R^3$ is hydrogen.

In one embodiment, the disclosure provides compounds as described above with any reference to formula (I), wherein $R^3$ is optionally substituted $C_1$-$C_{20}$ alkyl. In one embodiment, $R^3$ is $C_1$-$C_{20}$ alkyl optionally substituted with —$OR^8$, $C_3$-$C_8$ cycloalkyl, $C_3$-$C_8$cycloalkenyl, or aryl, wherein each cycloalkyl, cycloalkenyl, and aryl are optionally substituted with $R^9$. In another embodiment, $R^3$ is $C_1$-$C_{20}$ alkyl optionally substituted with $C_3$-$C_8$ cycloalkyl, $C_3$-$C_8$cycloalkenyl, or aryl, wherein each cycloalkyl, cycloalkenyl, and aryl are optionally substituted with $R^9$. In yet another embodiment, $R^3$ is unsubstituted $C_1$-$C_{20}$ alkyl.

In one embodiment, the disclosure provides compounds as described above with any reference to formula (I), wherein $R^3$ is optionally substituted $C_3$-$C_{20}$ alkyl, or $R^3$ is optionally substituted $C_4$-$C_{20}$ alkyl, or $R^3$ is optionally substituted $C_5$-$C_{20}$ alkyl. In one embodiment, $R^3$ is $C_5$-$C_{20}$ alkyl optionally substituted with —$OR^8$, $C_3$-$C_8$ cycloalkyl, $C_3$-$C_8$cycloalkenyl, or aryl, wherein each cycloalkyl, cycloalkenyl, and aryl are optionally substituted with $R^9$. In another embodiment, $R^3$ is $C_5$-$C_{20}$ alkyl optionally substituted with $C_3$-$C_8$ cycloalkyl, $C_3$-$C_8$cycloalkenyl, or aryl, wherein each cycloalkyl, cycloalkenyl, and aryl are optionally substituted with $R^9$. In one embodiment, $R^3$ is unsubstituted $C_3$-$C_{20}$ alkyl, or $R^3$ is unsubstituted $C_4$-$C_{20}$ alkyl, or $R^3$ is unsubstituted $C_5$-$C_{20}$ alkyl.

In one embodiment, the disclosure provides compounds as described above with any reference to formula (I), wherein $R^3$ is optionally substituted $C_6$-$C_{20}$ alkyl, or $R^3$ is optionally substituted $C_7$-$C_{20}$ alkyl, or $R^3$ is optionally substituted $C_8$-$C_{20}$ alkyl. In one embodiment, $R^3$ is $C_7$-$C_{20}$ alkyl optionally substituted with —$OR^8$, $C_3$-$C_8$ cycloalkyl, $C_3$-$C_8$cycloalkenyl, or aryl, wherein each cycloalkyl, cycloalkenyl, and aryl are optionally substituted with $R^9$. In another embodiment, $R^3$ is $C_7$-$C_{20}$ alkyl optionally substituted with $C_3$-$C_8$ cycloalkyl, $C_3$-$C_8$cycloalkenyl, or aryl, wherein each cycloalkyl, cycloalkenyl, and aryl are optionally substituted with $R^9$. In yet another embodiment, $R^3$ is unsubstituted $C_6$-$C_{20}$ alkyl, $R^3$ is unsubstituted $C_7$-$C_{20}$ alkyl, or $R^3$ is unsubstituted $C_8$-$C_{20}$ alkyl.

In one embodiment, the compounds of formula (I) are those wherein $R^3$ is $C_{10}$-$C_{20}$ alkyl optionally substituted with —$OR^8$, $C_3$-$C_8$ cycloalkyl, $C_3$-$C_8$cycloalkenyl, or aryl, wherein each cycloalkyl, cycloalkenyl, and aryl are optionally substituted with $R^9$. In one embodiment, $R^3$ is $C_{10}$-$C_{20}$ alkyl optionally substituted with $C_3$-$C_8$ cycloalkyl, $C_3$-$C_8$cycloalkenyl, or aryl, wherein each cycloalkyl, cycloalkenyl, and aryl are optionally substituted with $R^9$. In another embodiment, $R^3$ is unsubstituted $C_{10}$-$C_{20}$ alkyl. In yet another embodiment, $R^3$ is heptadecyl.

In one embodiment, the disclosure provides compounds as described above with any reference to formula (I), wherein $R^3$ is —$OR^7$ and $R^7$ is $C_1$-$C_6$ alkyl.

In another embodiment, the disclosure provides compounds as described above with any reference to formula (I), wherein Y is =O.

In another embodiment, the disclosure provides compounds as described above with any reference to formula (I), wherein Y is =$N^+R^4R^5X^-$. In one embodiment, $X^-$ is a counterion. Counterions may include inorganic or organic counterions. Inorganic counterions include, by way of example and not limitation, halide (e.g., chloride, bromide, iodide, etc.), sulfate, nitrate, phosphate, hydroxide, oxide, and the like. Organic counterions include, by way of example and not limitation, acetate, monofluoroacetate, difluoroacetate, trifluoroacetate, propionate, hexanoate, cyclopentanepropionate, glycolate, oxalate, pyruvate, lactate, malonate, succinate, malate, maleate, fumarate, tartarate, citrate, palmitate, benzoate, 3-(4-hydroxybenzoyl)benzoate, cinnamate, mandelate, alkylsulfonates (e.g., methanesulfonate, ethanesulfonate, 1,2-ethane-disulfonate, 2-hydroxyethanesulfonate, etc.), arylsulfonates (e.g., benzenesulfonate, 4-chlorobenzenesulfonate, 2-naphthalenesulfonate, 4-toluenesulfonate, camphorsulfonate, etc.), 4-methylbicyclo[2.2.2]-oct-2-ene-1-carboxylate, glucoheptonate, 3-phenylpropionate, trimethylacetate, tertiary butylacetate, lauryl sulfurate, gluconate, glutamate, hydroxynaphthoate, salicylate, stearate, muconate, and the like. In one embodiment, $X^-$ is halogen. In another embodiment, $X^-$ is $I^-$.

In one embodiment, the compounds of formula (I) are those wherein $R^4$ is optionally substituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In another embodiment, $R^4$ is $C_1$-$C_6$ alkyl.

In one embodiment, the compounds of formula (I) are those wherein $R^5$ is optionally substituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In another embodiment, $R^5$ is $C_1$-$C_6$ alkyl.

In one embodiment, the disclosure provides compounds of formula (I), wherein $R^4$ and $R^5$ together with nitrogen to which they are attached form piperazinyl, piperidinyl, morpholinyl, pyrrolidinyl, azepanyl, or diazepanyl, each optionally substituted with one or more $R^9$. In another embodiment, $R^4$ and $R^5$ together with nitrogen to which they are attached form piperidinyl optionally substituted with one or more $R^9$. In yet another embodiment, $R^4$ and $R^5$ together with nitrogen to which they are attached form unsubstituted piperidinyl. In some embodiments, $R^4$ and $R^5$ together with nitrogen to which they are attached form morpholinyl optionally substituted with one or more $R^9$. In some other embodiments, $R^4$ and $R^5$ together with nitrogen to which they are attached form unsubstituted morpholinyl.

In one embodiment, the disclosure provides compounds as described above with any reference to formula (I), wherein $R^6$ is hydrogen, optionally substituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl), or —N($R^{11}$)$_2$. In another embodiment, $R^6$ is hydrogen or optionally substituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In some embodiments, $R^6$ is hydrogen.

In some other embodiments, $R^6$ is $C_1$-$C_{20}$ alkyl (or $C_1$-$C_{10}$ alkyl, or $C_1$-$C_6$ alkyl, or $C_1$-Calkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl), wherein the alkyl is optionally substituted with —$OR^8$, $C_3$-$C_8$ cycloalkyl, $C_3$-$C_8$cycloalkenyl, or aryl, wherein each cycloalkyl, cycloalkenyl, and aryl are optionally substituted with $R^9$.

In some other embodiments, $R^6$ is $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl), wherein the alkyl is optionally substituted with $C_3$-$C_8$ cycloalkyl, $C_3$-$C_8$cycloalkenyl, or aryl, wherein each cycloalkyl, cycloalkenyl, and aryl are optionally substituted with $R^9$.

In one embodiment, the compounds of formula (I) are those wherein $R^6$ is —N($R^{11}$)$_2$. In one embodiment, each $R^{11}$ is independently hydrogen or $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In another embodiment, each $R^{11}$ is independently hydrogen or $C_1$-$C_6$ alkyl. In another embodiment, each $R^{11}$ is independently $C_1$-$C_6$ alkyl, or $C_1$-$C_4$ alkyl, or $C_1$-$C_3$ alkyl. In another embodiment, each $R^{11}$ is independently methyl or ethyl. In another embodiment, each $R^{11}$ is independently methyl.

In another embodiment, the compounds of formula (I) are those wherein $R^6$ is —$OR^{10}$, where $R^{10}$ is $C_1$-$C_6$ alkyl optionally substituted with $R^9$. In another embodiment, $R^6$ is —$OR^{10}$, where $R^{10}$ is aryl or aryl($C_1$-$C_6$ alkyl), where each aryl is optionally substituted with $R^9$.

Exemplary compounds of formula (I) include:

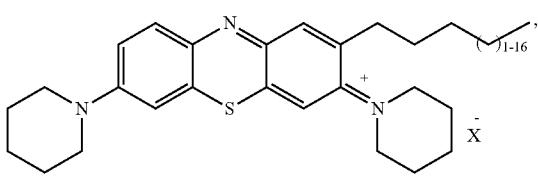

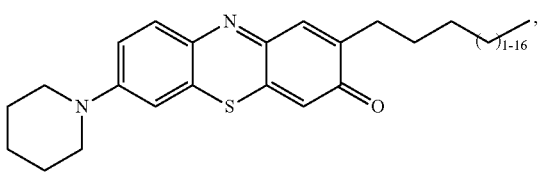

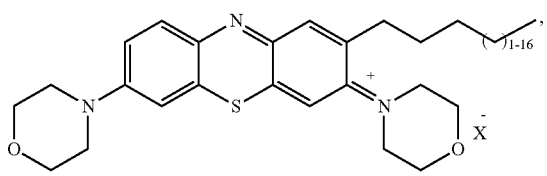

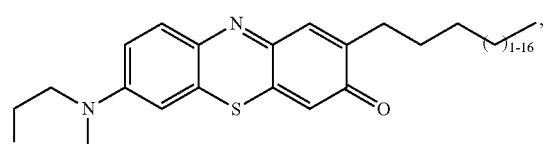

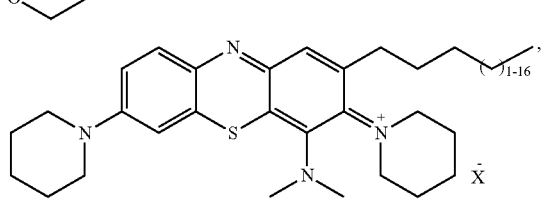

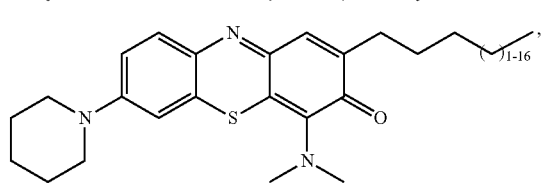

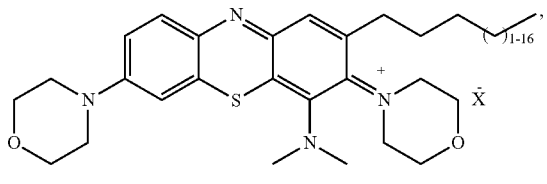

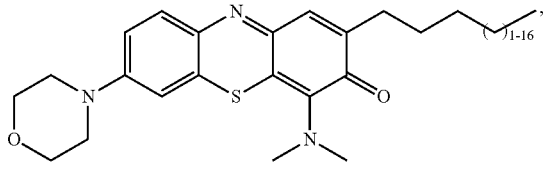

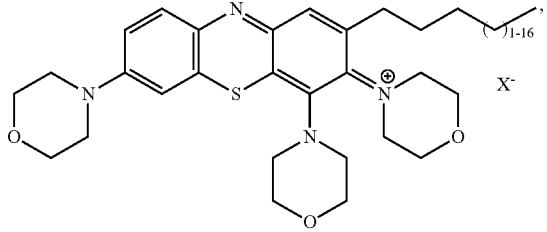

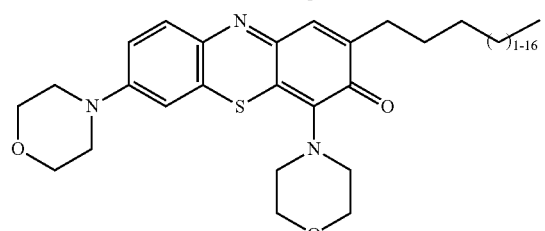

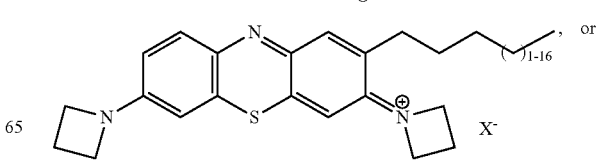

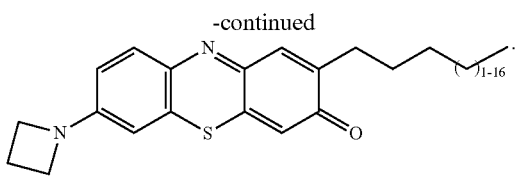

In one aspect, the disclosure provides a compound of formula (II):

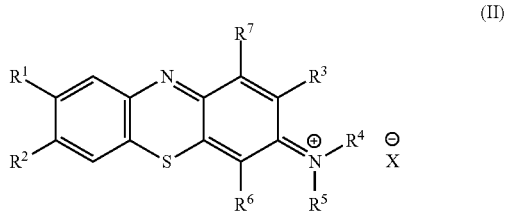

wherein
$X^-$ is a counterion;
$R^1$ is hydrogen, $C_1$-$C_{20}$ alkyl, $C_2$-$C_{20}$ alkenyl, $C_2$-$C_{20}$ alkynyl, —$OR^7$, —$SR^7$, —$NHR^7$, or —$N(R^7)_2$, each optionally substituted with one to four substituents selected from halogen, —CN, —$NO_2$, $C_1$-$C_6$ alkyl, halo($C_1$-$C_6$ alkyl), —$OR^8$, —$NR^8{}_2$, —$CO_2R^8$, —$CONR^8{}_2$, $C_3$-$C_8$ cycloalkyl, $C_3$-$C_8$cycloalkenyl, aryl, heteroaryl, and heterocycle, wherein each cycloalkyl, cycloalkenyl, aryl, heteroaryl, and heterocycle are optionally substituted with one or more $R^9$;
  where each $R^7$ independently is hydrogen, $C_1$-$C_6$ alkyl, or halo($C_1$-$C_6$ alkyl);
  where each $R^8$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with one or more $R^9$;
  where each $R^9$ independently is halogen, —CN, —$NO_2$, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;
$R^2$ and $R^6$ are independently —$N(R^{11})_2$;
  where each $R^{11}$ independently is hydrogen, $C_1$-$C_{20}$ alkyl, $C_2$-$C_{20}$ alkenyl, or $C_2$-$C_{20}$ alkynyl;
$R^3$ is hydrogen, $C_1$-$C_{20}$ alkyl, $C_2$-$C_{20}$ alkenyl, $C_2$-$C_{20}$ alkynyl, or —$OR^7$, each optionally substituted with one to four substituents selected from halogen, —CN, —$NO_2$, $C_1$-$C_6$ alkyl, halo($C_1$-$C_6$ alkyl), —$OR^8$, —$NR^8{}_2$, —$CO_2R^8$, —$CONR^8{}_2$, $C_3$-$C_8$ cycloalkyl, $C_3$-$C_8$cycloalkenyl, aryl, heteroaryl, and heterocycle, wherein each cycloalkyl, cycloalkenyl, aryl, heteroaryl, and heterocycle are optionally substituted with $R^9$;
$R^4$ and $R^5$ are independently $C_1$-$C_{20}$ alkyl, $C_2$-$C_{20}$ alkenyl, or $C_2$-$C_{20}$ alkynyl, each optionally substituted with one to four substituents selected from halogen, —CN, —$NO_2$, $C_1$-$C_6$ alkyl, halo($C_1$-$C_6$ alkyl), —$OR^8$, —$NR^8{}_2$, —$CO_2R^8$, —$CONR^8{}_2$, $C_3$-$C_8$ cycloalkyl, $C_3$-$C_8$cycloalkenyl, aryl, heteroaryl, and heterocycle, wherein each cycloalkyl, cycloalkenyl, aryl, heteroaryl, and heterocycle are optionally substituted with $R^9$;
  where $R^{10}$ is $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^9$; and
$R^7$ is hydrogen or —$N(R^{11})_2$.

In one embodiment, the disclosure provides compounds of formula (II), wherein $R^1$ is hydrogen, optionally substituted $C_1$-$C_{20}$ alkyl, optionally substituted $C_2$-$C_{20}$ alkenyl, optionally substituted $C_2$-$C_{20}$ alkynyl, or —$OR^7$. In some embodiments, $R^1$ is hydrogen. In some other embodiments, $R^1$ is optionally substituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In some embodiments, $R^1$ is $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl), wherein the alkyl is optionally substituted with —$OR^8$, $C_3$-$C_8$ cycloalkyl, $C_3$-$C_8$cycloalkenyl, or aryl, wherein each cycloalkyl, cycloalkenyl, and aryl are optionally substituted with $R^9$. In other embodiments, $R^1$ is $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl), wherein the alkyl is optionally substituted with $C_3$-$C_8$ cycloalkyl, $C_3$-$C_8$cycloalkenyl, or aryl, wherein each cycloalkyl, cycloalkenyl, and aryl are optionally substituted with $R^9$. In other embodiments, $R^1$ is —$OR^7$ and $R^7$ is $C_1$-$C_6$ alkyl.

In another embodiment, the disclosure provides compounds of formula (II), wherein $R^2$ is —$N(R^{11})_2$, where each $R^{11}$ independently is $C_1$-$C_{20}$ alkyl, $C_2$-$C_{20}$ alkenyl, or $C_2$-$C_{20}$ alkynyl. In one embodiment, $R^2$ is —$N(R^{11})_2$, where each $R^{11}$ independently is $C_1$-$C_6$ alkyl, $C_2$-$C_6$ alkenyl, or $C_2$-$C_6$ alkynyl.

In one embodiment, the disclosure provides compounds of formula (II), wherein $R^2$ is —$N(R^{11})_2$, where each $R^{11}$ independently is $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In some embodiments, each $R^{11}$ independently is $C_1$-$C_6$ alkyl. In another embodiment, each $R^{11}$ is independently $C_1$-$C_6$ alkyl, or $C_1$-$C_4$ alkyl, or $C_1$-$C_3$ alkyl. In another embodiment, each $R^{11}$ is independently methyl or ethyl. In another embodiment, each $R^{11}$ is independently methyl. For example, in some embodiments, $R^2$ is —$N(CH_3)_2$.

In one embodiment, the disclosure provides compounds as described above with any reference to formula (II), wherein $R^3$ is hydrogen, optionally substituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl), or —$OR^7$.

In another embodiment, the disclosure provides compounds as described above with any reference to formula (II), wherein $R^3$ is hydrogen. In yet another embodiment, the disclosure provides compounds as described above with any reference to formula (II), wherein $R^3$ is optionally substituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In one embodiment, the compounds of formula (II) are those wherein $R^3$ is $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl), wherein the alkyl is optionally substituted with —$OR^8$, $C_3$-$C_8$ cycloalkyl, $C_3$-$C_8$cycloalkenyl, or aryl, wherein each cycloalkyl, cycloalkenyl, and aryl are optionally substituted with $R^9$. In another embodiment, the compounds of formula (II) are those wherein $R^3$ is $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl), wherein the alkyl is optionally substituted with $C_3$-$C_8$ cycloalkyl, $C_3$-$C_8$ cycloalkenyl, or aryl, wherein each cycloalkyl, cycloalkenyl, and aryl are optionally substituted with $R^9$. In yet another embodiment, $R^3$ is unsubstituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl).

In some embodiments of formula (II), $R^3$ is $C_5$-$C_{20}$ alkyl optionally substituted with —$OR^8$, $C_3$-$C_8$ cycloalkyl, $C_3$-$C_8$ cycloalkenyl, or aryl, wherein each cycloalkyl, cycloalkenyl, and aryl are optionally substituted with $R^9$. In some other embodiments, $R^3$ is $C_5$-$C_{20}$ alkyl optionally substituted with $C_3$-$C_8$ cycloalkyl, $C_3$-$C_8$ cycloalkenyl, or aryl, wherein each cycloalkyl, cycloalkenyl, and aryl are optionally substituted with $R^9$. In some embodiments, $R^3$ is unsubstituted $C_5$-$C_{20}$ alkyl.

In some embodiments of formula (II), $R^3$ is $C_7$-$C_{20}$ alkyl optionally substituted with —$OR^8$, $C_3$-$C_8$ cycloalkyl, $C_3$-$C_8$ cycloalkenyl, or aryl, wherein each cycloalkyl, cycloalkenyl, and aryl are optionally substituted with $R^9$. In some other embodiments of formula (II), $R^3$ is $C_7$-$C_{20}$ alkyl optionally substituted with $C_3$-$C_8$ cycloalkyl, $C_3$-$C_8$ cycloalkenyl, or aryl, wherein each cycloalkyl, cycloalkenyl, and aryl are optionally substituted with $R^9$. In some embodiments, $R^3$ is unsubstituted $C_7$-$C_{20}$ alkyl.

In some embodiments of formula (II), $R^3$ is $C_{10}$-$C_{20}$ alkyl optionally substituted with —$OR^8$, $C_3$-$C_8$ cycloalkyl, $C_3$-$C_8$ cycloalkenyl, or aryl, wherein each cycloalkyl, cycloalkenyl, and aryl are optionally substituted with $R^9$. In some other embodiments of formula (II), $R^3$ is $C_{10}$-$C_{20}$ alkyl optionally substituted with $C_3$-$C_8$ cycloalkyl, $C_3$-$C_8$ cycloalkenyl, or aryl, wherein each cycloalkyl, cycloalkenyl, and aryl are optionally substituted with $R^9$. In some embodiments, $R^3$ is unsubstituted $C_{10}$-$C_{20}$ alkyl. For example, in some embodiments, $R^3$ is heptadecyl.

In one embodiment, the disclosure provides compounds as described above with any reference to formula (II), wherein $R^3$ is —$OR^7$ and $R^7$ is $C_1$-$C_6$ alkyl.

In one embodiment, the disclosure provides compounds as described above with any reference to formula (II), wherein $R^6$ is —$N(R^{11})_2$, and each $R^{11}$ is independently hydrogen or $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In one embodiment, each $R^{11}$ is independently $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In another embodiment, each $R^{11}$ is independently $C_1$-$C_6$ alkyl. In another embodiment, each $R^{11}$ is independently $C_1$-$C_6$ alkyl, or $C_1$-$C_4$ alkyl, or $C_1$-$C_3$ alkyl. In another embodiment, each $R^{11}$ is independently methyl or ethyl. In another embodiment, each $R^{11}$ is independently methyl. For example, in certain embodiments, $R^6$ is —$N(CH_3)_2$.

In one embodiment, the disclosure provides compounds as described above with any reference to formula (II), wherein $R^4$ is optionally substituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In one embodiment, $R^4$ is unsubstituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In certain embodiments, $R^4$ is optionally substituted $C_1$-$C_6$ alkyl. In some other embodiments, $R^4$ is unsubstituted $C_1$-$C_6$ alkyl, or $C_1$-$C_4$ alkyl, or $C_1$-$C_3$ alkyl. In other embodiments, $R^4$ is methyl.

In one embodiment, the disclosure provides compounds as described above with any reference to formula (II), wherein $R^5$ is optionally substituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In one embodiment, $R^5$ is unsubstituted $C_1$-$C_{20}$ alkyl (or $C_1$-$C_{10}$ alkyl, or $C_1$-$C_6$ alkyl, or $C_1$-$C_4$ alkyl, or $C_1$-$C_4$ alkyl, or $C_1$-$C_3$ alkyl, or $C_2$-$C_{20}$ alkyl, or $C_3$-$C_{20}$ alkyl, or $C_4$-$C_{20}$ alkyl, or $C_6$-$C_{20}$ alkyl, or $C_8$-$C_{20}$ alkyl). In certain embodiments, $R^5$ is optionally substituted $C_1$-$C_6$ alkyl. In some other embodiments, $R^5$ is unsubstituted $C_1$-$C_6$ alkyl, or $C_1$-$C_4$ alkyl, or $C_1$-$C_3$ alkyl. In other embodiments, $R^5$ is methyl.

In one embodiment, the compounds of formula (II) are wherein $X^-$ is a counterion. Counterions may include inorganic or organic counterions. Inorganic counterions include, by way of example and not limitation, halide (e.g., chloride, bromide, iodide, etc.), sulfate, nitrate, phosphate, hydroxide, oxide, and the like. Organic counterions include, by way of example and not limitation, acetate, monofluoroacetate, difluoroacetate, trifluoroacetate, propionate, hexanoate, cyclopentanepropionate, glycolate, oxalate, pyruvate, lactate, malonate, succinate, malate, maleate, fumarate, tartarate, citrate, palmitate, benzoate, 3-(4-hydroxybenzoyl)benzoate, cinnamate, mandelate, alkylsulfonates (e.g., methanesulfonate, ethanesulfonate, 1,2-ethane-disulfonate, 2-hydroxyethanesulfonate, etc.), arylsulfonates (e.g., benzenesulfonate, 4-chlorobenzenesulfonate, 2-naphthalenesulfonate, 4-toluenesulfonate, camphorsulfonate, etc.), 4-methylbicyclo[2.2.2]-oct-2-ene-1-carboxylate, glucoheptonate, 3-phenylpropionate, trimethylacetate, tertiary butylacetate, lauryl sulfurate, gluconate, glutamate, hydroxynaphthoate, salicylate, stearate, muconate, and the like.

In one embodiment, the compounds of formula (II) are wherein $X^-$ is halogen. In another embodiment, $X^-$ is $I^-$.

In one embodiment, the disclosure provides compounds as described above with any reference to formula (II), wherein $R^7$ is hydrogen.

In another embodiment, the disclosure provides compounds as described above with any reference to formula (II), wherein $R^7$ is —$N(CH_3)_2$.

Exemplary compounds of formula (II) include:

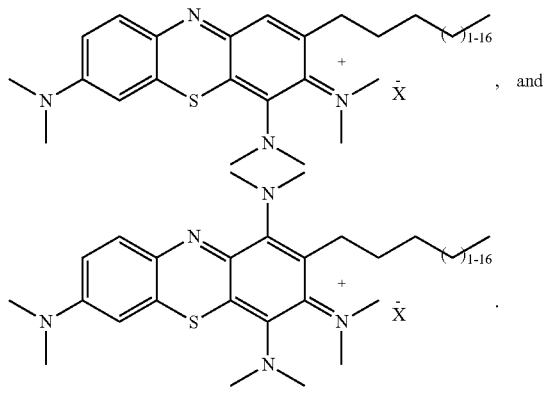

, and

Another aspect of the disclosure provides a compound that is:

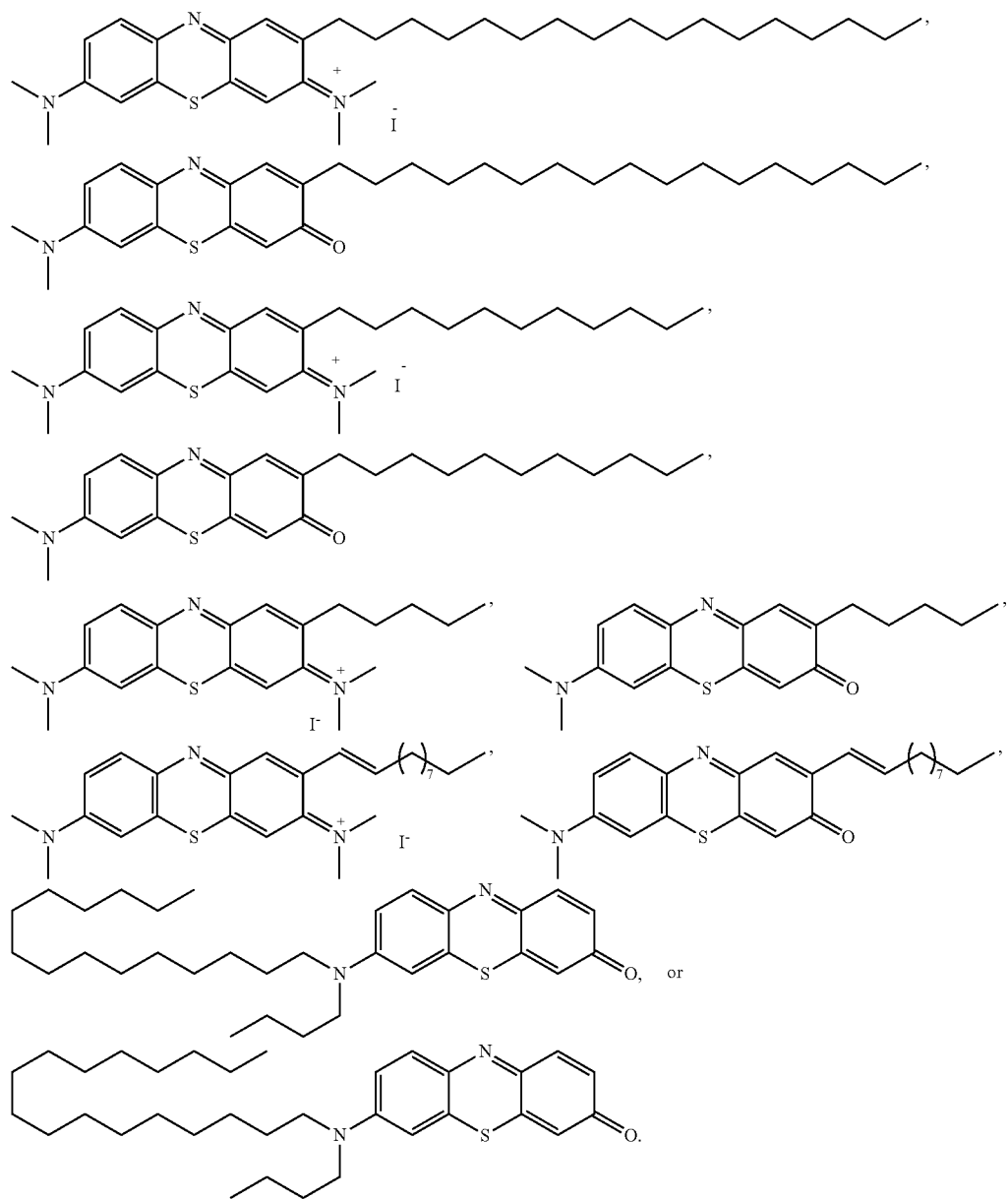

Leigh syndrome in a subject by administering an effective amount of a compound of the disclosure.

Therapeutic Applications

In one aspect, the disclosure provides a method for treating or protecting mitochondria with respiratory chain lesions, comprising administering to a subject in need of such treatment an effective amount of one or more compounds of the disclosure.

Compounds of the disclosure are useful, for example, for treating or suppressing diseases associated with decreased mitochondrial function resulting in diminished ATP production and/or oxidative stress and/or lipid peroxidation in a subject in need of treatment. The present disclosure provides methods of treating conditions including but not limited to Friedreich's ataxia, Leber's Hereditary Optic Neuropathy, Kearns-Sayre Syndrome, Mitochondrial Encephalomyopathy with Lactic Acidosis and Stroke-Like Episodes, and Leigh syndrome in a subject by administering an effective amount of a compound of the disclosure.

The disclosure also provides methods of treating conditions including but not limited to obesity, atherosclerosis, amyotrophic lateral sclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, and Leigh syndrome, in a subject by administering an effective amount of a compound of the disclosure.

In addition, the compounds of the disclosure can be used for prophylaxis of redox stress and enhancement of cellular function.

Friedreich's Ataxia

Friedreich's ataxia is a severe neurodegenerative and cardiodegenerative condition. It is characterized by progressive ataxia of the limbs, muscle weakness, dysarthria, skeletal deformities and cardiomyopathy. While the biochemical basis of the disease is still under investigation, it is strongly associated with insufficient frataxin (Wilson et al. (1997) *Nat. Genet.* 16, 352-357; Wilson et al. (2003) *J. Neurol. Sci.* 207, 103-105). In the majority of patients the insufficiency of frataxin is a consequence of an intronic GAA triplet repeat expansion in the gene for frataxin, which results in a significant decrease in its mRNA levels, and ultimately in protein levels as well (Campuzano et al. (1996) *Science* 271, 1423-1427; Campuzano et al. (1997) *Hum. Mol. Genet.* 6, 1771-1780). Frataxin acts as an iron chaperone during heme biosynthesis (Bencze et al. (2007) *J.C.S. Chem. Commun.* 1798-1800) and has been shown to be capable of stimulating the in vitro assembly of heme and Fe—S clusters (Park et al. (2003) *J. Biol. Chem.* 278, 31340-31351; Yoon et al. (2003) *J. Am Chem. Soc.* 125, 6078-6084; Yoon et al. (2004) *J. Biol. Chem.* 279, 25943-25946). Frataxin can interact physically with mitochondrial electron transport chain proteins, as well as with mitochondrial aconitase (which contains an Fe—S cluster) (Bulteau et al. (2004) *Science* 305, 242-245; Gonzalez-Cabo et al. (2005) *Hum. Mol. Genet.* 14, 2091-2098). Therefore, frataxin deficiency results in disruption of cellular iron homeostasis, with a progressive iron accumulation in the mitochondrion, and a deficiency in heme and Fe—S clusters.

It is believed that a deficiency in frataxin leads to compromised mitochondrial respiratory chain function through a failure to assemble one or more Fe-utilizing proteins; one or more Fe—S clusters in the mitochondrial respiratory complexes are likely to represent a critical locus. In fact, diminished function of these complexes has been noted in Friedreich's ataxia patients (Bradley et al. (2000) *Hum. Mol. Genet.* 9, 275-282). The loss of mitochondrial respiratory chain function can lead to diminished ATP production, while the accumulation of Fe in the mitochondria makes the organelle highly susceptible to oxidative damage by reactive oxygen species, whose concentration increases concomitant with the decrease in respiratory chain function. There is compelling evidence that while oxidative damage is not the primary lesion in Friedreich's ataxia, oxidative stress helps to drive disease progression. Therefore, strategies to overcome oxidative stress should blunt disease progression and provide effective therapy.

Other Exemplary Mitochondrial Diseases

Leber hereditary optic neuropathy is associated with degeneration of retinal ganglion cells and causes progressive loss of vision resulting in various degrees of blindness. Leber hereditary optic neuropathy primarily affects men over the age of 20 and is maternally transmitted due to mutations in the mitochondrial (not nuclear) genome.

Kearns-Sayre syndrome is a rare neuromuscular disorder typically with onset usually before the age of 20. It is characterized by progressive external ophthalmoplegia (paralysis of the eye muscles) and mild skeletal muscle weakness, hearing loss, loss of coordination, heart problems, and cognitive delays. There are many other names for the Kearns-Sayre syndrome including: Chronic progressive external ophthalmoplegia CPEO with myopathy; CPEO with ragged-red fibers; KSS; Mitochondrial cytopathy, Kearns-Sayre type; Oculocraniosomatic syndrome; Ophthalmoplegia-plus syndrome; Ophthalmoplegia with myopathy; and Ophthalmoplegia with ragged-red fibers.

Mitochondrial Encephalomyopathy with Lactic Acidosis and Stroke-Like Episodes is a progressive mitochondrial disease that involves multiple organ systems including the central nervous system, cardiac muscle, skeletal muscle, and gastrointestinal system. Symptoms include muscle weakness, stroke-like events, eye muscle paralysis, and cognitive impairment. Leigh syndrome is a degenerative brain disorder is usually diagnosed at a young age (e.g. before age two). Deterioration is often rapid with symptoms such as seizures, dementia, feeding and speech difficulties, respiratory dysfunction, heart problems, and muscle weakness. Prognosis is poor with death typically occurring within a few years of diagnosis.

Pharmaceutical Compositions

In another aspect, the present disclosure provides pharmaceutical compositions comprising one or more of compounds of the disclosure. The term "pharmaceutical composition" is used in its widest sense, encompassing all pharmaceutically applicable compositions containing at least one active substance, and optional carriers, excipient, diluent, adjuvants, constituents etc. The term "pharmaceutical composition" also encompasses a composition comprising the active substance in the form of derivative or pro-drug, such as pharmaceutically acceptable salts and esters. The manufacture of pharmaceutical compositions for different routes of administration falls within the capabilities of a person skilled in medicinal chemistry. The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound (s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinyl-pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known.

For buccal administration, the compositions may take the form of tablets or lozenges formulated in conventional manner.

For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoro-methane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective local dosages without undue experimentation.

Definitions

The following terms and expressions used herein have the indicated meanings.

As used in the specification and the appended claims, the singular forms "a," "an" and "the" include plural referents unless the context clearly dictates otherwise.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC$ ($CH_3$)—, —$CH_2CH(CH_2CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heterocyclyl" or "heterocycle" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

Some compounds of the disclosure may tautomerize. Thus, the disclosure also comprises all tautomeric forms of the compounds disclosed herein. Some compounds of the disclosure may have chiral centers and/or geometric isomeric centers (E- and Z-isomers), and it is to be understood that the disclosure encompasses all such optical, enantiomeric, diastereoisomeric and geometric isomers.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Treating" or "treatment" as used herein covers the treatment of a disease or disorder described herein, in a subject, preferably a human, and includes:
  i. inhibiting a disease or disorder, i.e., arresting its development;
  ii. relieving a disease or disorder, i.e., causing regression of the disorder;
  iii. slowing progression of the disorder; and/or
  iv. inhibiting, relieving, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

"Respiratory chain lesions" in mitochondria or "Mitochondria with respiratory chain lesions" refers to mitochondria in which the structures of the five complexes responsible for ATP production by oxidative phosphorylation are altered structurally, typically in a way that leads to diminished function.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

Methods of Synthesis

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Representative synthetic procedures for the preparation of compounds of the disclosure are outlined below.

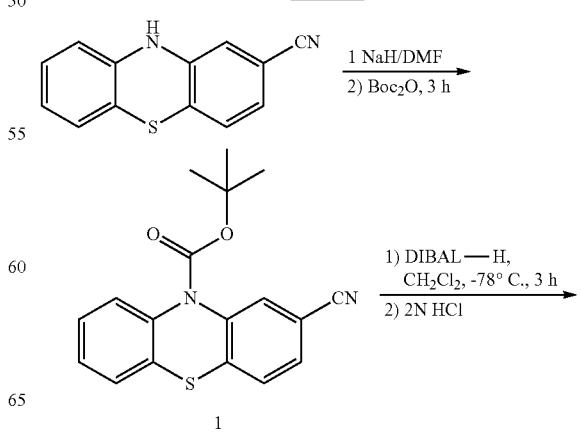

Scheme 1

-continued
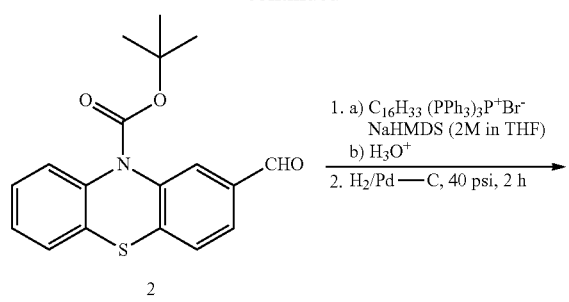
2
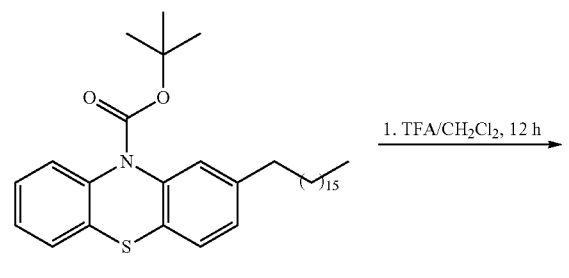
3
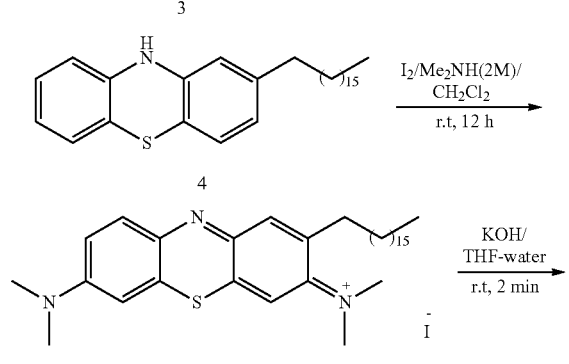
4
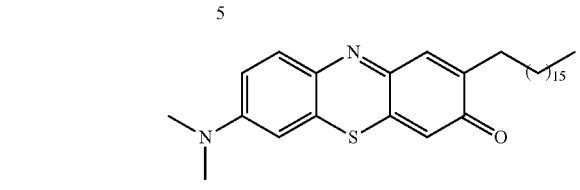
5
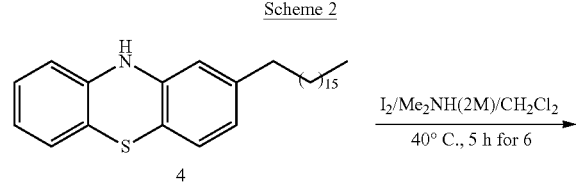
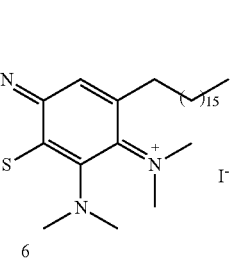
7
Scheme 2
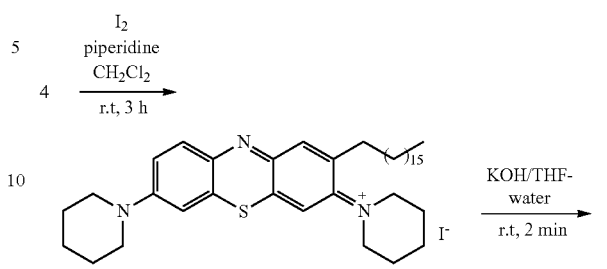
8
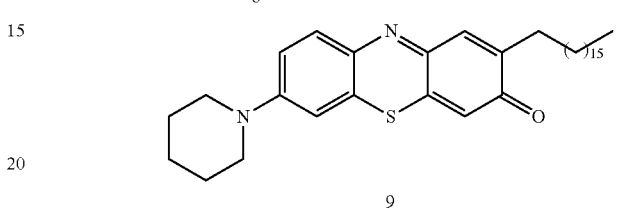
9
Scheme 3
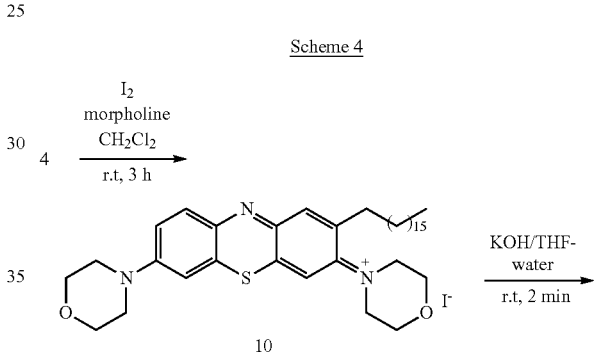
10
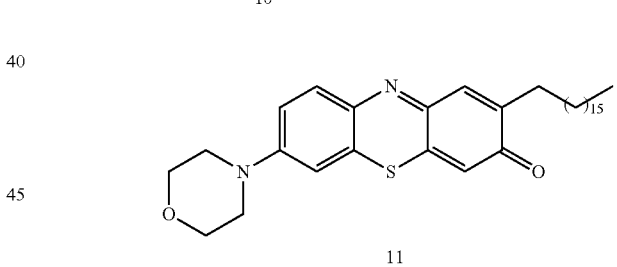
11
Scheme 4
Scheme 5
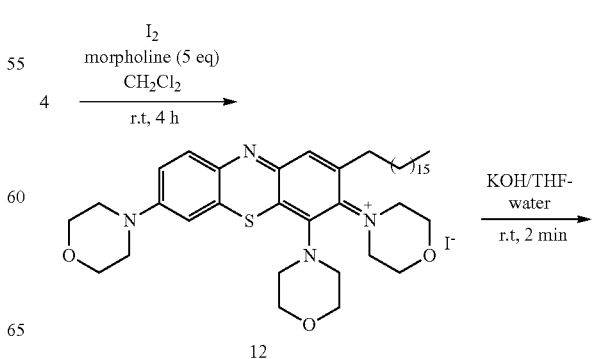
12

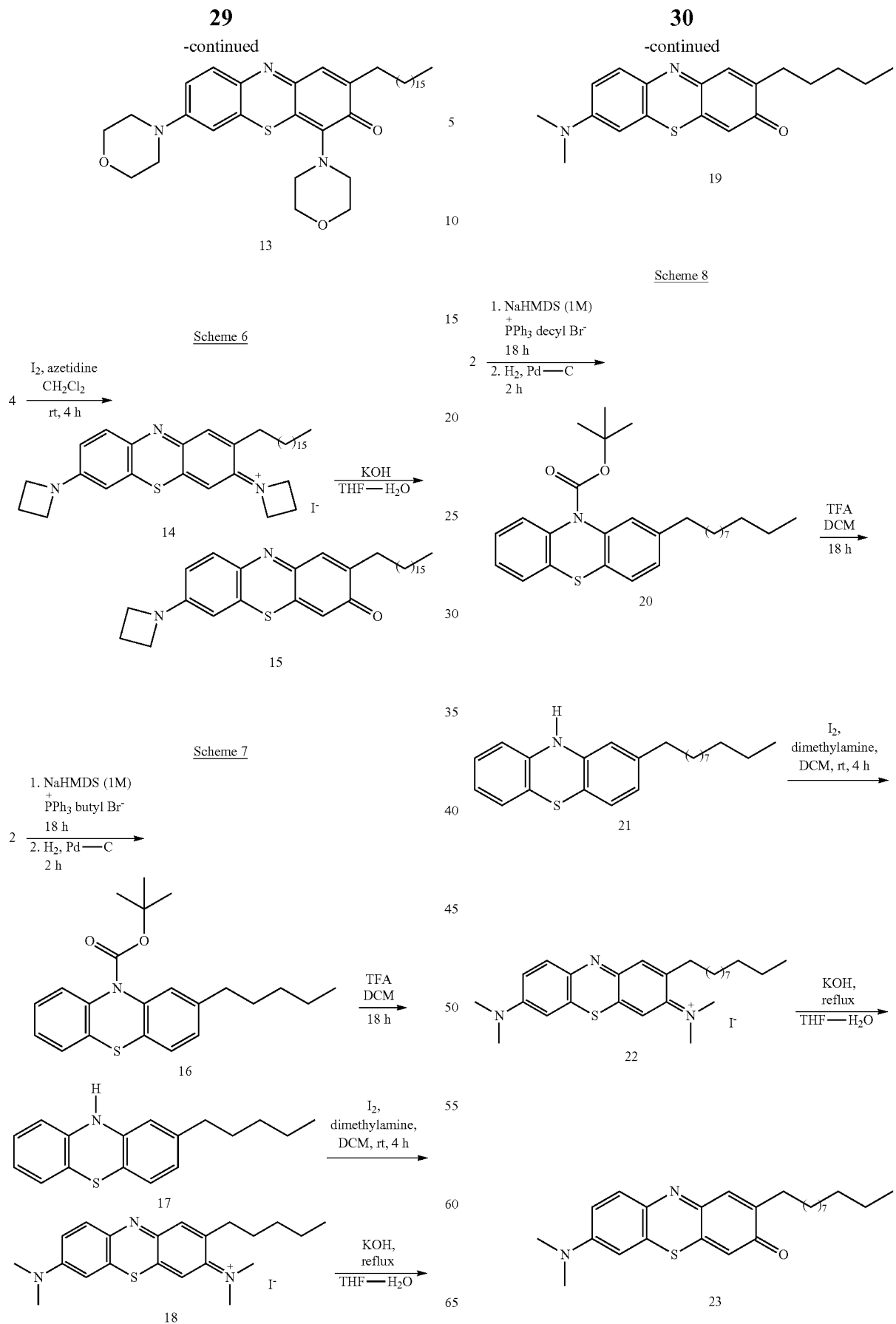

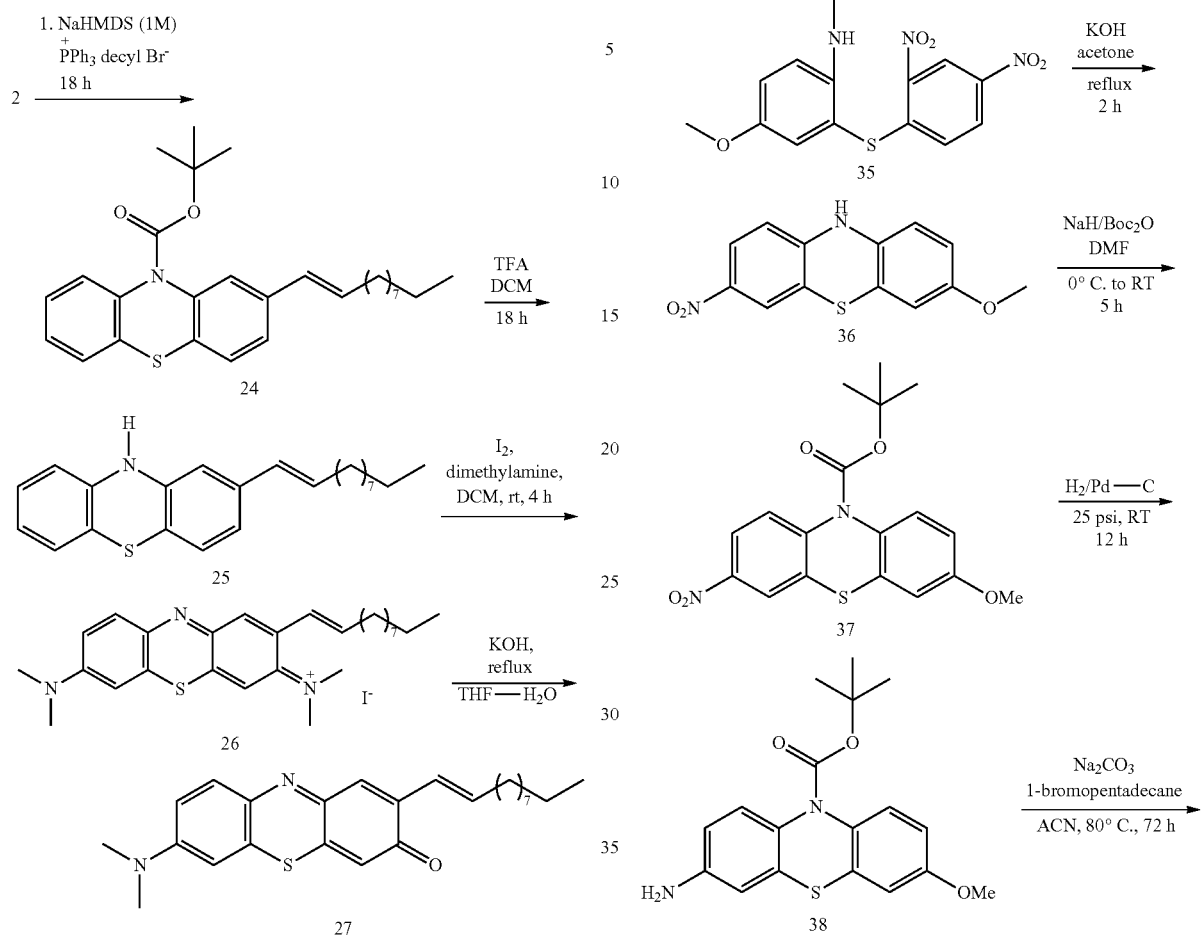
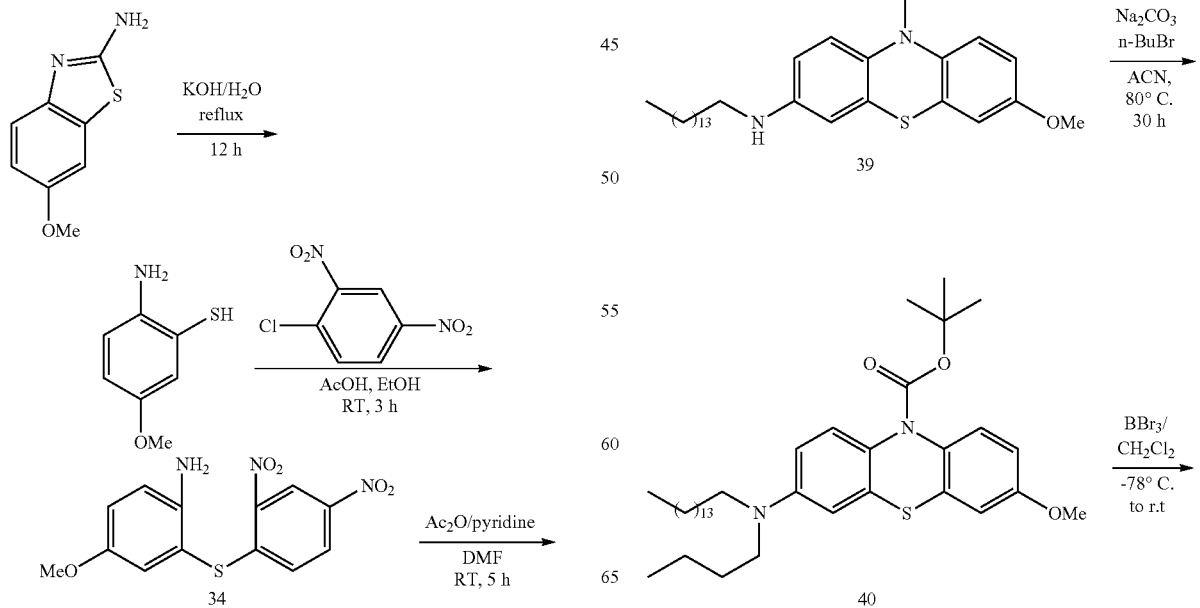

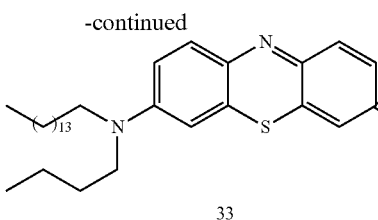

33

EXAMPLES

The compounds and methods of the disclosure are illustrated further by the following examples, which are provided for illustrative purposes and are not intended to be construed as limiting the disclosure in scope or spirit to the specific compounds and methods described in them.

Example 1

2-cyanophenothiazine (0.74 g, 3.30 mmol) was dissolved in 10 mL of anhydrous DMF. The mixture was cooled to 0° C. and 60% NaH (0.40 g, 9.90 mmol) was added. The dark mixture was stirred at 0° C. for an additional 15 min and Di-tent-butyl dicarbonate (0.90 g, 3.96 mmol) was added. The mixture was stirred at room temperature for 3 h and was diluted with 50 mL of brine. The aqueous layer was extracted with three 25 mL portions of ethyl acetate. The combined organic extract was dried over anhydrous $MgSO_4$ and concentrated under diminished pressure. The crude was purified on a silica gel column (10 cm×2 cm). Elution with ethyl acetate-hexane (1:9) gave 1 as a pale yellow solid: yield 1.07 g (100%); silica gel TLC $R_f$ 0.26 (ethyl acetate-hexane 1:9); $^1$H NMR ($CDCl_3$) δ 1.49 (s, 9H), 7.16-7.20 (m, 1H), 7.28-7.33 (m, 2H), 7.40 (s, 2H), 7.49 (d, 1H, J=8.4 Hz) and 7.80 (s, 1H); $^{13}$C NMR δ 28.1, 83.1, 110.2, 118.2, 126.6, 127.2, 127.3, 127.5, 128.1, 129.1, 130.3, 130.6, 137.7, 139.0, 139.1 and 151.8; mass spectrum (APCI), m/z 325.1017 $(M+H)^+$ ($C_{18}H_{17}N_2O_2S$ requires m/z 325.1011).

Example 2

To a solution of the crude product in 10 mL of anhydrous $CH_2Cl_2$ was added 4.0 mL (4.0 mmol) of 1M DIBAL-H in toluene dropwise at −78° C. The mixture was stirred at −78° C. for 3 h and was diluted with 2N HCl. The aqueous layer was extracted with three 30 mL portions of $CH_2Cl_2$. The combined organic extract was dried over anhydrous $MgSO_4$ and was concentrated under diminished pressure. The residue was purified on a silica gel column (7 cm×4 cm). Elution with 1:9 ethyl acetate-hexanes afforded 2 as a yellow solid: yield 0.63 g (58%); silica gel TLC $R_f$ 0.17 (ethyl acetate-hexane 1:9); $^1$H NMR ($CDCl_3$) δ 1.48 (s, 9H), 7.14-7.18 (m, 1H), 7.26-7.32 (m, 2H), 7.44 (d, 1H, J=8.0 Hz), 7.52 (d, 1H, J=7.4 Hz), 7.64 (d, 1H, J=8.0 Hz), 7.99 (s, 1H) and 9.96 (s, 1H); $^{13}$C NMR δ 28.1, 82.8, 126.5, 126.6, 127.1, 127.3, 127.4, 127.8, 128.3, 130.5, 135.1, 137.9, 139.1, 140.2 and 152.1; mass spectrum (ESI), m/z 328.0823 $(M+Na)^+$ ($C_{18}H_{17}NO_3SNa$ requires m/z 328.0827).

Example 3:

To a solution of hexadecyltriphenylphosphonium bromide (0.64 g, 1.13 mmol) in 5 mL of anhydrous THF at −78° C. was added 1.20 mL (1.20 mmol) of 1M sodium bis-(trimethylsilyl)amide in THF dropwise. The yellow mixture was stirred at 0° C. for 3 h and was cooled to −78° C. To this bright orange suspension was added 2 (0.37 g, 1.13 mmol) dissolved in 5 mL of anhydrous THF dropwise. The light yellow mixture was stirred at 0° C. under argon atmosphere overnight and was diluted with 50 mL of brine. The aqueous layer was extracted with three 25 mL portions of ethyl acetate. The combined organic extract was dried over anhydrous $MgSO_4$ and was concentrated under diminished pressure. The residue was purified on a silica gel column. Elution with 1:9 $CH_2Cl_2$-hexanes yielded a cis-trans mixture as a white solid.

To a solution of the cis-trans mixture (0.41 g, 0.77 mmol) in 3:7 $CH_2Cl_2$-ethanol was added palladium on carbon (26 mg, 0.16 mmol). The suspension was stirred at room temperature under $H_2$ atmosphere (40 psi) for 2 h. The mixture was filtered through celite pad. The filtrate was concentrated under diminished pressure to afford 3 as a white solid: yield 0.41 g (74% over two steps); silica gel TLC $R_f$ 0.1 ($CH_2Cl_2$-hexane 1:9); $^1$H NMR ($CDCl_3$) δ 0.88 (t, 3H, J=7.0 Hz), 1.26-1.30 (m, 28H), 1.49 (s, 9H), 1.60 (t, 2H, J=7.2 Hz), 2.59 (t, 2H, J=7.6 Hz), 6.96 (d, 1H, J=7.6 Hz), 7.12 (t, 1H, J=7.6 Hz), 7.21-7.26 (m, 2H), 7.32-7.35 (m, 2H) and 7.52 (d, 1H, J=7.6 Hz); $^{13}$C NMR ($CDCl_3$) δ 14.3, 22.9, 28.4, 29.5, 29.53, 29.70, 29.74, 29.84, 29.87, 31.7, 32.1, 35.8, 82.0, 126.1, 126.5, 126.6, 127.2, 127.33, 127.37, 127.6, 128.9, 132.7, 138.8, 139.0, 142.0 and 152.7; mass spectrum (MALDI-TOF), m/z 537.3575 $(M+H)^+$ ($C_{34}H_{51}NO_2S$ requires m/z 537.3641).

Example 4:

To a solution of 3 (0.23 g, 0.43 mmol) in 8 mL of anhydrous $CH_2Cl_2$ was added 0.26 mL (3.44 mmol) of trifluoroacetic acid dropwise. The mixture was stirred at room temperature for 12 h under argon atmosphere and was neutralized with 50 mL of saturated $NaHCO_3$ solution. The aqueous layer was extracted with three 30 mL portions of $CH_2Cl_2$. The combined organic layer was dried over anhydrous $MgSO_4$ and was concentrated under diminished pressure. The crude (4) was utilized in the next step without further purification.

Example 5

(5)

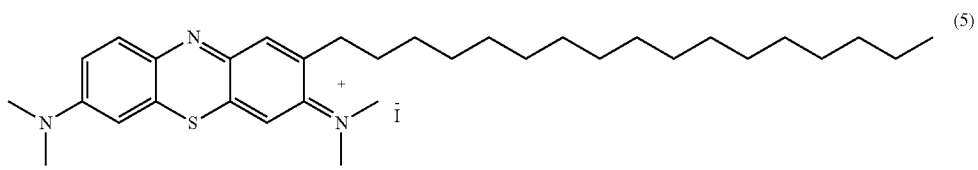

N-(7-(dimethylamino)-2-heptadecyl-3H-phenothiazin-3-ylidene)-N-methylmethanaminium iodide To a solution 45 mg of the crude 4 in 5 mL of CH$_2$Cl$_2$ was added 81 mg (0.32 mmol) of iodine followed by 0.25 mL (0.5 mmol) of 2M Dimethylamine in THF. The mixture was stirred at room temperature under argon atmosphere for 12 h. The greenish blue mixture was purified on a silica gel column (10 cm×2 cm). Elution with ethyl acetate afforded 5 as a green solid: yield 18 mg (28%); silica gel TLC R$_f$ 0.4 (ethyl acetate); $^1$H NMR (CDCl$_3$) δ 0.86 (t, 3H, J=6.6 Hz), 1.15-1.37 (m, 28H), 1.69-1.72 (m, 2H), 2.81-2.85 (m, 2H), 3.33 (s, 6H), 3.46 (s, 6H), 7.36-7.38 (m, 1H), 7.41 (s, 1H), 7.76 (m, 1H), 7.89 (s, 1H), 7.99 (d, 1H, J=7.6 Hz); mass spectrum (MALDI-TOF), m/z 522.3978 (M)$^+$ (C$_{33}$H$_{52}$N$_3$S requires m/z 522.3876).

Example 6

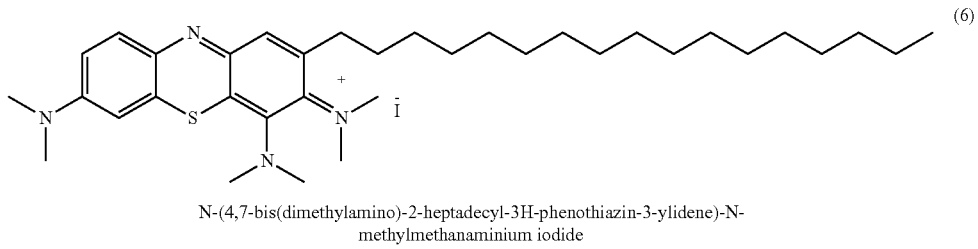

N-(4,7-bis(dimethylamino)-2-heptadecyl-3H-phenothiazin-3-ylidene)-N-methylmethanaminium iodide To a solution 0.10 g of the crude (4) in 5 mL of anhydrous CH$_2$Cl$_2$ was added 0.19 g (0.74 mmol) of iodine followed by 1.15 mL (2.3 mmol) of 2M Dimethylamine in THF. The mixture was heated at 45° C. under argon atmosphere for 7 h. The blue mixture was purified on a silica gel column (10 cm×2 cm). Elution with 20% methanol in ethyl acetate afforded 6 as a blue solid: yield 40 mg (31%); silica gel TLC R$_f$ 0.35 (ethyl acetate-methanol 4:1); $^1$H NMR (CDCl$_3$) δ 0.86 (t, 3H, J=6.8 Hz), 1.24-1.44 (m, 28H), 1.61-1.63 (m, 2H), 2.71 (m, 2H), 3.28 (s, 6H), 3.30 (s, 6H), 3.49 (s, 6H), 6.17 (s, 1H), 6.89 (d, 1H, J=2.8 Hz), 7.05 (dd, J=9.2 Hz, J=2.4 Hz), 7.78 (d, 1H, J=9.6 Hz); $^{13}$C NMR δ 14.3, 22.8, 26.4, 29.5, 29.8, 29.82, 29.85, 30.1, 30.7, 32.1, 41.4, 44.7, 45.9, 51.0, 101.3, 105.6, 115.8, 121.5, 130.6, 131.1, 132.2, 133.8, 137.0, 153.5 and 161.1; mass spectrum (MALDI-TOF), m/z 565.4135 (M)$^+$ (C$_{35}$H$_{57}$N$_4$S requires m/z 565.4298).

Example 7

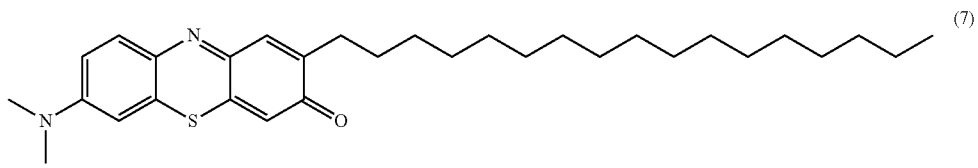

7-(dimethylamino)-2-heptadecyl-3H-phenothiazin-3-one

To a dark green solution of 5 (70 mg, 0.09 mmol) in 3.5 mL THF-H$_2$O (6:1) was added KOH (30 mg, 0.53 mmol). The mixture was stirred for 2 minute at room temperature until it changes from green to red. The aqueous layer was extracted with EtOAc. The organic layer was dried over anhydrous MgSO$_4$ and was concentrated under diminished pressure. The crude was purified on a silica gel column (7 cm×2 cm). Elution with 2:3 EtOAc-hexane yielded 7 as a violet solid: yield-11 mg (24%); silica gel TLC R$_f$ 0.59 (ethyl acetate-hexane 2:3); $^1$H NMR (CDCl$_3$) δ 0.86-0.89 (m, 3H), 1.27-1.41 (m, 28H), 1.72 (t, 2H, J=6.0 Hz), 2.72 (t, 2H, J=6.4 Hz), 2.89 (s, 6H), 6.73 (d, 1H, J=1.6 Hz), 6.89 (dd, 1H, J=7.6 Hz, J=2.0 Hz), 6.93 (s, 1H), 7.60 (d, 1H, J=8.0 Hz) and 7.71 (s, 1H); $^{13}$C NMR (CDCl$_3$) δ 14.3, 22.8, 29.5, 29.6, 29.7, 29.81, 29.85, 30.1, 31.6, 32.1, 44.0, 112.8, 119.3, 123.3, 134.0, 134.6, 135.5, 136.4, 139.7, 143.3, 155.8 and 182.5; mass spectrum (ESI), m/z 495.3414 (M+H)$^+$ (C$_{31}$H$_{47}$N$_2$OS requires m/z 495.3409).

Example 8

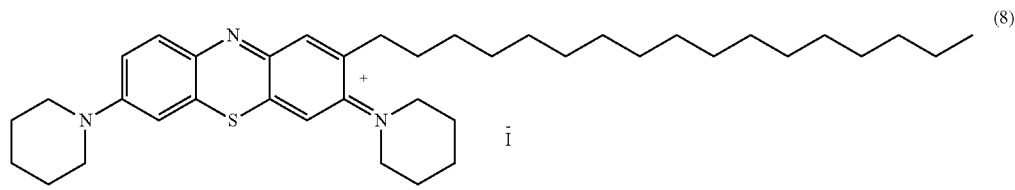

1-(2-heptadecyl-7-(piperidin-1-yl)-3H-phenothiazin-3-ylidene)piperidin-1-ium iodide Crude 4 (30 mg, 0.07 mmol) was dissolved in 5 mL CH$_2$Cl$_2$ and I$_2$ (56 mg, 0.22 mmol) was added followed by piperidine (34 μL, 0.35 mmol). The mixture was stirred at room temperature for 3 h under argon atmosphere and was purified on a silica gel column (8 cm×2 cm). Elution with ethyl acetate gave 8 as a green solid: yield-5 mg (10%); silica gel TLC R$_f$ 0.43 (ethyl acetate); $^1$H NMR (CDCl$_3$) δ 0.86-0.89 (m, 3H), 1.24-1.40 (m, 28H), 1.76-1.80 (m, 2H), 2.76 (t, 2H, J=7.8 Hz), 3.43-3.45 (m, 3H), 3.92-3.98 (m, 1H), 7.56 (s, 1H), 7.61-7.64 (m, 1H), 7.69 (d, 1H, J=2.0 Hz), 8.06 (s, 1H) and 8.13 (d, 1H, J=9.6 Hz); mass spectrum (MALDI-TOF), m/z 602.4560 (M)$^+$ (C$_{39}$H$_{60}$N$_3$S requires m/z 602.4502).

Example 9

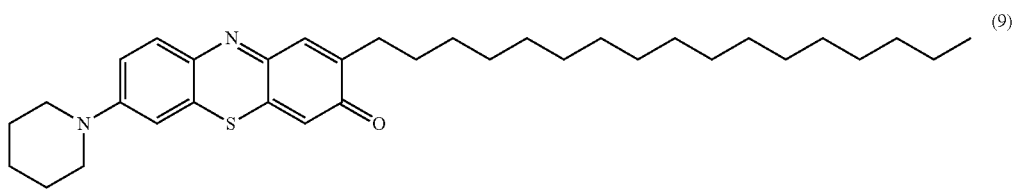

2-heptadecyl-7-(piperidine-1-yl)-3H-phenothiazin-3-one

To a dark green solution of 8 (60 mg, 0.1 mmol) in 3.5 mL THF-H$_2$O (6:1) was added KOH (16 mg, 0.3 mmol). The mixture was stirred for 2 minute at room temperature until it changes from green to red. The aqueous layer was extracted with EtOAc. The organic layer was dried over anhydrous MgSO$_4$ and was concentrated under diminished pressure. The crude was purified on a silica gel column (7 cm×2 cm). Elution with 1:4 ethyl acetate-hexane yielded 9 as a brownish solid: yield-12.3 mg (22%); silica gel TLC R$_f$ 0.75 (ethyl acetate-hexane 3:2); $^1$H NMR (CDCl$_3$) δ 0.86-0.88 (m, 3H), 1.22-1.38 (m, 28H), 1.62-1.67 (m, 8H), 2.64 (t, 2H, J=8.0 Hz), 2.96 (t, 2H, J=4.8 Hz), 6.71 (d, 1H, J=2.0 Hz), 6.87 (dd, 1H, J=12 Hz, J=2.0 Hz), 6.94 (s, 1H), 7.57 (d,1H, J=10 Hz) and 7.70 (s, 1H); $^{13}$C NMR (CDCl$_3$) δ 14.1, 22.6, 22.7, 24.1, 26.1, 29.3, 29.4, 29.5, 29.54, 29.6, 29.63, 29.67, 30.2, 30.5, 31.6, 31.9, 53.5, 114.1 119.1, 122.9, 134.0, 134.9, 135.0, 137.0, 139.6, 143.6, 156.1 and 182.3; mass spectrum (ESI), m/z 535.3731 (M+H)$^+$ (C$_{34}$H$_{51}$N$_2$OS requires m/z 535.3722).

Example 10

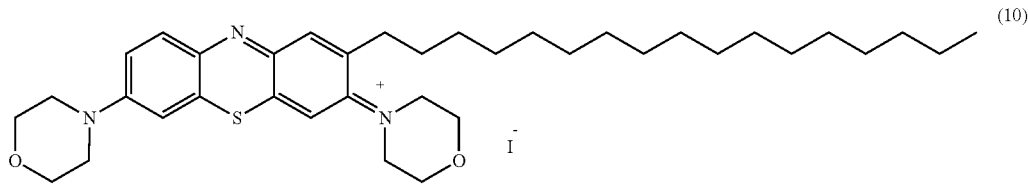

4-(2-heptadecyl-7-morpholino-3H-phenothiazin-3-ylidene)morpholin-4-ium iodide

Crude 4 (44 mg, 0.10 mmol) was dissolved in 5 mL CH$_2$Cl$_2$ and I$_2$ (81 mg, 0.32 mmol) was added followed by morpholine (47 μL, 0.50 mmol). The mixture was stirred at room temperature for 3 h under argon atmosphere and was purified on a silica gel column. Elution with ethyl acetate gave 10 as a green solid: yield-5 mg (7%); silica gel TLC R$_f$ 0.43 (ethyl acetate); $^1$H NMR (CDCl$_3$) δ 0.86 (m, 3H), 1.24-1.40 (m, 28H), 1.76-1.80 (m, 2H), 2.76 (t, 2H, J=7.8 Hz), 3.43-3.45 (m, 3H), 3.92-3.98 (m, 1H), 7.56 (s, 1H), 7.61-7.64 (m, 1H), 7.69 (d, 1H, J=2.0 Hz), 8.06 (s, 1H) and 8.13 (d, 1H, J=9.6 Hz); $^{13}$C NMR (CDCl$_3$) δ 14.1, 22.7, 29.3, 29.4, 29.5, 29.6, 29.7, 30.1, 30.9, 31.9, 32.1, 48.9, 52.3, 66.6, 107.7, 113.7, 121.2, 130.9, 137.6, 137.9, 139.7, 139.8, 140.1, 153.9 and 157.9; mass spectrum (ESI), m/z 606.4113 (M)$^+$ (C$_{37}$H$_{56}$N$_3$O$_2$S requires m/z 606.4093).

Example 11

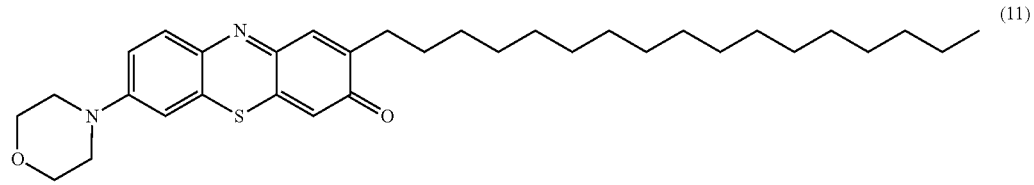

2-heptadecyl-7-(morpholine-1-yl)-3H-phenothiazin-3-one

To a dark green solution of 10 (58 mg, 0.1 mmol) in 3.5 mL THF-H$_2$O (6:1) was added KOH (11 mg, 0.19 mmol). The mixture was stirred for 2 minute at room temperature until it changes from green to red. The aqueous layer was extracted with EtOAc. The organic layer was dried over anhydrous MgSO$_4$ and was concentrated under diminished pressure. The crude was purified on a silica gel column. Elution with 1:4 ethyl acetate-hexane yielded 11 as a brownish solid: yield-7 mg (14%); silica gel TLC R$_f$ 0.75 (ethyl acetate-hexane 3:2); $^1$H NMR (CDCl$_3$) δ 0.86 (m, 3H), 1.21-1.38 (m, 28H), 1.69-1.70 (m, 2H), 2.67 (t, 2H, J=8.0 Hz), 2.99-3.02 (m, 4H), 3.86-3.88 (m, 4H), 6.72 (d, 1H, J=2.0 Hz), 6.89 (dd, 1H, J=10.2 Hz, J=2.2 Hz), 6.97 (s, 1H), 7.58 (d,1H, J=10 Hz) and 7.74 (s, 1H); mass spectrum (ESI), m/z 537.3518 (M+H)$^+$ (C$_{33}$H$_{49}$N$_2$O$_2$S requires m/z 537.3515).

Example 12

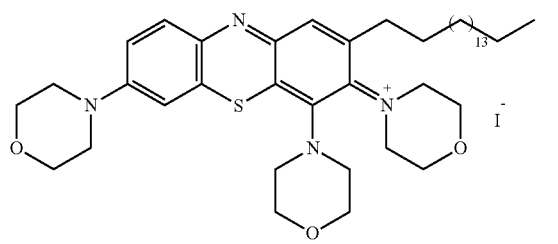

N-(4,7-bis(morpholino)-2-heptadecyl-3H-phenothiazin-3-ylidene)-N-morpholinium iodide 4 (0.20 g, 0.45 mmol) was dissolved in dichloromethane. Iodine (0.37 g, 1.46 mmol) was added and the reaction was run in the dark for 15 minutes. Thereafter, morpholine (0.20 ml (0.20 g), 2.28 mmol) was added dropwise and the reaction was allowed to run for 4 h. The product was dissolved in dichloromethane and the solution was concentrated under diminished pressure. The residue was purified by chromatography on a silica gel column (20×3 cm). Elution with at 1:1 ethylacetate/methanol afforded N-(4,7-bis(morpholino)-2-heptadecyl-3H-phenothiazin-3-ylidene)-N-morpholinium iodide (12) as a blue violet solid: yield 0.10 g (27%); silica gel TLC R$_f$ 0.48 (1:1 ethylacetate/methanol); $^1$H NMR (CDCl$_3$) (500 MHz) δ 0.85 (t, 3H, J=6.7 Hz), 1.23 (s, 30H), 1.70 (m, 2H), 2.68 (t, 2H, J=8 Hz), 3.18 (t, 3H, J=4.5 Hz), 3.27 (t, 2H, J=5 Hz), 3.78 (t, 3H, J=4.5 Hz), 3.88 (t, 3H, J=4.5 Hz), 3.93 (t, 3H, J=4.7 Hz), 3.98 (t, 3H, J=4.5 Hz), 4.04 (s, 3H), 4.12 (t, 2H, J=5 Hz), 6.51 (d, 1H, J=2.5 Hz), 7.29 (s, 1H) and 7.69 (s, 2H); $^{13}$C NMR (CDCl$_3$) (125 MHz) δ 14.24, 22.80, 29.46, 29.56, 29.81, 30.44, 31.38, 32.03, 42.98, 49.57, 52.39, 52.81, 62.98, 66.82, 66.92, 101.97, 107.21, 114.29, 127.58, 134.53, 136.29, 136.69, 137.32, 138.84, 155.56, 156.95 and 157.04; mass spectrum (APCI), m/z (M+2H)$^+$ 693.4799 (C$_{41}$H$_{65}$N$_4$O$_3$S requires 693.4777); ultraviolet/visible spectrum λ$_{max}$ 589.9 nm (in dichloromethane), λ$_{max}$ 575.0 nm (in methanol).

Example 13

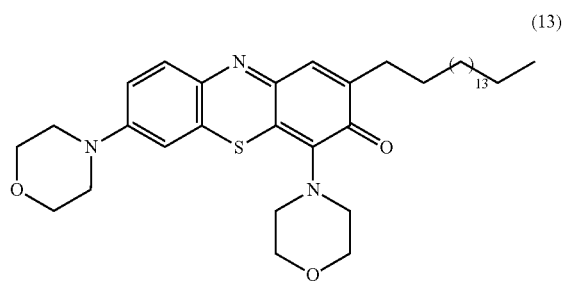

4,7-bis(morpholino)-2-heptadecyl-3H-phenothiazin-3-one 12 (0.10 g, 0.14 mmol) was dissolved in a mixture of tetrahydrofuran/water (6:1). Solid KOH (0.008 g, 0.14 mmol) was added and the reaction mixture was stirred for 10 minutes. As soon as the reaction mixture changed colour from blue-violet to chocolate brown, the reaction was quenched with water. The product was extracted in ethyl acetate, washed with brine, dried (Na$_2$SO$_4$) and was concentrated under diminished pressure. The residue was purified by chromatography on a silica gel column (20×1 cm). Elution with at 4:1 hexane/ethylacetate afforded 4,7-bis (morpholino)-2-heptadecyl-3H-phenothiazin-3-one (13) as a chocolate brown solid: yield 0.01 g (20%); silica gel TLC R$_f$ 0.37 (ethylacetate); $^1$H NMR (CDCl$_3$) (500 MHz) δ 0.87

(t, 3H, J=6.7 Hz), 1.25 (s, 30H), 1.68 (m, 2H), 2.66 (t, 2H, J=8 Hz), 2.99 (t, 2H, J=4.5 Hz), 3.37 (t, 3H, J=4 Hz), 3.87 (t, 3H, J=4 Hz), 3.95 (t, 3H, J=4.25 Hz), 6.11 (s, 1H), 6.53 (s, 1H), 6.93 (s, 1H) and 7.57 (s, 1H); $^{13}$C NMR (CDCl$_3$) (125 MHz) δ 14.27, 22.84, 29.51, 29.62, 29.85, 30.59, 32.07, 51.83, 52.72, 66.78, 67.14, 114.65, 115.43, 119.83, 122.98, 133.93, 134.19, 135.11, 137.55, 141.10, 154.37, 156.01 and 182.38; mass spectrum (APCI), m/z (M+H)$^+$ 622.4033 (C$_{37}$H$_{56}$N$_3$O$_3$S requires 622.4042); ultraviolet/visible spectrum $\lambda_{max}$ 474.9 nm (in dichloromethane), $\lambda_{max}$ 475.0 nm (in methanol).

Example 14

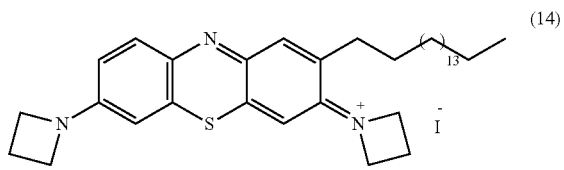

N-(7-(azetidino)-2-heptadecyl-3H-phenothiazin-3-ylidene)-N-azetidinium iodide

The azetidine hydrochloride (0.21g, 2.33 mmol) was dissolved in methanol. Sodium carbonate was added to it until the solution was basic (tested by pH paper). The residual excess sodium carbonate was separated from the azetidine solution by decantation. This azetidine in methanol solution was directly used for the reaction. 4 (0.20g, 0.46 mmol) was dissolved in dichloromethane. Iodine (0.37g, 1.49 mmol) was added and the reaction was run in the dark for 15 minutes. Thereafter, azetidine (dissolved in methanol) was added dropwise and the reaction was allowed to run for 4 h. The product was dissolved in dichloromethane and the solution was concentrated under diminished pressure. The crude product N-(7-(azetidino)-2-heptadecyl-3H-phenothiazin-3-ylidene)-N-azetidinium iodide (14) was obtained as a dirty green solid. Mass spectrum (MALDI-TOF), m/z (M$^+$) 546.957 (C$_{35}$H$_{52}$N$_3$S requires 546.3876).

Example 15

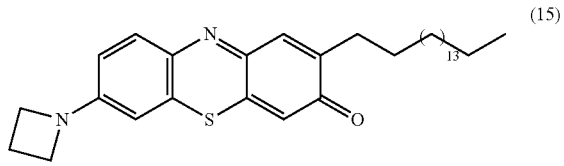

7-(azetidino)-2-heptadecyl-3H-phenothiazin-3-one 14 (0.06 g, 0.10 mmol) was dissolved in a mixture of tetrahydrofuran/water (6:1). Solid KOH (0.006 g, 0.10 mmol) was added and the reaction mixture was stirred for 10 minutes. As soon as the reaction mixture changed colour from green to red, the reaction was quenched with water. The product was extracted in ethyl acetate, washed with brine, dried (Na$_2$SO$_4$) and was concentrated under diminished pressure. The crude product 7-(azetidino)-2-heptadecyl-3H-phenothiazin-3-one (15) was obtained as a light red solid. Mass spectrum (MALDI-TOF), m/z (M+H)$^+$ 507.952 (C$_{32}$H$_{47}$N$_2$OS requires 507.3331).

Example 16

(1-butyl)triphenylphosphonium bromide (2.30 g, 5.81 mmol) was dissolved in anhydrous tetrahydrofuran. The reaction medium was cooled to −78° C. and sodium bis (trimethylsilyl) amide (5.81 ml (5.22 g), 5.81 mmol) was added dropwise. The reaction mixture was stirred at 0° C. for 3 h. Thereafter, the mixture was cooled to −78° C. and 2 (1.90 g, 5.81 mmol), pre-dissolved in anhydrous tetrahydrofuran was added. The reaction mixture was stirred at 0° C. for 18 h. The product was extracted with dichloromethane. The organic phase was washed with brine, dried (Na$_2$SO$_4$) and concentrated under diminished pressure. The residue was purified by chromatography on a silica gel column (20×3 cm). Elution with 4:1 hexane/dichloromethane afforded the pure product as a yellow solid: yield 1.30 g (62%); silica gel TLC R$_f$ 0.66 (9:1 hexane/dichloromethane); $^1$H NMR (CDCl$_3$) (500 MHz) δ 1.03 (t, 3H, J=7.2 Hz), 1.57 (s, 11H), 2.42 (q, 2H, J=7 Hz), 5.75 (m, 1H), 6.48 (d, 1H, J=2 Hz), 7.15 (m, 2H), 7.32 (m, 3H), 7.58 (s, 1H) and 7.63 (d, 1H, J=8 Hz); $^{13}$C NMR (CDCl$_3$) (125 MHz) δ 13.60, 22.83, 27.88, 30.38, 81.53, 125.75, 126.19, 126.33, 126.70, 127.07, 127.23, 127.74, 127.81, 129.72, 131.88, 133.23, 136.29, 138.27, 138.51 and 152.07; mass spectrum (APCI), m/z (M+H)$^+$ 368.1680 (C$_{22}$H$_{26}$NO$_2$S requires 368.1684).

The product from the previous step (1.90 g, 5.31 mmol) was dissolved in 7:3 ethanol/dichloromethane and purged under argon gas for 20 minutes. Palladium on carbon (0.11 g, 1.06 mmol) was added. The reaction was done for 2 h under 40 psi pressure in a parahydrogenator. On completion of the reaction, the product was separated from the catalyst by filtration through a celite pad using methanol as the solvent. The product solution was then concentrated under diminished pressure. The residue was purified by chromatography on a silica gel column (20×3 cm). Elution with 4:1 hexane/dichloromethane afforded tert-butyl-2-pentyl-10H-phenothiazine-10-carboxylate (16) as a colourless oil: yield 1.70 g (87%); silica gel TLC R$_f$ 0.62 (9:1 hexane/dichloromethane); $^1$H NMR (CD$_3$OD) (500 MHz) δ 0.76 (s, 3H), 1.16 (s, 4H), 1.32 (s, 9H), 1.45 (s, 2H), 2.41 (s, 2H), 6.77 (s, 1H), 6.94 (s, 1H), 7.05 (m, 2H), 7.14 (s, 1H), 7.23 (s, 1H) and 7.38 (s, 1H); $^{13}$C NMR (CD$_3$OD) (125 MHz) δ 14.61, 23.49, 28.58, 32.14, 32.39, 36.37, 82.85, 127.09, 127.46, 128.00, 128.26, 128.31, 129.94, 133.51, 139.70, 139.90, 142.78 and 153.64; mass spectrum (APCI), m/z (M+H)$^+$ 370.1842 (C$_{22}$H$_{28}$NO$_2$S requires 370.1841).

Example 17

16 (1.70 g, 4.60 mmol) was dissolved in anhydrous dichloromethane. Trifluoroacetic acid (2.81 ml (4.18 g), 36.80 mmol) was added dropwise. The reaction mixture was stirred at room temperature for 18 h. The product was mixed with sodium bicarbonate, extracted with dichloromethane, dried (Na$_2$SO$_4$) and then concentrated under diminished pressure. The residue was purified by chromatography on a silica gel column (20×3 cm). Elution with 9:1 hexane/ethyl acetate afforded 2-pentyl-10H-phenothiazine (17) as a white solid: yield 13 mg (1%); silica gel TLC R$_f$ 0.88 (1:1 hexane/ethylacetate); mass spectrum (APCI), m/z (M+H)$^+$ 270.1315 (C$_{17}$H$_{20}$NS requires 270.1316).

Example 18

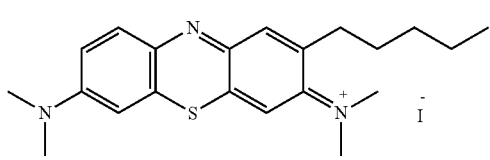

(18)

N-(7-(dimethylamino)-2-pentyl-3H-phenothiazin-3-ylidene)-N-methyl methanaminium iodide 17 (0.18 g, 0.66 mmol) was dissolved in dichloromethane. Iodine (0.54 g, 2.14 mmol) was added and the reaction was run in the dark for 15 minutes. Thereafter, dimethylamine (1.7 ml (1.13 g), 3.34 mmol) was added dropwise and the reaction was allowed to run for 4 h. The product was dissolved in dichloromethane and the solution was concentrated under diminished pressure. The residue was purified by chromatography on a silica gel column (20×3 cm). Elution with at 1:1 methanol/acetonitrile afforded N-(7-(dimethylamino)-2-pentyl-3H-phenothiazin-3-ylidene)-N-methyl methanaminium iodide (18) as a green solid: yield 0.04 g (25%); silica gel TLC $R_f$ 0.23 (acetonitrile); $^1$H NMR (CDCl$_3$) (500 MHz) δ 0.85 (t, 3H, J=6.5 Hz), 1.33 (s, 4H), 1.64 (s, 2H), 2.60 (s, 3H), 2.80 (s, 2H), 3.41 (d, 9H, J=64.5 Hz), 7.29 (s, 2H), 7.79 (d, 2H, J=49.5 Hz) and 8.67 (s, 1H); $^{13}$C NMR (CDCl$_3$) (125 MHz) δ 13.95, 22.38, 29.74, 31.53, 33.89, 34.82, 44.64, 106.93, 111.08, 119.92, 131.55, 135.27, 136.79, 137.03, 137.19, 138.40, 138.75, 153.80 and 157.80; mass spectrum (APCI), m/z (M+2H)$^+$ 356.2170 (C$_{21}$H$_{30}$N$_3$S requires 356.2160); ultraviolet/visible spectrum $\lambda_{max}$ 665.0 nm (in dichloromethane), $\lambda_{max}$ 665.0 nm (in methanol).

Example 19

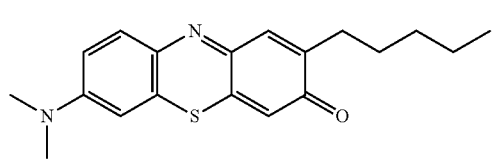

(19)

7-(dimethylamino)-2-pentyl-3H-phenothiazin-3-one 18 (0.65 g, 1.85 mmol) was dissolved in a mixture of tetrahydrofuran/water (6:1). Solid KOH (0.10 g, 1.85 mmol) was added and the reaction mixture was heated and stirred until the reaction mixture changed colour from green to red. The reaction was quenched with water. The product was extracted in ethyl acetate, washed with brine, dried (Na$_2$SO$_4$) and was concentrated under diminished pressure. The residue was purified by chromatography on a silica gel column (20×1 cm). Elution with ethylacetate afforded 7-(dimethylamino)-2-pentyl-3H-phenothiazin-3-one (19) as a red solid: yield 0.02 g (5%); silica gel TLC $R_f$ 0.16 (4:1 hexane/ethyl acetate); $^1$H NMR (CDCl$_3$) (400 MHz) δ 0.91 (t, 3H, J=7 Hz), 1.37 (m, 4H), 1.71 (m, 2H), 2.70 (t, 2H, J=8 Hz), 2.87 (s, 4H), 6.71 (d, 1H, J=2 Hz), 6.88 (dd, 1H, J=2.2 Hz), 6.91 (s, 1H), 7.58 (d, 1H, J=10 Hz) and 7.70 (s, 1H); $^{13}$C NMR (CDCl$_3$) (100 MHz) δ 14.18, 22.69, 29.79, 31.59, 31.99, 44.02, 112.83, 119.27, 123.32, 133.98, 134.56, 135.45, 136.39, 139.71, 143.29, 155.83 and 182.44; mass spectrum (APCI), m/z (M+H)$^+$ 327.1534 (C$_{19}$H$_{23}$N$_2$OS requires 327.1531); ultraviolet/visible spectrum $\lambda_{max}$ 545.0 nm (in dichloromethane), $\lambda_{max}$ 570.0 nm (in methanol).

Example 20

(1-decyl)triphenylphosphonium bromide (0.79 g, 1.64 mmol) was dissolved in anhydrous tetrahydrofuran. The reaction medium was cooled to −78° C. and sodium bis(trimethylsilyl) amide (1.64 ml (1.47 g), 1.64 mmol) was added dropwise. The reaction mixture was stirred at 0° C. for 3 h. Thereafter, the mixture was cooled to −78° C. and 2 (0.53 g, 1.64 mmol), pre-dissolved in anhydrous tetrahydrofuran was added. The reaction mixture was stirred at 0° C. for 18 h. The product was extracted with dichloromethane. The organic phase was washed with brine, dried (Na$_2$SO$_4$) and concentrated under diminished pressure. The residue was purified by chromatography on a silica gel column (20×1 cm). Elution with 4:1 hexane/dichloromethane afforded the pure product as a yellow solid: yield 0.14 g (20%); $^1$H NMR (CDCl$_3$) (400 MHz) δ 0.93 (t, 3H, J=6.4 Hz), 1.31 (s, 13H), 1.53 (s, 10H), 2.38 (q, 2H, J=7 Hz), 5.71 (m, 1H), 6.40 (d, 1H, J=11.2 Hz), 7.13 (m, 2H), 7.28 (q, 2H, J=7.4 Hz), 7.35 (d, 1H, J=7.6 Hz), 7.49 (s, 1H) and 7.57 (d, 1H, J=7.6 Hz); $^{13}$C NMR (CDCl$_3$) (100 MHz) δ 14.26, 22.84, 27.36, 28.32, 29.48, 29.73, 29.78, 29.93, 30.07, 32.07, 82.10, 126.14, 126.64, 127.36, 127.54, 127.81, 127.90, 129.99, 130.02, 130.06, 132.34, 134.01, 136.79, 138.65, 138.92 and 152.59; mass spectrum (APCI), m/z (M+H)$^+$ 452.2617 (C$_{28}$H$_{38}$NO$_2$S requires 452.2623).

The pure product from the previous step (0.85 g, 1.88 mmol) was dissolved in 7:3 ethanol/dichloromethane and purged under argon gas for 20 minutes. Palladium on carbon (0.04 g, 0.37 mmol) was added. The reaction was done for 2 h under 40 psi pressure in a parahydrogenator. On completion of the reaction, the product was separated from the catalyst by filtration through a celite pad using methanol as the solvent. The product solution was then concentrated under diminished pressure. The residue was purified by chromatography on a silica gel column (20×1 cm). Elution with 4:1 hexane/dichloromethane afforded tert-butyl-2-undecyl-10H-phenothiazine-10-carboxylate (20) as a colourless oil: yield 0.54 g (80%); $^1$H NMR (CDCl$_3$) (500 MHz) δ 0.97 (t, 3H, J=6.7 Hz), 1.35 (s, 16H), 1.56 (s, 8H), 1.69 (m, 2H), 2.67 (t, 2H, J=7.7 Hz), 7.02 (d, 1H, J=8 Hz), 7.16 (t, 1H, J=7.7 Hz), 7.28 (d, 2H, J=8 Hz), 7.37 (d, 1H, J=8 Hz), 7.44 (s, 1H) and 7.60 (d, 1H, J=7.5 Hz); $^{13}$C NMR (CDCl$_3$) (125 MHz) δ 14.12, 22.69, 28.17, 29.28, 29.34, 29.51, 29.57, 29.64, 29.67, 31.49, 31.92, 35.58, 81.70, 125.88, 126.27, 126.99, 127.06, 127.11, 127.19, 127.36, 128.79, 132.46, 138.65, 138.86, 141.67 and 152.41; mass spectrum (APCI), m/z (M+H)$^+$ 454.2772 (C$_{28}$H$_{40}$NO$_2$S requires 454.2780).

Example 21

20 (0.82 g, 1.81 mmol) was dissolved in anhydrous dichloromethane. Trifluoroacetic acid (1.10 ml (1.63 g), 14.48 mmol) was added dropwise. The reaction mixture was stirred at room temperature for 18 h. The product was mixed with sodium bicarbonate, extracted with dichloromethane, dried (Na$_2$SO$_4$) and then concentrated under diminished pressure. The residue was purified by chromatography on a silica gel column (20×1 cm). Elution with 9:1 hexane/ethyl acetate afforded 2-undecyl-10H-phenothiazine (21) as a white solid: yield 0.13 g (100%); mass spectrum (APCI), m/z (M+H)+ 354.2252 ($C_{23}H_{32}NS$ requires 354.2255).

Example 22

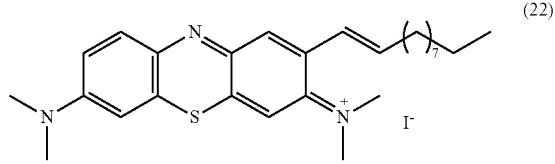

N-(7-(dimethylamino)-2-undecyl-3H-phenothiazin-3-ylidene)-N-methyl methanaminium iodide 21 (1.40 g, 4.00 mmol) was dissolved in dichloromethane. Iodine (3.20 g, 12.90 mmol) was added and the reaction was run in the dark for 15 minutes. Thereafter, dimethylamine (10.10 ml (6.70 g), 20.30 mmol) was added dropwise and the reaction was allowed to run for 4 h. The product was dissolved in dichloromethane and the solution was concentrated under diminished pressure. The residue was purified by chromatography on a silica gel column (20×3 cm). Elution with methanol afforded N-(7-(dimethylamino)-2-undecyl-3H-phenothiazin-3-ylidene)-N-methyl methanaminium iodide (22) as a green solid: yield 0.10 g (25%); silica gel TLC $R_f$ 0.07 (methanol); $^1$H NMR (CDCl$_3$) (500 MHz) δ 0.88 (t, 3H, J=6.7 Hz), 1.26 (s, 18H), 1.72 (m, 2H), 2.85 (t, 2H, J=7.7 Hz), 3.35 (s, 4H), 3.46 (s, 4H), 3.56 (s, 1H), 7.28 (d, 1H, J=12.5 Hz), 7.37 (s, 1H), 7.39 (s, 1H), 7.87 (s, 1H) and 7.97 (d, 1H, J=10 Hz); $^{13}$C NMR (CDCl$_3$) (125 MHz) δ 14.25, 22.79, 29.45, 29.59, 29.68, 29.71, 29.73, 30.26, 32.01, 34.28, 42.57, 44.88, 106.88, 111.25, 119.95, 132.00, 135.74, 137.12, 137.30, 137.49, 138.71, 138.89, 154.21 and 158.23; mass spectrum (APCI), m/z (M+2H)+ 440.3087 ($C_{27}H_{42}N_3S$ requires 440.3099); ultraviolet/visible spectrum $\lambda_{max}$ 669.9 nm (in dichloromethane), $\lambda_{max}$ 665.0 nm (in methanol).

Example 23

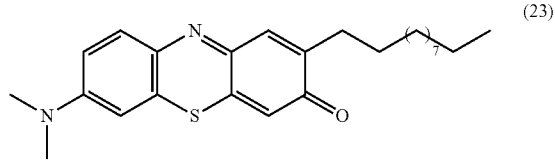

7-(dimethylamino)-2-undecyl-3H-phenothiazin-3-one 22 (0.08 g, 0.18 mmol) was dissolved in a mixture of tetrahydrofuran/water (6:1). Solid KOH (0.01 g, 0.18 mmol) was added and the reaction mixture was stirred for 10 minutes when the colour changed from green to red. The reaction was quenched with water. The product was extracted in ethyl acetate, washed with brine, dried (Na$_2$SO$_4$) and was concentrated under diminished pressure. The residue was purified by chromatography on a silica gel column (20×1 cm). Elution with 4:1 hexane/ethylacetate afforded 7-(dimethylamino)-2-undecyl-3H-phenothiazin-3-one (23) as a red solid: yield 0.007 g (13%); silica gel TLC $R_f$ 0.85 (ethyl acetate); $^1$H NMR (CDCl$_3$) (500 MHz) δ 0.87 (t, 3H, J=7 Hz), 1.26 (s, 18H), 1.70 (m, 2H), 2.70 (t, 2H, J=8 Hz), 2.86 (s, 5H), 6.72 (d, 1H, J=2 Hz), 6.88 (dd, 1H, J=2 Hz), 6.92 (s, 1H), 7.58 (d, 1H, J=9.5 Hz) and 7.70 (s, 1H); $^{13}$C NMR (CDCl$_3$) (125 MHz) δ 14.26, 22.84, 29.49, 29.63, 29.72, 29.80, 30.11, 31.64, 32.08, 44.01, 44.05, 112.82, 119.24, 119.27, 123.35, 133.97, 134.57, 135.47, 136.42, 139.75, 143.28, 155.84 and 182.45; mass spectrum (APCI), m/z (M+H)+ 411.2463 ($C_{25}H_{35}N_2OS$ requires 411.2470); ultraviolet/visible spectrum $\lambda_{max}$ 554.9 nm (in dichloromethane), $\lambda_{max}$ 565.0 nm (in methanol).

Example 24

(1-decyl)triphenylphosphonium bromide (0.79 g, 1.64 mmol) was dissolved in anhydrous tetrahydrofuran. The reaction medium was cooled to −78° C. and sodium bis (trimethylsilyl) amide (1.64 ml (1.47 g), 1.64 mmol) was added dropwise. The reaction mixture was stirred at 0° C. for 3 h. Thereafter, the mixture was cooled to −78° C. and 2 (0.53 g, 1.64 mmol), pre-dissolved in anhydrous tetrahydrofuran was added. The reaction mixture was stirred at 0° C. for 18 h. The product was extracted with dichloromethane. The organic phase was washed with brine, dried (Na$_2$SO$_4$) and concentrated under diminished pressure. The residue was purified by chromatography on a silica gel column (20×1 cm). Elution with 4:1 hexane/dichloromethane afforded (E)-tert-butyl-2-(undec-1-enyl)-10H-phenothiazine-10-carboxylate (24) as a yellow solid: yield 0.14 g (20%); $^1$H NMR (CDCl$_3$) (400 MHz) δ 0.93 (t, 3H, J=6.4 Hz), 1.31 (s, 13H), 1.53 (s, 10H), 2.38 (q, 2H, J=7 Hz), 5.71 (m, 1H), 6.40 (d, 1H, J=11.2 Hz), 7.13 (m, 2H), 7.28 (q, 2H, J=7.4 Hz), 7.35 (d, 1H, J=7.6 Hz), 7.49 (s, 1H) and 7.57 (d, 1H, J=7.6 Hz); $^{13}$C NMR (CDCl$_3$) (100 MHz) δ 14.26, 22.84, 27.36, 28.32, 29.48, 29.73, 29.78, 29.93, 30.07, 32.07, 82.10, 126.14, 126.64, 127.36, 127.54, 127.81, 127.90, 129.99, 130.02, 130.06, 132.34, 134.01, 136.79, 138.65, 138.92 and 152.59; mass spectrum (APCI), m/z (M+H)+ 452.2617 ($C_{28}H_{38}NO_2S$ requires 452.2623).

Example 25

24 (0.65 g, 1.45 mmol) was dissolved in anhydrous dichloromethane. Trifluoroacetic acid (0.88 ml (1.31 g), 11.60 mmol) was added dropwise. The reaction mixture was stirred at room temperature for 18 h. The product was mixed with sodium bicarbonate, extracted with dichloromethane, dried (Na$_2$SO$_4$) and then concentrated under diminished pressure. The residue was purified by chromatography on a silica gel column (20×1 cm). Elution with 9:1 hexane/ethyl acetate afforded (E)-2-(undec-1-enyl)-10H-phenothiazine (25) as a white solid: yield 0.21 g (100%).

Example 26

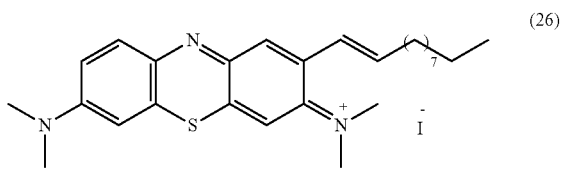

N-(7-(dimethylamino)-(E)-2-(undec-1-enyl)-3H-phenothiazin-3-ylidene)-N-methyl methanaminium iodide 25 (0.45 g, 1.30 mmol) was dissolved in dichloromethane. Iodine (1.10 g, 4.10 mmol) was added and the reaction was run in the dark for 15 minutes. Thereafter, dimethylamine (3.30 ml (2.21 g), 6.50 mmol) was added dropwise and the reaction was allowed to run for 4 h. The product was dissolved in dichloromethane and the solution was concentrated under diminished pressure. The crude product N-(7-(dimethylamino)-(E)-2-(undec-1-enyl)-3H-phenothiazin-3-ylidene)-N-methyl methanaminium iodide (26) was obtained as a green solid. Mass spectrum (MALDI-TOF), m/z (M$^+$) 436.696 ($C_{27}H_{38}N_3S$ requires 436.2781).

Example 27

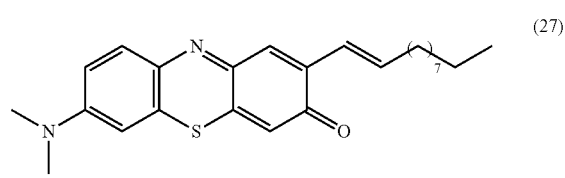

7-(dimethylamino)-(E)-2-(undec-1-enyl)-3H-phenothiazin-3-one 26 (0.19 g, 0.43 mmol) was dissolved in a mixture of tetrahydrofuran/water (6:1). Solid KOH (0.025 g, 0.43 mmol) was added and the reaction mixture was stirred for 10 minutes when the colour changed from green to red. The reaction was quenched with water. The product was extracted in ethyl acetate, washed with brine, dried ($Na_2SO_4$) and was concentrated under diminished pressure. The crude product 7-(dimethylamino)-(E)-2-(undec-1-enyl)-3H-phenothiazin-3-one (27) was obtained as a red solid. Mass spectrum (MALDI-TOF), m/z (M$^+$) 408.736 ($C_{25}H_{32}N_2OS$ requires 408.2235).

Examples 28-32

Examples 28-32 shown below in Table 1, are prepared essentially according to the synthetic methodology described herein, and/or by using methodology well known in the art.

TABLE 1

| Ex. No. | Chemical Structure |
|---|---|
| 28 | 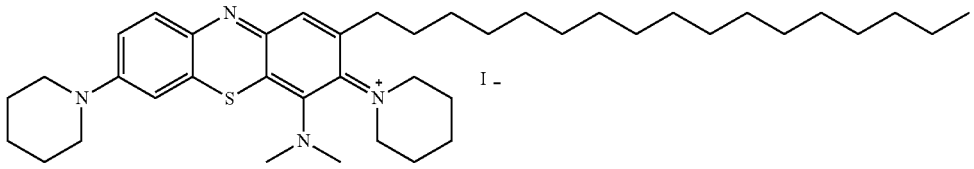 [SMILES: CCCCCCCCCCCCCCCCCc1cc2nc3ccc(N4CCCCC4)cc3sc-2c(N(C)C)c1=[N+]1CCCCC1 ; [I-]] |
| 29 | 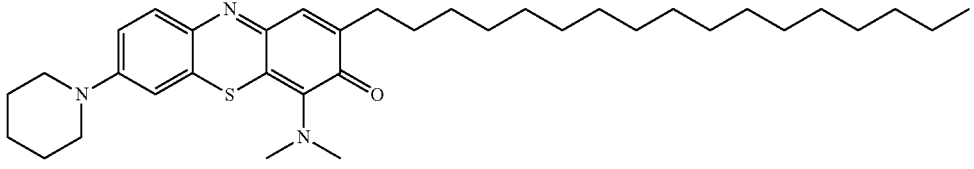 [SMILES: CCCCCCCCCCCCCCCCCc1cc2nc3ccc(N4CCCCC4)cc3sc-2c(N(C)C)c1=O] |
| 30 | 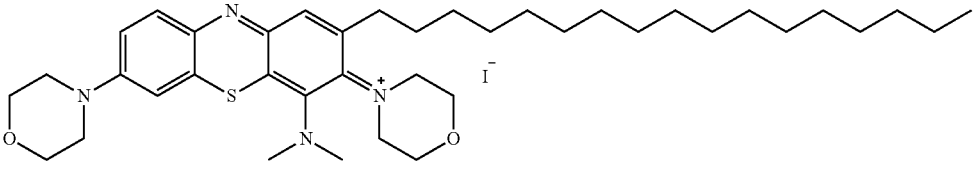 [SMILES: CCCCCCCCCCCCCCCCCc1cc2nc3ccc(N4CCOCC4)cc3sc-2c(N(C)C)c1=[N+]1CCOCC1 ; [I-]] |
| 31 | 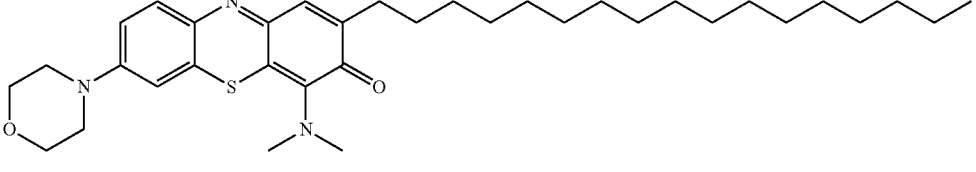 |
| 32 | 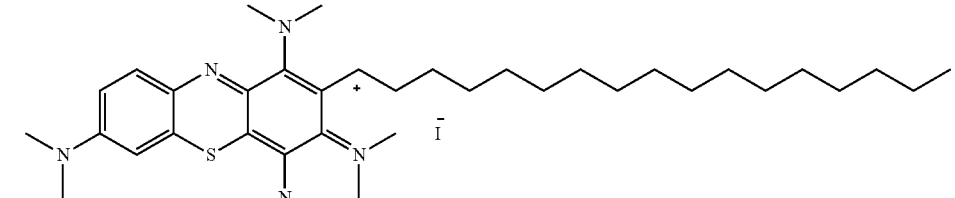 |

Example 33

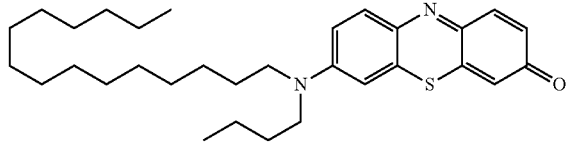

7-(butyl(pentadecyl)amino)-3H-phenothiazin-3-one 2-(2,4-Dinitrophenyl)thio)-5-methoxyaniline (34): 2.00 g (11.1 mmol) of 2-amino-6-methoxybenzothiazole was suspended in 40 ml of water and 9.30 g (167 mmol) of solid KOH was added. The suspension was heated to reflux for 12 h. The reaction mixture was cooled to room temperature and added dropwise to a solution of 2.25 g (11.1 mmol) of 2,4-dinitrochlorobenzene in a mixture of ethanol (30 mL)-AcOH (20 mL) in ice-water bath. The reaction mixture was stirred at room temperature for an additional 3 h. The precipitate was filtered, washed with water-ethanol (1:1, v/v) and dried to afford 34 as an orange solid: yield 2.90 g (81%); silica gel TLC $R_f$ 0.7 (3:7 ethyl acetate-hexanes); $^1$H NMR (CD$_3$COCD$_3$) δ 3.76 (s, 3H), 6.85 (d, 1H, J=8.8 Hz), 6.97 (d, 1H, J=2.8 Hz), 7.00-7.06 (m, 2H), 8.18 (dd, 1H, J=9.2 Hz, J=2.6 Hz) and 9.12 (d, 1H, J=2.4 Hz); $^{13}$C NMR (DMSO-d$_6$) δ 55.9, 111.0, 117.5, 120.4, 120.6, 121.6, 127.1, 128.6, 143.3, 144.4, 144.6, 145.8 and 153.0; mass spectrum (APCI), m/z 322.0499 (M+H)$^+$ (C$_{13}$H$_{12}$N$_3$O$_5$S requires m/z 322.0498).

N-(2-((2,4-Dinitrophenyl)thio)-5-methoxyphenyl)acetamide (35): To a solution of 2.90 g (9.03 mmol) of 34 in 10 mL of anhydrous DMF was added 3.66 mL (2.74 g, 27.1 mmol) of anhydrous triethylamine followed by 4.30 mL (4.64 g, 45.5 mmol) of acetic anhydride. The reaction mixture was stirred for 12 h at room temperature and quenched by pouring into ice-cold water. The aqueous layer was extracted with four 25-mL portions of ethyl acetate. The combined organic layer was dried over anhydrous MgSO$_4$, filtered and concentrated under diminished pressure. The residue was purified on a silica gel column (8×4 cm). Elution with 3:7 ethyl acetate-hexanes afforded 35 as a bright yellow solid: yield 2.95 g (90%); silica gel TLC $R_f$ 0.57 (3:7 ethyl acetate-hexanes); $^1$H NMR (DMSO-d$_6$) δ 1.86 (s, 3H), 3.77 (s, 3H), 6.99 (d, 1H, J=8.8 Hz), 7.18 (dd, 1H, J=8.8 Hz, J=2.4 Hz), 7.23 (d, 1H, J=2.8 Hz), 7.66 (d, 1H, J=8.8 Hz), 8.32 (dd, 1H, J=9.0 Hz, J=2.6 Hz), 8.88 (d, 1H, J=2.4 Hz) and 9.43 (br s, 1H); $^{13}$C NMR (DMSO-d$_6$) δ 22.8, 55.6, 117.7, 120.5, 121.0, 123.8, 127.5, 128.1, 129.2, 133.7, 144.05, 144.07, 145.6, 157.2 and 168.7; mass spectrum (APCI), m/z 364.0609 (M+H)$^+$ (C$_{15}$H$_{14}$N$_3$O$_6$S requires m/z 364.0603).

3-Methoxy-7-nitro-10H-phenothiazine (36): To a stirred solution of 2.95 g (8.13 mmol) of 35 in 20 mL of acetone, under reflux, was added 0.91 g (16.2 mmol) of KOH in portions. The reaction mixture was kept under reflux for an additional 3 h and poured into ice-cold water. The aqueous layer was extracted with four 25-mL portions of ethyl acetate. The combined organic layer was dried over anhydrous MgSO$_4$, filtered and concentrated under diminished pressure. The residue was purified on a silica gel column (8×2 cm). Elution with 1:1 ethyl acetate-hexanes gave 36 as a violet solid: yield 2.00 g (90%); silica gel TLC $R_f$ 0.43 (3:7 ethyl acetate-hexanes); $^1$H NMR (CD$_3$COCD$_3$) δ 3.70 (s, 3H), 6.57-6.70 (m, 4H), 7.73 (d, 1H, J=2.4 Hz), 7.81-7.84 (m, 1H) and 8.47 (br s, 1H); $^{13}$C NMR (CD$_3$COCD$_3$) δ 55.0, 111.7, 113.0, 113.3, 116.1, 117.0, 117.2, 121.6, 124.2, 132.4, 141.5, 148.3 and 156.6; mass spectrum (APCI), m/z 275.0488 (M+H)$^+$ (C$_{13}$H$_{11}$N$_2$O$_3$S requires m/z 275.0490).

tert-Butyl 3-Methoxy-7-nitro-10H-phenothiazin-10-carboxylate (37): To a solution of 1.42 g (5.18 mmol) of 36 in 20 mL of anhydrous DMF at 0° C. was added 0.55 g (13.7 mmol) of 60% NaH. The reaction mixture was stirred at 0° C. for another 15 mins and 2.40 g (11.0 mmol) of di-tert-butyl dicarbonate was added. The reaction mixture was stirred at room temperature for 4 h, and was quenched with 30 mL of water. The aqueous layer was extracted with three 20-mL portions of ethyl acetate. The combined organic layer was washed with 20 mL of brine, dried over anhydrous MgSO$_4$ and concentrated under diminished pressure. The residue was purified on a silica gel column (8×4 cm). Elution with 3:7 ethyl acetate-hexanes afforded 37 as a bright yellow solid: yield 1.66 g (86%); silica gel TLC $R_f$ 0.54 (3:7 ethyl acetate-hexanes); $^1$H NMR (CD$_3$COCD$_3$) δ 1.54 (s, 9H), 3.86 (s, 3H), 6.97 (dd, 1H, J=9.2 Hz, J=2.8 Hz), 7.01 (d, 1H, J=2.8 Hz), 7.47 (d, 1H, J=9.2 Hz), 7.84 (d, 1H, J=8.8 Hz), 8.20 (dd, 1H, J=9.0 Hz, J=2.6 Hz) and 8.24 (d, 1H, J=2.4 Hz); $^{13}$C NMR (CD$_3$COCD$_3$) δ 29.2, 57.1, 84.3, 113.3, 115.6, 123.7, 124.1, 129.8, 130.0, 132.3, 133.1, 135.3, 146.9, 147.1, 153.2 and 159.9; mass spectrum (APCI), m/z 374.0932 (M+H)$^+$ (C$_{18}$H$_{19}$N$_2$O$_5$S requires m/z 374.0936).

tert-Butyl 3-Amino-7-methoxy-10H-phenothiazin-10-carboxylate (38): To a suspension of 0.42 g (1.12 mmol) of 37 in 10 mL of ethanol was added 10 mg of 10% Pd on activated carbon. The reaction mixture was stirred at room temperature under hydrogen atmosphere (25 psi) overnight. The reaction mixture was filtered through a celite pad and concentrated under diminished pressure. The crude product (38) was used for the next reaction without further purification.

tert-Butyl 3-(Pentadecylamino)-7-methoxy-10H-phenothiazin-10-carboxylate (39): 2.11 g (7.25 mmol) of 1-bromopentadecane in 3 mL of acetonitrile was added into a mixture of 0.50 g (~1.45 mmol) of crude compound 38 in 2 mL of acetonitrile and 1.55 g (14.6 mmol) of Na$_2$CO$_3$. The reaction mixture was sealed under nitrogen atmosphere and stirred at 80° C. for ~3 days. The reaction mixture was cooled to room temperature and filtered. The filtrate was concentrated under diminished pressure and purified on a silica gel column. Elution with 1:9 ethyl acetate-hexanes gave compound 39 as a pale yellow solid: yield 0.14 g (9%); silica gel TLC $R_f$ 0.31 (1:9 ethyl acetate-hexanes) $^1$H NMR (CDCl$_3$) δ 0.87 (t, 3H, J=6.6 Hz), 1.25 (br s, 24H), 1.45 (s, 9H), 1.52-1.57 (m, 2H), 3.04 (t, 2H, J=7.2 Hz), 3.76 (s, 3H), 6.45 (dd, 1H, J=8.6 Hz, J=2.6 Hz), 6.50 (d, 1H, J=2.8 Hz), 6.76 (dd, 1H, J=8.8 Hz, J=2.8 Hz), 6.83 (d, 1H, J=2.8 Hz), 7.24 (d, 1H, J=8.4 Hz) and 7.36 (d, 1H, J=8.8 Hz); $^{13}$C NMR (CDCl$_3$) δ 14.2, 22.8, 27.2, 28.20, 28.27, 28.31, 28.4, 29.46, 29.5, 29.69, 29.70, 29.75, 29.8, 32.0, 44.2, 55.7, 81.4, 109.8, 111.65, 111.7, 112.8, 127.6, 127.8, 128.7, 132.5, 132.7, 133.3, 146.7, 153.3 and 157.3; mass spectrum (APCI), m/z 555.3629 (M+H)$^+$ (C$_{33}$H$_{51}$N$_2$O$_3$S requires m/z 555.3620).

tert-Butyl 3-(Butylpentadecylamino)-7-methoxy-10H-phenothiazin-10-carboxylate (40): 0.11 mL (0.14 g, 1.00 mmol) of 1-bromobutane was added into a mixture of 90.0 mg (0.16 mmol) of compound 39 in 2 mL of acetonitrile and 0.17 g (1.60 mmol) of Na$_2$CO$_3$. The reaction mixture was sealed under nitrogen atmosphere and stirred at 80° C. for ~30 h. The reaction mixture was cooled to room temperature and filtered. The filtrate was concentrated under diminished pressure. The crude was used to the next step without further purification.

7-(Butylpentadecylamino)-3H-phenothiazin-3-one (33). 0.48 mL (0.48 mmol) of 1 M BBr$_3$ in CH$_2$Cl$_2$ was added dropwise into the solution of 100 mg (~0.16 mmol) of crude compound 40 in 2 mL of CH$_2$Cl$_2$ at −78° C. The reaction mixture was stirred overnight at ambient temperature and was quenched with 10 mL of water. The product was extracted with two 10-mL portions of ethyl acetate. The combined organic layer was washed with 20 mL of brine, dried over anhydrous Na$_2$SO$_4$ and concentrated under reduced pressure. The resulting violet solid was purified on a silica gel column (7×2 cm). Elution with 3:7 ethyl acetate-hexanes afforded 33 as a violet solid: yield 20 mg (25%); silica gel TLC R$_f$0.50 (1:4 ethyl acetate-hexanes); $^1$H NMR (CDCl$_3$) δ 0.88 (t, 3H, J=6.6 Hz), 1.00 (t, 3H, J=7.2 Hz), 1.26-1.43 (m, 26H), 1.62-1.64 (m, 4H), 3.36-3.41 (m, 4H), 6.55 (d, 1H, J=2.4 Hz), 6.71 (s, 1H), 6.79-6.85 (m, 2H), 7.57 (d, 1H, J=9.6 Hz) and 7.68 (d, 1H, J=9.2 Hz); $^{13}$C NMR (CDCl$_3$) δ 14.3, 22.8, 27.1, 27.5, 29.50, 29.53, 29.6, 29.7, 29.77, 29.79, 29.81, 29.83, 32.1, 51.5, 104.8, 113.3, 118.7, 128.7, 131.0, 132.4, 134.9, 136.0, 139.6, 140.0, 150.0 and 182.4; mass spectrum (APCI), m/z 495.3330 (M+H)$^+$ (C$_{31}$H$_{47}$N$_2$OS requires m/z 495.3331).

Biological Example 1

Biochemical and Biological Evaluation

Cell Lines and Culture Conditions

Human mitochondrial disease cell line, Friedreich's ataxia lymphocytes (GM15850) was obtained from Coriell Cell Repositories (Camden, N.J.). Lymphocytes were cultured in RPMI-1640 medium (Gibco, Life Technologies, Grand Island, N.Y.) with 15% fetal calf serum, 2 mM glutamine (HyClone, South Logan, Utah) and 1% penicillin-streptomycin antibiotic supplement (Cellgro, Manassas, Va.). Cells were passaged every other day to maintain them in log phase growth and kept at a nominal concentration of 5-10×10$^5$ cell/mL. A CoQ$_{10}$ deficient lymphocyte cell line (GM17932) was obtained from Coriell Cell Repositories. A nutrient sensitized screening strategy to identify methylene blue analogues that function within the mitochondrial respiratory chain was used by growing the CoQ$_{10}$-deficient or FRDA lymphocytes in galactose containing media to force energy production predominantly through oxidative phosphorylation rather than glycolysis.[1-4] The lymphocytes were cultured in RPMI 1640 glucose free medium (Gibco, Grand Island, N.Y.) supplemented with 25 mM galactose, 2 mM glutamine and 1% penicillin-streptomycin, and 10% dialyzed fetal bovine serum (FBS) (<0.5 μg/mL) (Gemini Bio-Product, West Sacramento, Calif.).

Cytotoxicity Assay

Evaluation of methylene blue analogues for their cytoxicity and their ability to function within the mitochondrial respiratory chain was carried out by incubation of the prepared compounds for 24 or 48 h with FRDA lymphocytes. We have used a nutrient-sensitized screening strategy by culturing FRDA cells in galactose as the sole sugar source which forces mammalian cells to rely on mitochondrial oxidative phosphorylation (OXPHOS) to produce their ATP; they also become more sensitive to mitochondrial respiratory chain inhibitors than cells grown in glucose medium. Methylene blue analogues were tested for their cytotoxicity in FRDA lymphocytes using a simultaneous staining with a two-color fluorescence assay, the Live/Dead® Viability/Cytotoxicity Kit (Molecular Probes). This assay is used to measure two recognized parameters of cell viability, intracellular esterase activity and plasma integrity. The membrane-impermeant DNA dye ethidium homodimer-1 (EthD-1) was used to identify dead cells whose plasma membrane integrity was disrupted. The membrane-permeant dye calcein-AM was used to label live cells. It penetrates into the cells where it is metabolized by cytoplasmic esterases and becomes a fluorescent but membrane-impermeant probe which is retained in viable cells. One mL of FRDA lymphocyte cells (5×10$^5$ cells) was plated in a 24-well plate in glucose free media (galactose 25 mM), treated with the test compounds and incubated at 37° C. for 24 h or 48 h in a humidified atmosphere containing 5% CO$_2$ in air. Cells were collected by centrifugation at 300× g for 3 min and washed with phosphate buffered saline. Cells were resuspended in phosphate buffered saline containing 25 mM galactose. Cell suspension was stained with 0.1 μM calcein AM and 0.2 μM EthD-1 and incubated in the dark at 37° C. for 15 minutes. Cells were collected by centrifugation at 300× g for 3 min and then washed with PBS. The samples were analyzed immediately by flow cytometry (C6 Accuri, BD Biosciences, San Jose, Calif.), using a 488 nm excitation laser and the and the FL1-H channel 530±15 nm emission filter and the FL2-H channel 585±15 nm. For each analysis 10,000 events were recorded and analyzed using C6 Accuri software (BD Biosciences).

Suppression of Reactive Oxygen Species

The ability of the methylene blue analogues to suppress ROS induced by depletion of glutathione was evaluated in FRDA lymphocyte cells. The intracellular ROS level was measured based on the ROS-induced formation of the highly fluorescent product 2',7'-dichlorofluorescein (DCF) from the non-fluorescent dye 2',7'-dichlorodihydrofluorescein diacetate (DCFH-DA). Briefly, 1 mL of FRDA lymphocytes (5×10$^5$ cells) was plated in a 24-well plate, treated with the test compounds and incubated at 37° C. for 16 h in a humidified atmosphere containing 5% CO$_2$ in air. Cells were treated with 5 mM diethyl maleate (DEM) for 80 min, collected by centrifugation at 300× g for 3 min and then washed with phosphate buffered saline (Life Technologies). Cells were resuspended in PBS containing 20 mM glucose and incubated at 37° C. in the dark for 25 min with 10 μM DCFH-DA. Cells were collected by centrifugation at 300× g for 3 min and then washed with PBS. The samples were analyzed immediately by flow cytometry (C6 Accuri, BD Biosciences, San Jose, Calif.), using a 488 nm excitation laser and the FL1-H channel 530±15 nm emission filter. The generation of ROS, mainly peroxides, was detected as a result of the oxidation of DCFH. In each analysis, 10,000 events were recorded after cell debris was electronically gated out. Results obtained were verified by running duplicates and repeating experiments in three independent runs. Results were expressed as a percentage of median fluorescent intensity relative to FRDA-treated control.

Preservation of Mitochondrial Membrane Potential ($\Delta\psi_m$)

The ability of the test compounds to depolarize or maintains mitochondrial inner membrane potential ($\Delta\psi_m$) was assessed using the JC-1 probe. JC-1 is a cationic dye which exhibits potential-dependent accumulation in mitochondria. JC-1 is a dual stain, which can identify high membrane potential through J-aggregates (red fluorescence) and low membrane potential through J-monomers (green fluorescence). When the $\Delta\psi_m$ collapses, the reagent (JC-1) no longer accumulates inside the mitochondria; instead, it is diffuses throughout the cell cytosol in the monomeric form which fluoresces green. The detection of mitochondrial depolarization using JC-1 was accomplished by flow cytometry as described before (Arce et al. (2012) *Bioorg. Med. Chem.* 20, 5188). Briefly, FRDA lymphocytes cells ($5\times10^5$ cells) were pre-treated with or without the test compounds for 16 h. The cells were incubated at 37° C. in the dark for 20 min with 1 µM JC-1. Cells were collected by centrifugation at 300× g for 3 min and washed with phosphate buffered saline. Cells were resuspended in phosphate buffered saline supplemented with 20 mM glucose and were analyzed immediately by FACS (C6 Accuri, BD Biosciences, San Jose, Calif.), using a 488 nm excitation laser and the FL1-H channel 530±15 nm emission filter and the FL2-H channel 585±15 nm. For each analysis 10,000 events were recorded and analyzed using C6 Accuri software (BD Biosciences). FCCP (carbonyl cyanide p-trifluoromethoxyphenyl hydrazone), a mitochondrial uncouple, was used to produce a negative control.

Cellular ATP Levels

A nutrient-sensitized screening strategy to identify methylene blue analogues that function within the mitochondrial respiratory chain and augment ATP was used as described before (Khdour et al. (2013) *ACS Med. Chem. Lett.* 4, 724). The intracellular ATP level was measured in glucose-free media. The cells were grown on galactose-containing media to maximize ATP production via oxidative phosphorylation, and they become more sensitive to mitochondrial respiratory chain inhibitors than cells grown on glucose medium. While we have not identified any of these compounds which reliably increase ATP levels in cultured cells, as we had found previously for pyrimidinol analogues, we did verify that none of the analogues being considered for further study significantly decreased ATP production, thereby avoiding mitochondrial toxins. Briefly FRDA lymphocytes ($2\times10^5$ cell/mL) were plated (1 mL in 24-well plates) in glucose-free media supplemented with galactose and treated with the test compounds at final concentrations of 250, 300, 2500 and 5000 nM, and then incubated at 37° C. for 24 h or 48 h in a humidified atmosphere containing 5% $CO_2$ in air. Wells were mixed and cells in each well were transferred (100 µL) to 96-well microtiter black-walled cell culture plates (Costar, Corning, N.Y.). The total intracellular ATP level was measured in a luminator (Clarity™ luminescence microplate reader) using an ATP Bioluminescence Assay Kit (ViaLight-Plus ATP monitoring reagent kit, Lonza, Walkersville, Md.) following the manufacturer's protocol. The total ATP level was expressed as a percentage of untreated control.

Cytoprotection

The cytoprotection conferred by the prepared compounds was determined in FRDA lymphocyte using a simultaneous staining with a two-color fluorescence assay, the Live/Dead® Viability/Cytotoxicity Kit (Molecular Probes). One mL of FRDA lymphocyte cells ($5\times10^5$ cells) was plated in a 24-well plate in glucose free media (galactose 25 mM), treated with the test compounds and incubated at 37° C. for 4 h. Cells were treated with 50 nM rotenone and incubated at 37° C. for 24 h or 48 h in a humidified atmosphere containing 5% $CO_2$ in air. Cells were collected by centrifugation at 300× g for 3 min and washed with phosphate buffered saline. Cells were resuspended in phosphate buffered saline containing 25 mM galactose. Cell suspension was stained with 0.1 µM calcein AM and 0.2 µM EthD-1 and incubated in the dark at 37° C. for 15 minutes. Cells were collected by centrifugation at 300× g for 3 min and then washed with PBS. The samples were analyzed immediately by flow cytometry (C6 Accuri, BD Biosciences, San Jose, Calif.), using a 488 nm excitation laser and the and the FL1-H channel 530±15 nm emission filter and the FL2-H channel 585±15 nm. For each analysis 10,000 events were recorded and analyzed using C6 Accuri software (BD Biosciences).

NADH Oxidase Activity

The effect of the methylene blue analogues on the activities of complexes I, III and IV within the respiratory chain was evaluated using bovine heart mitochondria during the oxidation of their respective substrate (NADH) as described previously. Briefly, a small scale preparation of bovine heart mitochondria was prepared as described before (Smith, A. L (1967), *Methods Enzymol.* 10, 81). Bovine heart submitochondrial particles (SMPs) were prepared as described by Matsuno-Yagi and stored in a buffer containing 0.25 M sucrose and 10 mM Tris-HCl, pH 7.4, at −80° C. (Matsuno-Yagi, A.; Hatefi, Y. J. (1985) *J. Biol. Chem.* 260, 11424). SMPs were diluted to 0.5 mg/mL. Mitochondrial complexes I, III, and IV activity were assayed at 30 C and monitored spectrophotometrically using a Beckman Coulter DU-530 (340 nm, $\varepsilon=6.22$ mM$^{-1}$ cm$^{-1}$). NADH oxidase activity was determined in 50 mM Hepes buffer containing 5 mM $MgCl_2$, pH 7.5, in a total volume of 2.5 mL. The final mitochondrial protein concentration was 30 µg/mL. The initial rates of NADH oxidation were calculated from the linear portion of the traces.

NADH: Ubiquinone Oxidoreductase Activity (Complex I Activity)

The inhibition of NADH-Q oxidoreductase activity was determined using the same experimental conditions described previously. SMPs (30 µg/mL) were incubated at 30° C. for 5 min with the test compound in 1 mL of 50 mM phosphate buffer, pH 7.4, containing 0.25 M sucrose, 1 mM $MgCl_2$, 2 µM antimycin A and 2 mM KCN. The reaction was initiated by the addition of 75 µM NADH and 15 µM coenzyme Q1. Enzymatic activity, measured by the decrease in NADH absorbance, was monitored at 340 nm.

In Vitro SIRT3 Deacetylation Activity

Further characterization the effects of the modified methylene blue analogue on mitochondrial bioenergetics and sirtuin activation is measured. The mitochondrial $NAD^+$/NADH ratio is a critical factor in sirtuin activation. Thus, the modulation of the $NAD^+$/NADH ratio appears to be a promising strategy to fix the impairment of mitochondrial respiration (hyperacetylation) found in FRDA as a result of Sirt3 inhibition. Complex I activity in bovine heart submitochondrial particles (SMP) was coupled with recombinant SIRT3 (rSIRT3) activity using a luminogenic acetylated sirt3 peptide substrate (Chemilum de Lys HDAC/SIRT Kit) and NADH. The co-substrate $NAD^+$ was generated by oxidation of NADH in presence and absence of rotenone.

Frataxin Protein Expression (Western Blot)

Immortalized normal and FRDA lymphocyte cell lines were seeded at 500,000 cells per/mL (5 mL) in T-25 flask. Cultures were treated with the test compounds and incubated for 24 h. Cells were harvested by centrifugation, washed with saline buffer and then were lysed using 200 µL of lysis buffer (1% triton X-100, 0.1% SDS, Tris-HCl (50 Mm) pH 7.4, 150 mM NaCl, 0.5% sodium deoxycholate, 0.1 mM EDTA) with protease inhibitors (protease cocktail inhibitors (Roche Applied Science) and 1 mM phenylmethylsulfonyl fluoride (Sigma), and incubated on ice for 30 min with periodical mixing. These samples were cleared of insoluble material by centrifugation at 20,000× g for 10 min at 4° C. Total protein concentration was measured by the BCA kit (Thermo Fisher Scientific). NuPAGE LDS Sample Buffer (4X) and NuPAGE Reducing Agent (10X) was added the lysate and they were denatured at 95° C. for 5 min, then equal amounts of lysates (30 mg) were used for immunoblotting. Samples were resolved on a 4%-12% SDS-polyacrylamide Bis-Tris gels (Invitrogen) according to the manufacturer's recommendations and then proteins were transferred to nitrocellulose membranes. After blocking with Superblock-TBS (Thermo Fisher Scientific) for 1 hour to inhibit non-specific binding the blot was incubated with anti-frataxin monoclonal antibody (5 µg/mL) (18A5DB1) (Novex®) (Life technologies) overnight at 4° C. to detect endogenous frataxin in FRDA and normal lymphocytes. Following three 5-min washes with TBST, the blots were incubated with horseradish peroxidase-linked secondary anti-rabbit antibody IgGs (1:10,000, Sigma, in Superblock-TBS) at room temperature for 1 hr. The blots were washed three times for 5 min with TBST, rinsed with deionized $H_2O$, and developed with enhanced chemiluminescence (ECL) (BioRad Chemi-Doc) using West Pico Chemiluminescent Substrate (Pierce Biotechnology).

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated by reference for all purposes.

We claim:

1. A compound selected from the group consisting of:

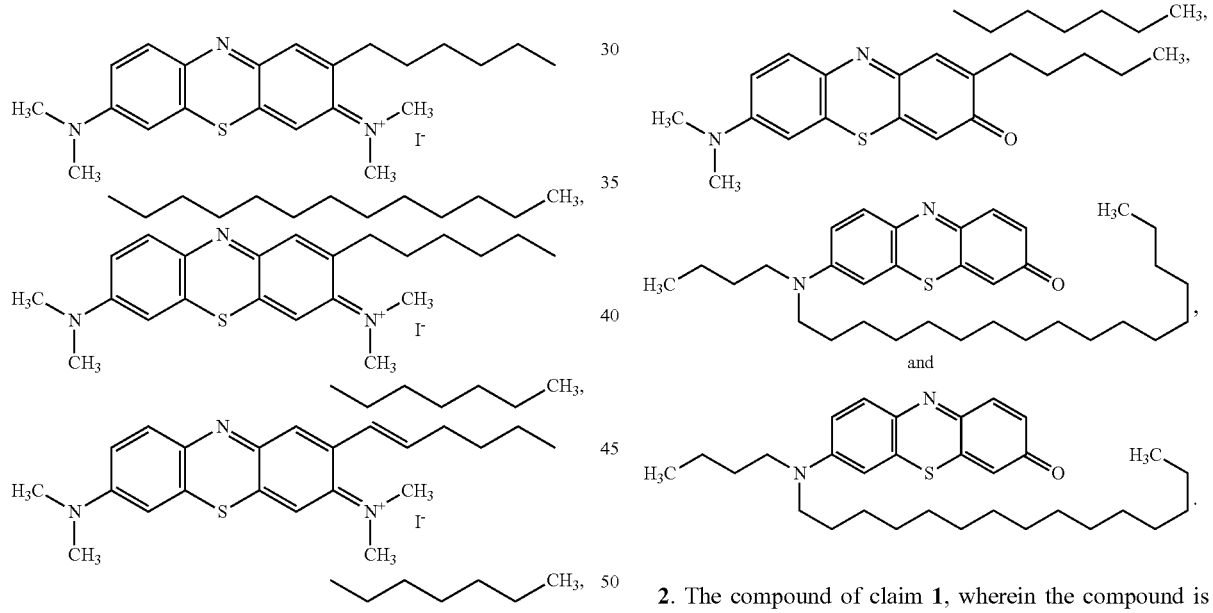

2. The compound of claim 1, wherein the compound is selected from the group consisting of:

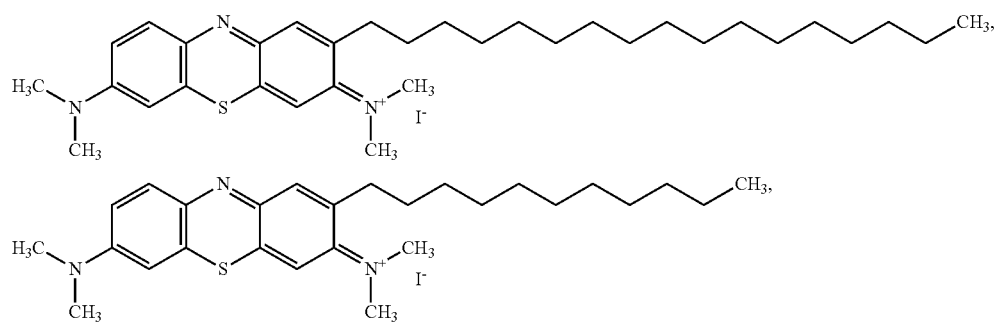

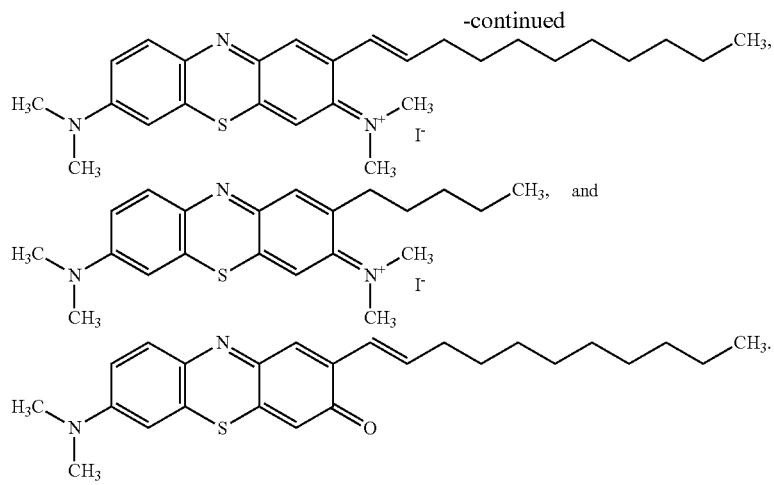
3. The compound of claim 1, wherein the compound is selected from the group consisting of:
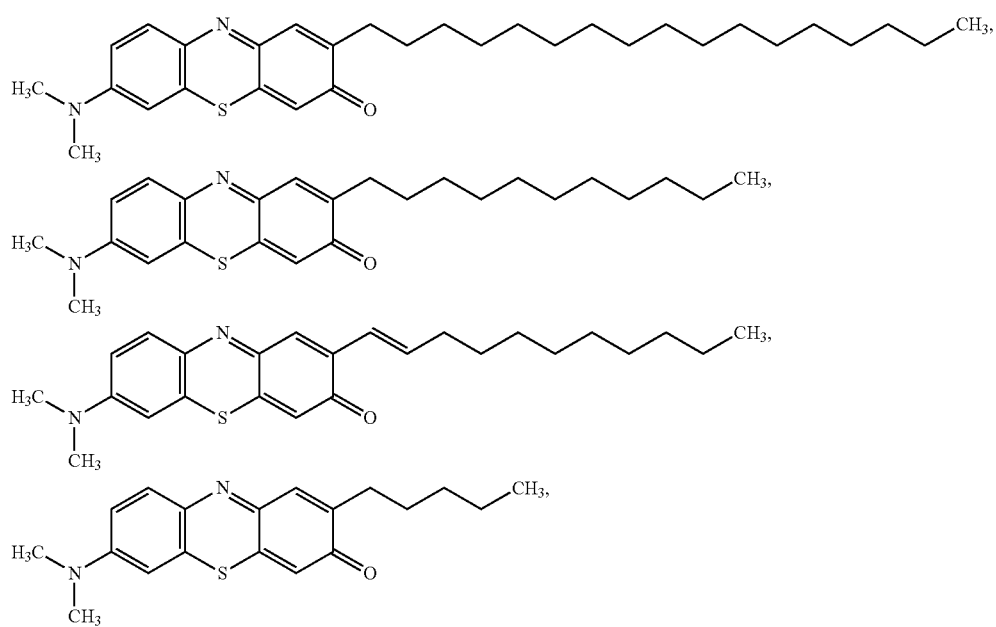
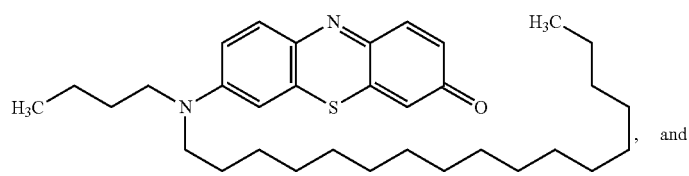
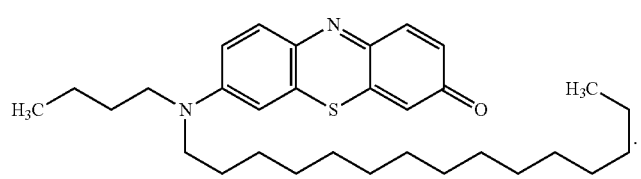

4. The compound of claim 1, wherein the compound is selected from the group consisting of:

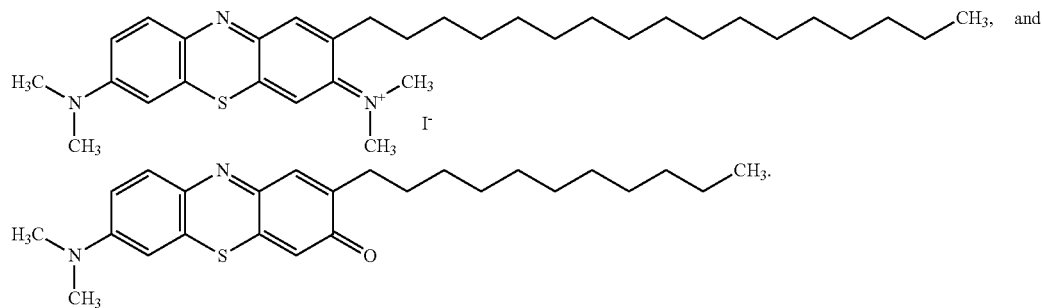

5. The compound of claim 1, wherein the compound is selected from the group consisting of:

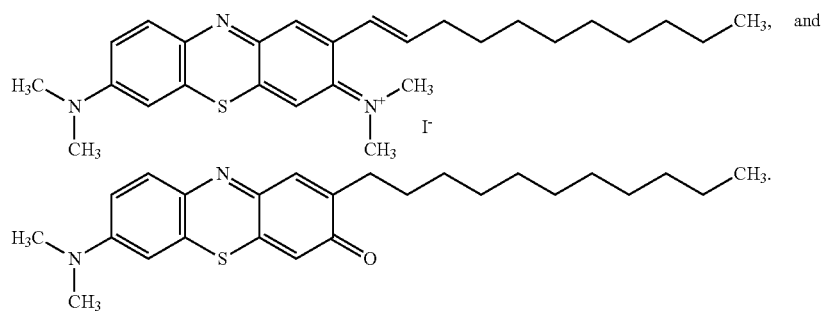

6. A pharmaceutical composition comprising a compound according to claim 1 and a pharmaceutically acceptable carrier, excipient and/or diluent.

7. A compound:

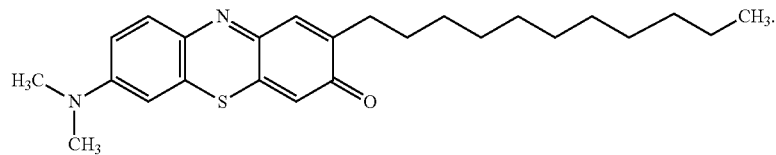 [SMILES: CCCCCCCCCCCc1cc2nc3ccc(N(C)C)cc3sc-2cc1=O]

8. A pharmaceutical composition comprising the compound according to claim 7 and a pharmaceutically acceptable carrier, excipient and/or diluent.

* * * * *